US008415336B2

(12) United States Patent
Steinhagen et al.

(10) Patent No.: US 8,415,336 B2
(45) Date of Patent: Apr. 9, 2013

(54) CYCLIC (AZA)INDOLIZINECARBOXAMIDES, THEIR PREPARATION AND THEIR USE AS PHARMACEUTICALS

(75) Inventors: Henning Steinhagen, Sulzbach (DE); Bodo Scheiper, München (DE); Hans Matter, Frankfurt am Main (DE); Gary McCort, Paris (FR); Guillaume Begis, Paris (FR); Pascale Goberville, Paris (FR); Berangere Thiers, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/353,889

(22) Filed: Jan. 19, 2012

(65) Prior Publication Data

US 2012/0232081 A1 Sep. 13, 2012

Related U.S. Application Data

(63) Continuation of application No. PCT/EP2010/060679, filed on Jul. 23, 2010.

(30) Foreign Application Priority Data

Jul. 29, 2009 (EP) .................................... 09290599

(51) Int. Cl.
*A61K 31/496* (2006.01)
*A61K 31/5025* (2006.01)
*C07D 471/04* (2006.01)
*C07D 487/04* (2006.01)

(52) U.S. Cl. ... 514/183; 514/218; 514/248; 514/253.04; 540/470; 540/575; 544/235; 544/362; 544/231

(58) Field of Classification Search .................... None
See application file for complete search history.

(56) References Cited

U.S. PATENT DOCUMENTS 5,278,161 A 1/1994 Branca et al.

FOREIGN PATENT DOCUMENTS

| EP | 1085021 A1 | 3/2001 |
| EP | 1958946 A1 | 8/2008 |
| WO | WO 96/31501 A1 | 10/1996 |
| WO | WO 2004/054507 A2 | 7/2004 |
| WO | WO 2005/026177 A1 | 3/2005 |
| WO | WO 2005/030144 A2 | 4/2005 |
| WO | WO 2005/061510 A1 | 7/2005 |
| WO | WO 2006/136859 A2 | 12/2006 |
| WO | WO 2011/012538 A1 | 2/2011 |

OTHER PUBLICATIONS

Vippagunta et al. Advanced Drug Delivery Reviews, vol. 48, pp. 3-26 (2001).*
Scheiper et al. Bioorganic & Medicinal Chemistry Letters, vol. 20, pp. 6268-6272 (2010).*
Zaman, et al., Drugs Targeting the Renin-Angiotensin-Aldosterone System, Nature Reviews Drug Discovery, vol. 1, No. 8, (2002), pp. 621-636.
Azizi, et al., Renin Inhibition With Aliskiren: where are we now, and where are we going?, J. Hypertens. vol. 24, (2006), pp. 243-256.
Barton, et al., A Useful Synthesis of Pyrroles From Nitroolefins, Tetrahedron, vol. 46, No. 21, pp. 7587-7598, (1990).
Becker, et al., Synthesis and Photochemical Properties of 1,3-Di-9-Anthryl-2-Propanol, 1,3-Di-9-Anthrylacetone, and Related Propano-Linked Anthracenes, J. Org. Chem., vol. 54, pp. 3182-3188, (1989).
Boyle, et al., Sigmatropic Rearrangements of 2,4-Dinitrophenyl Oximes, ARKIVOC, (2003), (vii), pp. 67-79.
Bradbury, et al., 1,2,4-Triazolo[4,3-a]Pyrazine Derivatives With Human Renin Inhibitory Activity. 3.1 Synthesis and Biological Properties of Aminodeoxystatine and Difluorostatone Derivatives, J. Med. Chem., (1991), vol. 34, pp. 151-157.
Brewster, U. C., et. al.. The Renin-Angiotensin-Aldosterone System and The Kidney: Effects on Kidney Disease, Am. J. Med., vol. 116, pp. 263-272, (2004).
Chai, et al., A Practical Parallel Synthesis of 2-Substituted Indolizines, Synlett, (2003), No. 13, pp. 2086-2088.
Chichibabin, Tautomerism in the Pyridine Series, Ber dt Chem Ges., vol. 60, (1927), pp. 1607-1617—English Abstract.
Choi, et al., Nonselective Bromination-Selective Debromination Strategy: Selective Bromination of Unsymmetrical Ketones on Singly Activated Carbon Against Doubly Activated Carbon, Organic Letters, vol. 5, No. 4, pp. 411-414, (2003).

(Continued)

*Primary Examiner* — Emily Bernhardt
(74) *Attorney, Agent, or Firm* — Ronald G. Ort

(57) ABSTRACT

The present invention relates to cyclic indolizinecarboxamides and azaindolizinecarboxamides of the formulae Ia and Ib,

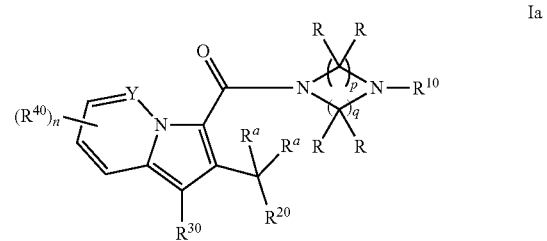

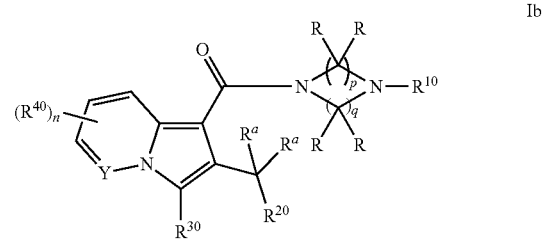

wherein R, $R^a$, $R^{10}$, $R^{20}$, $R^{30}$, $R^{40}$, Y, n, p and q have the meanings indicated in the claims, which are valuable pharmaceutical active compounds. Specifically, they inhibit the enzyme renin and modulate the activity of the renin-angiotensin system, and are useful for the treatment of diseases such as hypertension, for example. The invention furthermore relates to processes for the preparation of the compounds of the formulae Ia and Ib, their use and pharmaceutical compositions comprising them.

11 Claims, No Drawings

OTHER PUBLICATIONS

Davisson, et al., Complementation of Reduced Survival, Hypotension, and Renal Abnormalities in Angiotensinogen-Deficient Mice by the Human Renin and Human Angiotensinogen Genes, J. Clin. Invest., vol. 99, (1997), pp. 1258-1264.

Desideri, et al., An Efficient Synthesis of 3-Benzyl-2H-Chromenes as Potential Antipicornavirus Agents, Letters in Organic Chemistry, (2006), vol. 3, pp. 546-548.

Flaherty, et al., Palladium-Catalyzed Cross-Coupling of B-Benzyl-9-Borabicyclo[3.3.1]Nonane to Furnish Methylene-Linked Biaryls, Organic Letters, vol. 7, No. 22, pp. 4975-4978, (2005).

Fustero, et al., Enantioselective Organocatalytic Intramolecular Aza-Michael Reaction: A Concise Synthesis of (+)-Sedamine, (+)-Allosedamine, and (+)-Coniine, Organic Letters, vol. 9, No. 25, pp. 5283-5286, (2007).

Gaedeke, et al., Pharmacological Management of Renal Fibrotic disease, Expert Opin. Pharmacother., vol. 7, pp. 377-386, (2006).

Giardina, et al., Replacement of the Quinoline System in 2-Phenyl-4-Quinolinecarboxamide NK-3 Receptor Antagonists, II Farmaco, vol. 54, (1999), pp. 364-374.

Gradman, et al., The Efficacy of Aliskiren, a Direct Renin Inhibitor, in The Treatment of Hypertension, Reviews in Cardiovascular Medicine, vol. 8, No. Suppl. 2, (2007). pp. S22-S30.

Kakehi, et al., Preparation of New Nitrogen-Bridged Heterocycles. 55. Reinvestigation of the Bromination/Dehydrobromination of Ethyl 3-[2-(Methylthio)Indolizin-3-yl]Acrylate Derivatives, Chem. Pharm. Bull., vol. 52, No. 2, pp. 279-281, (2004).

Kim, et al., Synthesis and SAR of Pyrrolotriazine-4-One Based Eg5 Inhibitors, Bioorganic & Medicinal Chemistry Letters, vol. 16, (2006), pp. 3937-3942.

Kleinert, H.D., et. al., Renin Inhibition, Cardiovascular Drugs and Therapy, vol. 9, pp. 645-655, (1995).

Kornblum, et al., Synthesis of Quaternary Carbon Compounds, J. Org. Chem., (1981), vol. 46, pp. 1037-1039.

Lavoie, et al., Transgenic Mice for Studies of the Renin-Angiotensin System in Hypertension, Acta Physiol Scand, (2004), vol. 181, pp. 571-577.

Legault, et al., Highly Eddicient Synthesis of O-(2,4-Dinitrophenyl) Hydroxylamine. Application to the Synthesis of Substituted N-Benzoyliminopyridinium Ylides, J. Org. Chem., vol. 68, pp. 7119-7122, (2003).

Lonn, et al., The Clinical Revelance of Pharmacological Blood Pressure Lowering Mechanisms, Can. J. Cardiol., vol. 20, Suppl. B., (2004), pp. 83B-88B.

Mailbaum, et al., Renin Inhibitors as Novel Treatments for Cardiovascular Disease, Expert Opinion Ther. Patents, vol. 13, (2003), pp. 589-603.

Mealy, et al. Aliskiren Fumarate, Drugs of the Future, vol. 26, No. 12, pp. 1139-1148, (2001).

Merrill, et al., Chronic Hypertension and Altered Baroreflex Responses in Transgenic Mice Containing the Human Renin and Human Angiotensinogen Genes, J. Clin. Invest., (1996), vol. 97, pp. 1047-1055.

Mitsunobu, The Use of Diethyl Azodicarboxylate and Triphenylphosphine in Synthesis and Transformation of Natural Products, Synthesis, (1981), pp. 1-28.

Moser, et al., The Use of Renin Inhibitors in the Management of Hypertension, J. Clin. Hypertension, vol. 9, (2007), pp. 701-705.

Niwa, et al., Palladium-Catalyzed 2-Pyridylmethyl Transfer From 2-(2-Pyridyl)-Ethanol Derivatives to Organic Halides by Chelation-Assisted Cleavage of Unstrained Csp3-Csp3 Bonds, Angew. Chem. Int. Ed., (2007), vol. 46, pp. 2643-2645.

Okano, et al., Total Synthesis of (+)—Yatakemycin, JACS, (2006), vol. 128, pp. 7136-7137.

Ontoria, et al., Identification of Thieno[3,2-b]Pyrroles as Allosteric Inhibitors of Hepatitis C Virus NS5B Polymerase, Bioorganic & Medicinal Chemistry Letters, vol. 16, (2006), pp. 4026-4030.

Pfefferkorn, et al., Design and Synthesis of Hepatoselective, Pyrrole-Based HMG-CoA Reductase Inhibitors, Bioorganic & Medicinal Chemistry Letters, vol. 17, (2007), pp. 4538-4544.

Pilz, et al., Aliskiren, A Human Renin Inhibitor, Ameliorates Cardiac and Renal Damage in Double-Transgenic Rats, Hypertension, vol. 46, pp. 569-576, (2005).

Reid, et al., The Renin-Angiotensin System: Physiology, Pathophysiology, and Pharmacology, J. Physiol. Advances in Physiology Education, vol. 20, (1998), pp. S236-S245.

Scott, et al., Development of Inhibitors of the Aspartyl Protease Renin for the Treatment of Hypertension, Current Protein and Peptide Science, vol. 7, (2006), pp. 241-254.

Sinhababu, et al., Silica Gel-Assisted Reduction of Nitrostyrenes to 2-Aryl-1-Nitroalkanes With Sodium Borohydride, Tetrahedron Letters, vol. 24, No. 3, pp. 227-230, (1983).

Staessen, et al., Oral Renin inhibitors, The Lancet, vol. 368, No. 9545, pp. 1449-1456, (2006).

Tice, et al., Renin Inhibitors, Annual Reports in Medicinal Chemistry, vol. 41, (2006), pp. 155-167.

Tschitschibabin, Tautomerie in der Pyridin-Reihe, Ber. dt. Chem. Ges., 60, (1927), pp. 1607-1617.

Uchida, Methods for the Construction of the Indolizine Nucleus, Synthesis, (1976), pp. 209-236.

Wolfe, et al., Rational Development of Practical Catalysts for Aromatic Carbon-Nitrogen Bond Formation, Acc. Chem. Res., 1998 (31) pp. 805-818.

Wood, et al., Aliskiren, a Novel, Orally Effective Renin Inhibitor, Lowers Blood Pressure in Marmosets and Spontaneously Hypertensive Rats, J. Hypertens., vol. 23, (2005), pp. 417-426.

Yokokawa, et al., Recent Advances in the Discovery of Non-Peptidic Direct Renin Inhibitors as Antihypertensives: New Patent Application in Years 2000-2008, Expert Opinion on Therapeutic Patents, vol. 18, No. 6, (2008), pp. 581-602.

* cited by examiner

CYCLIC (AZA)INDOLIZINECARBOXAMIDES, THEIR PREPARATION AND THEIR USE AS PHARMACEUTICALS

FIELD OF THE INVENTION

The present invention relates to cyclic indolizinecarboxamides and azaindolizinecarboxamides of the formulae Ia and Ib,

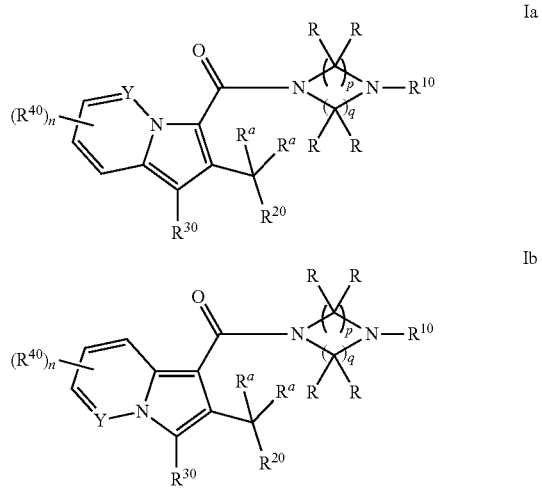

wherein R, $R^a$, $R^{10}$, $R^{20}$, $R^{30}$, $R^{40}$, Y, n, p and q have the meanings indicated below, which are valuable pharmaceutical active compounds. Specifically, they inhibit the enzyme renin and modulate the activity of the renin-angiotensin system, and are useful for the treatment of diseases such as hypertension, for example. The invention furthermore relates to processes for the preparation of the compounds of the formulae Ia and Ib, their use and pharmaceutical compositions comprising them.

BACKGROUND OF THE INVENTION

The renin-angiotensin system (RAS; also designated as renin-angiotensin aldosterone system, RAAS) is a key regulator of cardiovascular functions as well as for the balance of electrolytes and for maintaining body fluid volume, and a determinant of blood pressure (cf., for example, E. Lonn, Can. J. Cardiol. 20 (Suppl. B) (2004), 83B; I. A. Reid, Am. J. Physiol.: Advances in Physiology Education 20 (1998), S236). It acts via the effects of angiotensin II, an octapeptide hormone, which binds to angiotensin receptors. The formation of angiotensin II involves two main steps. In the first step, renin (EC 3.4.23.15; formerly EC 3.4.99.19 and EC 3.4.4.15), a 340 amino acid aspartyl proteinase, cleaves angiotensinogen to form the biologically inactive decapeptide angiotensin I. In the second step, angiotensin I is converted into angiotensin II by the zinc-dependent protease angiotensin-converting enzyme (ACE). Renin is produced in the juxtaglomerular cells of the kidney primarily in the form of the biologically inactive prorenin. Its release from the kidney and activation and subsequent RAS activation in normotensive humans is stimulated by sodium or volume depletion, or by a reduction in blood pressure.

RAS activity is the principal determinant of several pathological states since angiotensin II, the major effector molecule of this system, increases blood pressure both directly by arterial vasoconstriction and indirectly by liberating the sodium-retaining hormone aldosterone from the adrenal glands, accompanied by an increase in extracellular fluid volume, as well as having growth-promoting effects on vascular, cardiac and renal tissues which contribute to end-organ damage.

Pharmacological blockade of the RAS is an established way of treating various diseases, for example hypertension (cf., for example, Handbook of Hypertension, W. H. Birkenhäger et al. (ed.), Elsevier Science Publishers, Amsterdam (1986), vol. 8, 489). However, the therapeutic response achieved with the currently used types of RAS blockers, ACE inhibitors and angiotensin receptor blockers, although efficacious, is limited. This may be due to the rise in renin which is induced by these agents and results in an increase in angiotensin I which can be converted into angiotensin II via other pathways than by means of ACE. An inhibition of renin, which controls the initial and rate-limiting step in the RAS by catalyzing the cleavage of the Leu10-Val11 peptide bond of angiotensinogen resulting in the formation of the angiotensin peptides, would inhibit the complete RAS and thus be more efficient. Furthermore, whereas inhibition of ACE also affects the level of other peptides which are cleaved by ACE such as bradykinin, for example, which is associated with side effects of ACE inhibitors like cough or angioedema, renin is specific in that angiotensinogen is its only natural substrate. Inhibition of renin thus offers a specific and powerful way of lowering blood pressure (cf. M. Moser et al., J. Clin. Hypertension, 9 (2007), 701) as well as providing organ protection of organs such as the heart, kidney and brain and, besides for treating hypertension, thus is useful for treating disorders of the cardiovascular system, such as heart failure, cardiac insufficiency, cardiac failure, cardiac infarction, cardiac hypertrophy, vascular hypertrophy, left ventricular dysfunction, in particular left ventricular dysfunction after myocardial infarction, restenosis and angina pectoris; renal diseases, such as renal fibrosis, renal failure and kidney insufficiency; diabetes complications, such as nephropathy and retinopathy; glaucoma; and cerebral afflictions, such as cerebral hemorrhage, for example (with respect to the effect of the RAS on renal diseases and cardiac damage, cf., for example, U. C. Brewster, Am. J. Med. 116 (2004), 263; J. Gaedeke et al., Expert Opin. Pharmacother. 7 (2006), 377; B. Pilz et al., Hypertension 46 (2005), 569).

A large number of peptidic and peptidomimetic inhibitors of human renin with various stable transition-state analogues of the scissile peptide bond have been developed since about 1980 and contributed to the validation of renin as a therapeutic target (cf., for example, B. B. Scott et al., Curr. Protein Pept. Sci. 7 (2006), 241; J. Maibaum et al., Expert Opin. Ther. Patents 13 (2003), 589). However, these compounds generally suffer from deficiencies such as insufficient bioavailability (cf. H. D. Kleinert, Cardiovasc. Drugs Therapy 9 (1985), 645) or duration of action, or high cost of production. Recently, an orally active renin inhibitor, aliskiren (cf. Drugs Fut. 26 (2001), 1139; J. Wood et al., J. Hypertens. 23 (2005), 417; M. Azizi et al., J. Hypertens. 24 (2006), 243) has been marketed. But the property profile of aliskiren is not yet ideal, for example with respect to oral bioavailability, and a particular drawback of aliskiren is its complex molecular structure with four chiral centers and its multistep synthesis. Thus, there is still a great need for new, non-peptidic small molecule renin inhibitors which exhibit favorable properties, for example with respect to oral bioavailability or low molecular complexity and simple synthetic access. The present invention satisfies this need by providing the renin-inhibiting cyclic (aza)indolizinecarboxamides of the formulae Ia and Ib.

Various indolizine and azaindolizine derivatives have already been described. For example, certain indolizine derivatives, i.e. compounds containing the bicyclic ring system that is present in the compounds of the formulae Ia and Ib in case Y is a carbon atom, are described in WO 2004/054507, which relates to inhibitors of PDE4 useful for the treatment of diseases such as cancer or inflammatory disorders, or in WO 2006/136859, which relates to ligands of the CRTH2 receptor useful for the treatment of respiratory diseases. Certain 5-azaindolizine, or pyrrolo[1,2-b]pyridazine, derivatives, i.e. compounds containing the bicyclic ring system that is present in the compounds of the formulae Ia and Ib in case Y is nitrogen atom, are described in EP 1085021, which relates to inhibitors of $sPLA_2$ useful for the treatment of diseases such as septic shock or adult respiratory distress syndrome, or in WO 2005/030144, which relates to inhibitors of protein kinases useful for the treatment of proliferative disorders, such as cancer, and inflammatory disorders. The indolizinecarboxamides and azaindolizinecarboxamides of the present invention, wherein the amide nitrogen atom is a ring member of a 1,4- or 1,5-diazacycloalkane ring system, one of the carbon atoms in the 5-membered ring of the (aza)indolizine ring system, which is adjacent to a fusion position, carries a cyclic group, and the carbon atom in the 5-membered ring of the (aza)indolizine ring system which is not adjacent to the fusion positions, is linked via a carbon atom to a (hetero)aromatic group, have not yet been disclosed.

DESCRIPTION OF THE INVENTION

Thus, a subject of the present invention are the compounds of the formulae Ia and Ib, in any of their stereoisomeric forms or a mixture of stereoisomeric forms in any ratio, and the physiologically acceptable salts thereof, and the physiologically acceptable solvates of any of them,

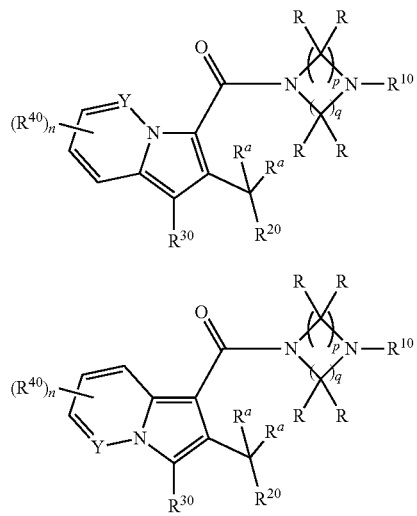

wherein
$R^a$ is chosen from hydrogen, fluorine and $(C_1-C_4)$-alkyl, wherein the two groups $R^a$ are independent of each other and can be identical or different, or the two groups $R^a$ together are a divalent $(C_2-C_5)$-alkyl group;

R is chosen from hydrogen, $(C_1-C_6)$-alkyl which is optionally substituted by one or more identical or different substituents $R^1$, and $(C_3-C_7)$-cycloalkyl, wherein all groups R are independent of each other and can be identical or different, or two groups R bonded to the same carbon atom together are a divalent $(C_2-C_5)$-alkyl group;
$R^1$ is chosen from $(C_3-C_7)$-cycloalkyl, phenyl, heteroaryl, $Het^1$, hydroxy, $(C_1-C_4)$-alkyl-O—, $(C_1-C_4)$-alkyl-S(O)$_m$—, $R^2$—N($R^3$)—C(O)—, $R^4$—O—C(O)— and cyano;
$R^2$ is chosen from hydrogen, $(C_1-C_6)$-alkyl which is optionally substituted by one or more identical or different substituents $R^5$, and $(C_3-C_7)$-cycloalkyl, wherein all groups $R^2$ are independent of each other and can be identical or different;
$R^3$, $R^4$, $R^6$, $R^7$ and $R^8$ are chosen from hydrogen and $(C_1-C_4)$-alkyl, wherein all groups $R^3$, $R^4$, $R^6$, $R^7$ and $R^8$ are independent of each other and can be identical or different;
$R^5$ is chosen from hydroxy, $(C_1-C_4)$-alkyl-O—, $(C_1-C_4)$-alkyl-S(O)$_m$—, $R^6$—N($R^7$)—C(O)—, $R^8$—O—C(O)—, cyano, $(C_3-C_7)$-cycloalkyl, phenyl, heteroaryl and $Het^1$;
$R^{10}$ is chosen from hydrogen, $(C_1-C_6)$-alkyl-O—C(O)— and $(C_3-C_7)$-cycloalkyl-$C_vH_{2v}$—O—C(O)—;
$R^{20}$ is chosen from phenyl and heteroaryl which are optionally substituted by one or more identical or different substituents chosen from halogen, $(C_1-C_4)$-alkyl, $(C_1-C_4)$-alkyl-O—, $(C_1-C_4)$-alkyl-S(O)$_m$— and cyano;
$R^{30}$ is chosen from $(C_5-C_7)$-cycloalkyl, $(C_5-C_7)$-cycloalkenyl, tetrahydropyranyl, phenyl and heteroaryl, wherein cycloalkyl and cycloalkenyl are optionally substituted by one or more identical or different substituents chosen from fluorine, $(C_1-C_4)$-alkyl and hydroxy, and phenyl and heteroaryl are optionally substituted by one or more identical or different substituents chosen from halogen, $(C_1-C_4)$-alkyl, $(C_1-C_4)$-alkyl-O— and cyano;
$R^{40}$ is chosen from halogen, $(C_1-C_4)$-alkyl, $(C_3-C_7)$-cycloalkyl-$C_vH_{2v}$—, hydroxy, $(C_1-C_4)$-alkyl-O—, $(C_1-C_4)$-alkyl-S(O)$_m$—, $R^{41}$—N($R^{42}$)—, $Het^2$, $R^{41}$—N($R^{42}$)—C(O)—, $Het^2$-C(O)—, cyano, $R^{41}$—N($R^{42}$)—S(O)$_2$— and $Het^2$-S(O)$_2$—, wherein all substituents $R^{40}$ are independent of each other and can be identical or different;
$R^{41}$ is chosen from hydrogen, $(C_1-C_4)$-alkyl and $(C_3-C_7)$-cycloalkyl-$C_vH_{2v}$—, wherein all groups $R^{41}$ are independent of each other and can be identical or different;
$R^{42}$ is chosen from hydrogen and $(C_1-C_4)$-alkyl, wherein all groups $R^{42}$ are independent of each other and can be identical or different;
Y is chosen from N, CH and C(($C_1-C_4$)-alkyl);
heteroaryl is an aromatic monocyclic, 5-membered or 6-membered, heterocyclic group which comprises 1, 2 or 3 identical or different ring heteroatoms chosen from N, O and S, wherein one of the ring nitrogen atoms can carry a hydrogen atom or a $(C_1-C_4)$-alkyl substituent, and wherein the heteroaryl group is bonded via a ring carbon atom;
$Het^1$ is a saturated, monocyclic, 4-membered to 7-membered heterocyclic group which comprises 1 or 2 identical or different ring heteroatoms chosen from N, O and S, wherein the group $Het^1$ is bonded via a ring carbon atom or a ring nitrogen atom, wherein ring nitrogen atoms can carry a hydrogen atom or a substituent chosen from $(C_1-C_4)$-alkyl, $(C_1-C_6)$-alkyl-O—C(O)— and $(C_3-C_7)$-cycloalkyl-$C_vH_{2v}$—O—C(O)—, wherein ring sulfur atoms can carry one or two oxo groups, and wherein $Het^1$ is optionally substituted on ring carbon atoms by one or more identical or different substituents chosen from fluorine, $(C_1-C_4)$-alkyl and oxo;
$Het^2$ is a saturated, monocyclic, 4-membered to 7-membered heterocyclic group which comprises a ring nitrogen atom via which the group $Het^2$ is bonded and optionally an additional ring heteroatom chosen from N, O and S, wherein the additional ring nitrogen atom carries a hydrogen atom or a substituent chosen from $(C_1-C_4)$-alkyl, $(C_1-C_6)$-alkyl-O—C(O)— and $(C_3-C_7)$-cycloalkyl-$C_vH_{2v}$—O—C(O)—, wherein the ring sulfur atom can carry one or two oxo groups, and wherein $Het^2$ is optionally substituted on ring carbon atoms by one or more identical or different substituents chosen from fluorine, $(C_1-C_4)$-alkyl and oxo;
m is chosen from 0, 1 and 2, wherein all numbers m are independent of each other and can be identical or different;
n is chosen from 0, 1, 2 and 3;
p and q, which are independent of each other and can be identical or different, are chosen from 2 and 3;
v is chosen from 0, 1 and 2, wherein all numbers v are independent of each other and can be identical or different;
wherein all alkyl groups, independently of each other, are optionally substituted by one or more fluorine atoms;
wherein all cycloalkyl groups, independently of each other, are optionally substituted by one or more identical or different substituents chosen from fluorine and $(C_1-C_4)$-alkyl, unless specified otherwise;
wherein all phenyl and heteroaryl groups present in $R^1$ and $R^5$, independently of each other, are optionally substituted by one or more identical or different substituents chosen from halogen, $(C_1-C_4)$-alkyl, $(C_1-C_4)$-alkyl-O—, $(C_1-C_4)$-alkyl-S$(O)_2$— and cyano.

If structural elements such as groups, substituents or numbers can occur several times in the compounds of the formulae Ia and Ib, they are all independent of one another and can in each case have any of the indicated meanings, and can in each case be identical to or different from any other such element.

Alkyl groups, i.e. saturated hydrocarbon residues, can be straight-chain (linear) or branched. This also applies if these groups are substituted or are part of another group, for example an alkyl-O— group (alkyloxy group, alkoxy group) or an alkyl-S$(O)_m$— group. Depending on the respective definition, the number of carbon atoms in an alkyl group can be 1, 2, 3, 4, 5 or 6. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Examples of alkyl-O— are methoxy, ethoxy, n-propoxy, isopropoxy, n-butoxy, isobutoxy, tert-butoxy and n-pentoxy. Examples of alkyl-S$(O)_m$— are methylsulfanyl-($CH_3$—S—), methanesulfinyl-($CH_3$—S(O)—), methanesulfonyl-($CH_3$—S$(O)_2$—), ethylsulfanyl-($CH_3$—$CH_2$—S—), ethanesulfinyl-($CH_3$—$CH_2$—S(O)—), ethanesulfonyl-($CH_3$—$CH_2$—S$(O)_2$—), 1-methylethylsulfanyl-$((CH_3)_2CH$—S—), 1-methylethanesulfinyl-$((CH_3)_2CH$—S(O)—) and 1-methylethanesulfonyl-$((CH_3)_2CH$—S$(O)_2$—). In one embodiment of the invention the number m is chosen from 0 and 2, in another embodiment it is 0, in another embodiment it is 2, wherein all numbers m are independent of each other and can be identical or different.

A substituted alkyl group can be substituted in any positions, provided that the resulting compound is sufficiently stable and is suitable as a pharmaceutical active compound. The prerequisite that a specific group and a compound of the formula Ia or Ib are sufficiently stable and suitable as a pharmaceutical active compound, applies in general with respect to all groups in the compounds of the formulae Ia and Ib. If an alkyl group is optionally substituted by one or more fluorine atoms, it can be unsubstituted, i.e. not carry fluorine atoms, or substituted, for example by 1, 2, 3, 4, 5, 6, 7, 8, 9, 10 or 11 fluorine atoms, or by 1, 2, 3, 4 or 5 fluorine atoms, or by 1, 2 or 3 fluorine atoms, which can be present in any positions. For example, in a fluoro-substituted alkyl group one or more methyl groups can carry three fluorine atoms each and be present as trifluoromethyl groups, and/or one or more methylene groups ($CH_2$) can carry two fluorine atoms each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-S$(O)_m$— groups are trifluoromethylsulfanyl-($CF_3$—S—), trifluoromethanesulfinyl-($CF_3$—S(O)—) and trifluoromethanesulfonyl-($CF_3$—S$(O)_2$—).

If applicable, the above explanations with respect to alkyl groups apply correspondingly to divalent alkyl groups (alkanediyl groups) including the divalent alkyl group $C_vH_{2v}$, which can also be regarded as the alkyl part of a substituted alkyl group. Thus, divalent alkyl groups including the divalent alkyl group $C_vH_{2v}$ can also be straight-chain or branched, the bonds to the adjacent groups can be present in any positions and can start from the same carbon atom or from different carbon atoms, and they can be substituted by fluorine. Examples of divalent alkyl groups are —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —CH($CH_3$)—, —C($CH_3$)$_2$—, —CH($CH_3$)—$CH_2$—, —$CH_2$—CH($CH_3$)—, —C($CH_3$)$_2$—$CH_2$— and —$CH_2$—C($CH_3$)$_2$—. Examples of fluoro-substituted divalent alkyl groups which can contain 1, 2, 3, 4, 5 or 6 fluorine atoms, for example, are —CHF—, —$CF_2$—, —$CF_2$—$CH_2$—, —$CH_2$—$CF_2$—, —$CF_2$—$CF_2$—, —CF($CH_3$)—, —C($CF_3$)$_2$—, —C($CH_3$)$_2CF_2$— and —$CF_2$—C($CH_3$)$_2$—. If the number v in a divalent alkyl group $C_vH_{2v}$ is 0 (zero), the two adjacent groups which are bonded to this group are directly bonded to one another through a single bond. For example, if the group $R^{40}$ is the group $(C_3-C_7)$-cycloalkyl-$C_vH_{2v}$—, which group is bonded to the remainder of the molecule via the $C_vH_{2v}$ moiety as is symbolized by the terminal line (hyphen) next to the $C_vH_{2v}$ moiety representing the free bond, and the number v therein is 0, the $(C_3-C_7)$-cycloalkyl group is bonded directly through a single bond to the carbon atom which carries the group $R^{40}$. In one embodiment of the invention the number v is chosen from 0 and 1, in another embodiment it is 0, in another embodiment it is 1, wherein all numbers v are independent of each other and can be identical or different.

The number of ring carbon atoms in a cycloalkyl group can be 3, 4, 5, 6 or 7. The number of ring carbon atoms in a cycloalkenyl group can be 5, 6 or 7. Examples of cycloalkyl are cyclopropyl, cyclobutyl, cyclopentyl, cyclohexyl and cycloheptyl, examples of cycloalkenyl are cyclopentenyl, cyclohexenyl and cycloheptenyl. The double bond in a cycloalkenyl group can be present in any position with respect to the carbon atom in position 1 via which the group is bonded to the (aza)indolizine ring, and cycloalkenyl can thus be cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, for example. In one embodiment of the present invention, a cycloalkyl group, such as $(C_3-C_7)$-cycloalkyl, in the definition of any group is chosen from any one or more of the said specific cycloalkyl groups, for example from cyclopropyl and cyclobutyl, or from cyclopropyl, cyclobutyl and cyclopentyl, or from cyclopropyl, cyclopentyl and cyclohexyl, or from cyclopentyl and cyclohexyl, or from cyclopentyl, cyclohexyl and cycloheptyl, wherein all cycloalkyl groups are independent of each other and can be identical or different. Similarly, in one embodiments a cycloalkenyl group is chosen from any one or more of the said specific cycloalkenyl groups, for example from cyclopentenyl and cyclohexenyl, or from cyclohexenyl and cycloheptenyl, or from cyclopent-1-enyl, cyclopent-2-enyl, cyclohex-1-enyl, cyclohex-2-enyl, cyclohept-1-enyl and cyclohept-2-enyl, or from cyclopent-2-enyl, cyclopent-3-enyl, cyclohex-2-enyl, cyclohex-3-enyl, cyclohept-2-enyl, cyclohept-3-enyl and cyclohept-4-enyl, or from cyclopent-2-enyl and cyclohex-2-enyl, or from cyclopent-2-enyl, cyclohex-2-enyl and cyclohept-2-enyl. In one embodiment of the invention, the carbon atom via which the cycloalkenyl group representing $R^{30}$ is bonded to the (aza)indolizine ring, is not part of the double bond, i.e., the cycloalkenyl group is not a cycloalk-1-enyl group. Cycloalkyl groups and cycloalkenyl groups generally are optionally substituted by one or more ($C_1$-$C_4$)-alkyl substituents. I.e., they are unsubstituted and do not carry alkyl substituents, or are substituted, for example by 1, 2, 3 or 4 identical or different ($C_1$-$C_4$)-alkyl substituents, for example by methyl groups and/or ethyl groups and/or isopropyl groups and/or tert-butyl groups, in particular by methyl groups, which substituents can be present in any positions. Examples of alkyl-substituted cycloalkyl groups are 1-methyl-cyclopropyl, 2,2-dimethyl-cyclopropyl, 1-methyl-cyclopentyl, 2,3-dimethyl-cyclopentyl, 1-methyl-cyclohexyl, 4-methyl-cyclohexyl, 4-isopropyl-cyclohexyl, 4-tert-butyl-cyclohexyl and 3,3,5,5-tetramethyl-cyclohexyl. Examples of alkyl-substituted cycloalkenyl groups are 1-methyl-cyclopent-2-enyl, 2-methyl-cyclopent-2-enyl, 3-methyl-cyclopent-2-enyl, 3,4-dimethyl-cyclopent-3-enyl, 1-methyl-cyclohex-2-enyl, 2-methyl-cyclohex-2-enyl, 3-methyl-cyclohex-2-enyl, 4-methyl-cyclohex-2-enyl, 2-methyl-cyclohex-3-enyl, 3-methyl-cyclohex-3-enyl, 4-methyl-cyclohex-3-enyl, 2,3-dimethyl-cyclohex-2-enyl, 4,4-dimethyl-cyclohex-2-enyl, 3,4-dimethyl-cyclohex-3-enyl. Cycloalkyl groups and cycloalkenyl groups generally also are optionally substituted by one or more fluorine atoms. I.e., they are unsubstituted and do not carry fluorine atoms, or are substituted, for example by 1, 2, 3, 4, 5, 6, 7, 8, 9, 10 or 11 fluorine atoms, or by 1, 2, 3, 4, 5 or 6 fluorine atoms. Cycloalkyl groups and cycloalkenyl groups can also be substituted simultaneously by fluorine and alkyl. The fluorine atoms can be present in any positions and can also be present in an alkyl substituent. Examples of fluoro-substituted cycloalkyl groups are 1-fluoro-cyclopropyl, 2,2-difluoro-cyclopropyl, 3,3-difluoro-cyclobutyl, 1-fluoro-cyclohexyl, 4,4-difluoro-cyclohexyl and 3,3,4,4,5,5-hexafluoro-cyclohexyl. Examples of fluoro-substituted cycloalkenyl groups are 1-fluoro-cyclopent-2-enyl, 1-fluoro-cyclohex-2-enyl, 4-fluoro-cyclohex-2-enyl, 4,4-difluoro-cyclohex-2-enyl. In one embodiment of the invention, cycloalkyl groups are not optionally substituted by substituents chosen from fluorine and ($C_1$-$C_4$)-alkyl. If a cycloalkyl group or cycloalkenyl group can be substituted by further substituents like hydroxy, as in the case of a cycloalkyl group or cycloalkenyl group representing $R^{30}$, it can be substituted merely by one or more such further substituents like hydroxy and not by substituents chosen from fluorine and ($C_1$-$C_4$)-alkyl, or by one or more such further substituents and simultaneously by one or more substituents chosen from fluorine and ($C_1$-$C_4$)-alkyl. In one embodiment, the number of such further substituents like hydroxy which can be present on a cycloalkyl or cycloalkenyl group, is 1, 2 or 3, in another embodiment 1 or 2, in another embodiment 1. In one embodiment, the total number of all substituents in a cycloalkyl group or cycloalkenyl group is 1, 2, 3, 4, 5, 6, 7 or 8, in another embodiment 1, 2, 3, 4 or 5, in another embodiment 1, 2 or 3. Such further substituents like hydroxy can be present in any positions, provided that the resulting compound is sufficiently stable and is suitable as a subgroup in a pharmaceutical active compound. In one embodiment, a hydroxy substituent is not present in position 1 of a cycloalkenyl group or cycloalkyl group representing $R^{30}$. In one embodiment, in a cycloalkenyl group a hydroxy substituent is not present on a carbon atom which is part of the double bond. Examples of hydroxy-substituted cycloalkyl groups are 3-hydroxy-cyclobutyl, 2-hydroxy-cyclopentyl, 3-hydroxy-cyclopentyl, 3,4-dihydroxy-cyclopentyl, 2-hydroxy-cyclohexyl, 3-hydroxy-cyclohexyl, 4-hydroxy-cyclohexyl, 2,3-dihydroxy-cyclohexyl, 2,4-dihydroxy-cyclohexyl, 3,4-dihydroxy-cyclohexyl, 3,5-dihydroxy-cyclohexyl, 3,4,5-trihydroxy-cyclohexyl, 2-hydroxy-cycloheptyl, 3-hydroxy-cycloheptyl, 4-hydroxy-cycloheptyl. Examples of hydroxy-substituted cycloalkenyl groups are 5-hydroxy-cyclopent-2-enyl, 4-hydroxy-cyclohex-2-enyl, 5-hydroxy-cyclohex-2-enyl, 6-hydroxy-cyclohex-2-enyl, 6-hydroxy-cyclohex-3-enyl. Examples of the group cycloalkylalkyl-, which can be present in the group ($C_3$-$C_7$)-cycloalkyl-$C_vH_{2v}$—, are cyclopropylmethyl-, cyclobutylmethyl-, cyclopentylmethyl-, cyclohexylmethyl-, cycloheptylmethyl-, cyclopropyldifluoromethyl-, cyclobutyldifluoromethyl-, cyclopentyldifluoromethyl-, cyclohexyldifluoromethyl-, cycloheptyldifluoromethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-.

A tetrahydropyranyl group representing $R^{30}$, which group can also be designated as oxanyl group or tetrahydro-2H-pyranyl group, can be bonded via any carbon atom and can be tetrahydropyran-2-yl, tetrahydropyran-3-yl or tetrahydropyran-4-yl. In one embodiment of the invention, tetrahydropyranyl is tetrahydropyran-3-yl or tetrahydropyran-4-yl, in another embodiment tetrahydropyranyl is tetrahydropyran-4-yl. In substituted phenyl groups, the substituents can be present in any positions. In monosubstituted phenyl groups, the substituent can be present in the 2-position, the 3-position or the 4-position. In disubstituted phenyl groups, the substituents can be present in 2,3-position, 2,4-position, 2,5-position, 2,6-position, 3,4-position or 3,5-position. In trisubstituted phenyl groups, the substituents can be present in 2,3,4-position, 2,3,5-position, 2,3,6-position, 2,4,5-position, 2,4,6-position or 3,4,5-position. If a phenyl group carries four substituents, of which one, two, three or four substituents can be fluorine atoms, for example, the unsubstituted ring carbon atom can be present in the 2-position, the 3-position or the 4-position. If a polysubstituted phenyl group or heteroaryl group carries different substituents, each substituent can be present in any suitable position, and the present invention comprises all positional isomers. The number of substituents in a substituted phenyl group can be 1, 2, 3, 4 or 5. In one embodiment, a substituted phenyl group, and likewise a substituted heteroaryl group, carries 1, 2 or 3, in another embodiment 1 or 2, identical or different substituents, in another embodiment 1 substituent, wherein all phenyl and heteroaryl groups are independent of each other. In one embodiment of the invention, the substituents in substituted phenyl and heteroaryl groups are independently of each other chosen from any one or more of the substituents listed in the respective definition, for example by substituents chosen from halogen, ($C_1$-$C_4$)-alkyl, ($C_1$-$C_4$)-alkyl-O— and ($C_1$-$C_4$)-alkyl- S(O)$_m$—, or from halogen, (C$_1$-C$_4$)-alkyl, (C$_1$-C$_4$)-alkyl-O— and (C$_1$-C$_4$)-alkyl-S(O)$_2$—, or from halogen, (C$_1$-C$_4$)-alkyl, (C$_1$-C$_4$)-alkyl-O— and cyano, or from halogen, (C$_1$-C$_4$)-alkyl and (C$_1$-C$_4$)-alkyl-O—, or from halogen and (C$_1$-C$_4$)-alkyl, provided that the substituents are comprised by the definition of the respective phenyl or heteroaryl group, wherein all alkyl groups can be unsubstituted or substituted by one or more fluorine atoms and, as an example of substituents containing fluorine-substituted alkyl, the substituents comprising the group CF$_3$ (trifluoromethyl) such as CF$_3$ itself, CF$_3$—O— or CF$_3$—S— may be included in each list of substituents in addition to substituents comprising unsubstituted alkyl.

In a heteroaryl group, which is a residue of an aromatic monocyclic, 5-membered or 6-membered heterocyclic ring system, the ring heteroatoms indicated in the definition of the group can be present in any combination and can be present in any suitable position, provided that the group is in line with its definition and the resulting compound of the formula Ia or Ib is stable and suitable as a pharmaceutical active compound. The one of the ring nitrogen atoms specifically referred to in the definition of the group heteroaryl which can carry a hydrogen atom or a substituent such as alkyl, is the ring nitrogen atom in a 5-membered ring system such as pyrrole, pyrazole, imidazole or triazole to which an exocyclic atom or group is bonded. Examples of ring systems from which a heteroaryl group can be derived are pyrrole, furan, thiophene, imidazole, pyrazole, triazoles such as [1,2,3]triazole and [1,2,4]triazole, oxazole ([1,3]oxazole), isoxazole ([1,2]oxazole), thiazole ([1,3]thiazole), isothiazole ([1,2]thiazole), oxadiazoles such as [1,2,4]oxadiazole, [1,3,4]oxadiazole and [1,2,5]oxadiazole, thiadiazoles such as [1,3,4]thiadiazole, pyridine, pyridazine, pyrimidine, pyrazine, triazines such as [1,2,3]triazine, [1,2,4]triazine and [1,3,5]triazine. In one embodiment of the invention, a heteroaryl group comprises one or two identical or different ring heteroatoms, in another embodiment of the invention heteroaryl comprises one ring heteroatom, which are defined as indicated. In another embodiment heteroaryl is chosen from thiophenyl, thiazolyl and pyridinyl, in another embodiment from thiophenyl and pyridinyl, in another embodiment heteroaryl is thiophenyl, in another embodiment heteroaryl is pyridinyl. Heteroaryl groups can be bonded via any ring carbon atom. For example, a thiophenyl group (thienyl group) can be thiophen-2-yl (2-thienyl) or thiophen-3-yl (3-thienyl), furanyl can be furan-2-yl or furan-3-yl, pyridinyl (pyridyl) can be pyridin-2-yl, pyridin-3-yl or pyridin-4-yl, pyrazolyl can be 1H-pyrazol-3-yl, 1H-pyrazol-4-yl or 2H-pyrazol-3-yl, imidazolyl can be 1H-imidazol-2-yl, 1H-imidazol-4-yl or 3H-imidazolyl-4-yl, thiazolyl can be thiazol-2-yl, thiazol-4-yl or thiazol-5-yl, [1,2,4]triazolyl can be 1H-[1,2,4]triazol-3-yl, 2H-[1,2,4]triazol-3-yl or 4H-[1,2,4]triazol-3-yl.

In substituted heteroaryl groups, the substituents can be present in any positions, for example in a thiophen-2-yl group or a furan-2-yl group in the 3-position and/or in the 4-position and/or in the 5-position, in a thiophen-3-yl group or a furan-3-yl group in the 2-position and/or in the 4-position and/or in the 5-position, in a pyridin-2-yl group in the 3-position and/or in the 4-position and/or in the 5-position and/or in the 6-position, in a pyridin-3-yl group in the 2-position and/or in the 4-position and/or in the 5-position and/or in the 6-position, in a pyridin-4-yl group in the 2-position and/or in the 3-position and/or in the 5-position and/or in the 6-position. In one embodiment, a substituted heteroaryl group is substituted by one, two or three, in another embodiment by one or two, identical or different substituents, in another embodiment by one substituent. If a ring nitrogen atom is present which can carry a hydrogen atom or a substituent, the substituent on this nitrogen atom can be a methyl group, an ethyl group, a propyl group or a tert-butyl group, for example, which groups are optionally substituted by one or more fluorine atoms. Generally, suitable ring nitrogen atoms in the compounds of the formulae Ia and Ib, for example the nitrogen atom in a pyridinyl group or a nitrogen atom in a [1,2,5]oxadiazolyl group, can also carry an oxido substituent —O$^-$ and the compound thus be present in the form of an N-oxide.

In one embodiment of the invention, the ring heteroatoms in Het$^1$ are chosen from N and O, in another embodiment from O and S, in another embodiment they are O atoms, in another embodiment they are N atoms. In one embodiment, the number of ring heteroatoms in Het$^1$ is 1. In one embodiment, two ring oxygen atoms in Het$^1$ are not present in adjacent ring positions, in another embodiment two ring heteroatoms chosen from O and S are not present in adjacent ring positions, in another embodiment two ring heteroatoms are not present in adjacent ring positions. Ring nitrogen atoms in Het$^1$, except for a ring nitrogen atom via which Het$^1$ is bonded, carry a hydrogen atom or a substituent as specified. In one embodiment, optional substituents on ring nitrogen atoms in Het$^1$ are chosen from (C$_1$-C$_4$)-alkyl and (C$_1$-C$_6$)-alkyl-O—C(O)—, in another embodiment from (C$_1$-C$_6$)-alkyl-O—C(O)— and (C$_3$-C$_7$)-cycloalkyl-C$_v$H$_{2v}$—O—C(O)—, in another embodiment from (C$_1$-C$_4$)-alkyl, in another embodiment from (C$_1$-C$_6$)-alkyl-O—C(O)—. In one embodiment, optional substituents on ring carbon atoms in Het$^1$ are chosen from fluorine and (C$_1$-C$_4$)-alkyl, in another embodiment from (C$_1$-C$_4$)-alkyl and oxo, in another embodiment from (C$_1$-C$_4$)-alkyl. In case Het$^1$ contains any oxo groups as substituents, in one embodiment not more than two such oxo substituents are present, and in another embodiment not more than one such oxo substituent is present. In one embodiment, the number of optional substituents on Het$^1$ is 1, 2, 3, 4 or 5, in another embodiment 1, 2, 3 or 4, in another embodiment 1, 2 or 3, in another embodiment 1 or 2, in another embodiment 1, in another embodiment Het$^1$ is unsubstituted. Het$^1$ can be bonded via any suitable ring carbon atom or ring nitrogen atom. In one embodiment, Het$^1$ is bonded via a ring carbon atom. In another embodiment Het$^1$ is bonded via a ring nitrogen atom. Het$^1$ can be 4-membered, 5-membered, 6-membered or 7-membered. In one embodiment, Het$^1$ is 4-membered or 5-membered, in another embodiment 5-membered to 7-membered, in another embodiment 5-membered or 6-membered, in another embodiment 5-membered, in another embodiment 6-membered. Examples of Het$^1$, from any one or more of which Het$^1$ is chosen in one embodiment, are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, [1,3]dioxolanyl including [1,3]dioxolan-2-yl and [1,3]dioxolan-4-yl, [1,4]dioxanyl including [1,4]dioxan-2-yl, thietanyl including thietan-2-yl and thietan-3-yl, tetrahydrothiophenyl including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, [1,4]dithianyl including [1,4]dithian-2-yl, azetidinyl including azetidin-1-yl, azetidin-2-yl and azetidin-3-yl, pyrrolidinyl including pyrrolidin-1-yl, pyrrolidinyl-2-yl and pyrrolidinyl-3-yl, piperidinyl including piperidin-1-yl, piperidinyl-2-yl, piperidinyl-3-yl and piperidinyl-4-yl, azepanyl including azepan-1-yl, azepan-2-yl, azepan-3-yl and azepan-4-yl, imidazolidinyl including imidazolidin-1-yl, imidazolidin-2-yl and imidazolidin-4-yl, oxazolidinyl including oxazolidin-2- yl, oxazolidin-3-yl, oxazolidin-4-yl and oxazolidin-5-yl, thiazolidinyl including thiazolidin-2-yl, thiazolidin-3-yl, thiazolidin-4-yl and thiazolidin-5-yl, piperazinyl including piperazin-1-yl and piperazin-2-yl, morpholinyl including morpholin-2-yl, morpholin-3-yl and morpholin-4-yl, thiomorpholinyl including thiomorpholin-2-yl, thiomorpholin-3-yl and thiomorpholin-4-yl, which all are optionally substituted as specified with respect to $Het^1$.

In one embodiment of the invention, the additional ring heteroatom which is optionally present in $Het^2$ besides the ring nitrogen atom via which $Het^2$ is bonded, is chosen from N and O, in another embodiment from O and S, in another embodiment it is an O atom, in another embodiment it is an N atom. In one embodiment, no additional ring heteroatom is present in $Het^2$ besides the ring nitrogen atom via which $Het^2$ is bonded. In one embodiment, two ring heteroatoms are not present in adjacent ring positions of $Het^2$. An additional ring nitrogen atom, which is present in $Het^2$ besides the ring nitrogen atom via which $Het^2$ is bonded, carries a hydrogen atom or a substituent as specified. In one embodiment, the optional substituent on such an additional ring nitrogen atom in $Het^2$ is chosen from $(C_1-C_4)$-alkyl and $(C_1-C_6)$-alkyl-O—C(O)—, in another embodiment from $(C_1-C_6)$-alkyl-O—C(O)— and $(C_3-C_7)$-cycloalkyl-$C_vH_{2v}$—O—C(O)—, in another embodiment from $(C_1-C_4)$-alkyl, in another embodiment from $(C_1-C_6)$-alkyl-O—C(O)—. In one embodiment, optional substituents on ring carbon atoms in $Het^2$ are chosen from fluorine and $(C_1-C_4)$-alkyl, in another embodiment from $(C_1-C_4)$-alkyl and oxo, in another embodiment from $(C_1-C_4)$-alkyl. In case $Het^2$ contains any oxo groups as substituents, in one embodiment not more than two such oxo substituents are present, and in another embodiment not more than one such oxo substituent is present. In one embodiment, the number of optional substituents on $Het^2$ is 1, 2, 3, 4 or 5, in another embodiment 1, 2, 3 or 4, in another embodiment 1, 2 or 3, in another embodiment 1 or 2, in another embodiment 1, in another embodiment $Het^2$ is unsubstituted. $Het^2$ can be 4-membered, 5-membered, 6-membered or 7-membered. In one embodiment, $Het^2$ is 4-membered or 5-membered, in another embodiment 5-membered to 7-membered, in another embodiment 5-membered or 6-membered, in another embodiment 5-membered, in another embodiment 6-membered. Examples of $Het^2$, from any one or more of which $Het^2$ is chosen in one embodiment, are azetidin-1-yl, pyrrolidin-1-yl, piperidin-1-yl, azepan-1-yl, imidazolidin-1-yl, oxazolidin-3-yl, thiazolidin-3-yl, piperazin-1-yl, morpholin-4-yl, thiomorpholin-4-yl, which all are optionally substituted as specified with respect to $Het^2$.

Halogen is fluorine, chlorine, bromine or iodine. In one embodiment of the invention, halogen is fluorine, chlorine or bromine, in another embodiment fluorine or chlorine, where all occurrences of halogen in the compounds of the formulae Ia and Ib are independent of each other.

The present invention comprises all stereoisomeric forms of the compounds of the formulae Ia and Ib, for example all possible enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formulae Ia and Ib, for example in unsubstituted or substituted alkyl groups or in the diazacycloalkane ring depicted in formulae Ia and Ib, can all independently of one another have S configuration or R configuration. The invention relates to enantiomers, both the levorotatory and the dextrorotatory antipode, in enantiomerically pure form and substantially enantiomerically pure form and in the form of racemates and in the form of mixtures of the two enantiomers in all ratios. The invention likewise relates to diastereomers in the form of pure and substantially pure diastereomers and in the form of mixtures of two or more diastereomers in all ratios. The invention also comprises all cis/trans isomers of the compounds of the formulae Ia and Ib in pure form and substantially pure form and in the form of mixtures of the cis isomer and the trans isomer in all ratios. Cis/trans isomerism can occur in substituted cycloalkane rings and in the diazacycloalkane ring depicted in formulae Ia and Ib, for example. The preparation of individual stereoisomers, if desired, can be carried out by resolution of a mixture according to customary methods, for example by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formula Ia or Ib or at the stage of an intermediate in the course of the synthesis. The invention also comprises all tautomeric forms of the compounds of the formulae Ia and Ib.

In case the compounds of the formulae Ia and Ib contain one or more acidic and/or basic groups, i.e. salt-forming groups, the invention also includes their corresponding physiologically or toxicologically acceptable salts, i.e. non-toxic salts, in particular their pharmaceutically acceptable salts. The salts can contain inorganic or organic salt components. Salts can be formed, for example, from compounds of the formulae Ia and Ib which contain an acidic group, for example a carboxylic acid group (HO—CO—), and non-toxic inorganic or organic bases. Suitable bases are, for example, alkaline metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the formulae Ia and Ib with bases for the preparation of the salts are in general carried out according to customary procedures in a solvent or diluent. On account of the physiological and chemical stability, advantageous salts of acidic groups are in many cases sodium, potassium, magnesium or calcium salts or ammonium salts which can also carry one or more organic groups on the nitrogen atom. Compounds of the formulae Ia and Ib which contain a basic, i.e. protonatable, group, for example an amino group, the diazacycloalkane moiety depicted in formulae Ia and Ib in case $R^{10}$ is hydrogen, or another basic heterocycle such as the 6-membered ring in the (aza)indolizine moiety in case Y is a nitrogen atom, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the formulae Ia and Ib by reaction with an acid in a solvent or diluent according to customary procedures. As usual, in particular in the case of acid addition salts of a compound containing two or more basic groups, in an obtained salt the ratio of the salt components can deviate upward or downward from the stoichiometric ratio, such as the molar ratio 1:1 or 1:2 in the case of the acid addition salt of a compound of the formula Ia or Ib containing one or two basic groups with a monovalent acid, and vary depending on the applied conditions. The present invention comprises also salts containing the components in a non-stoichiometric ratio, and an indication that an acid addition salt of a compound of the formula Ia or Ib contains an acid in a twofold molar amount, for example, also allows for a lower or higher amount of acid in the obtained salt, for example about 1.8 or about 2.1 mol of acid per mol of compound of the formula Ia or Ib. If a compound of the formula Ia or Ib simultaneously contains an acidic and a basic group in the molecule, the invention also includes internal salts (betaines, zwitterions) in addition to the salt forms mentioned. The present invention also comprises all salts of the compounds of the formulae Ia and Ib which, because of low physiological tolerability, are not directly suitable for use as a pharmaceutical, but are suitable as intermediates for chemical reactions or for the preparation of physiologically acceptable salts, for example by means of anion exchange or cation exchange. A subject of the present invention also are solvates of the compounds of the formulae Ia and Ib and their salts, such as hydrates and adducts with alcohols like $(C_1-C_4)$-alkanols, in particular physiologically acceptable solvates, as well as active metabolites of compounds of the formulae Ia and Ib and prodrugs of the compounds of the formulae Ia and Ib, i.e. compounds which in vitro may not necessarily exhibit pharmacological activity but which in vivo are converted into pharmacologically active compounds of the formula Ia or Ib, for example compounds which are converted by metabolic hydrolysis into compounds of the formula Ia or Ib. Examples of such prodrugs are compounds in which an acylatable nitrogen atom, for example the nitrogen atom carrying the group $R^{10}$ in the diazacycloalkane moiety depicted in formulae Ia and Ib in case $R^{10}$ is hydrogen, carries an alkyl-O—CO— group or an acyl group such as an alkyl-CO— group, for example, and thus has been converted into a carbamate group or an amide group, or compounds in which a carboxylic acid group has been esterified.

If the two groups $R^a$ together are a divalent $(C_2-C_5)$-alkyl group, in one embodiment of the invention the said divalent alkyl group is bonded to the carbon atom carrying the groups $R^a$ via two distinct carbon atoms and forms, together with the carbon atom carrying the groups $R^a$, a cycloalkane ring to which the (aza)indolizine ring depicted in formulae Ia and Ib and the group $R^{20}$ are bonded in the same ring position. The said cycloalkane ring, like a cycloalkane ring in the compounds of the formulae Ia and Ib in general, can carry one or more $(C_1-C_4)$-alkyl groups, for example one, two, three or four methyl groups, and/or one or more, for example one, two, three or four fluorine atoms. The said cycloalkane ring can be a cyclopropane, cyclobutane, cyclopentane or cyclohexane ring which can all be unsubstituted or substituted by alkyl and/or fluorine as indicated. In one embodiment of the invention the said cycloalkane ring is a cyclopropane ring which can be unsubstituted or substituted by alkyl and/or fluorine as indicated, i.e., in this embodiment the divalent $(C_2-C_5)$-alkyl group is an ethane-1,2-diyl group (1,2-ethylene group) which is unsubstituted or substituted by alkyl and/or fluorine as indicated. In one embodiment, the divalent $(C_2-C_5)$-alkyl group is a $(C_2-C_4)$-alkyl group, in another embodiment a $(C_2-C_3)$-alkyl group, in another embodiment a $C_2$-alkyl group. In one embodiment of the invention, the groups $R^a$ are chosen from hydrogen and fluorine, in another embodiment from hydrogen and $(C_1-C_4)$-alkyl, wherein the two groups $R^a$ are independent of each other and can be identical or different, or in all these embodiments the two groups $R^a$ together are a divalent $(C_2-C_5)$-alkyl group. In one embodiment of the invention the groups $R^a$ are identical or different groups chosen from hydrogen and fluorine, in another embodiment they are identical and different groups chosen from hydrogen and $(C_1-C_4)$-alkyl. In another embodiment of the invention the groups $R^a$ are identical and chosen from hydrogen, fluorine and $(C_1-C_4)$-alkyl, or the two groups $R^a$ together are a divalent $(C_2-C_5)$-alkyl group. In another embodiment of the invention the groups $R^a$ both are hydrogen or the two groups $R^a$ together are a divalent $(C_2-C_5)$-alkyl group. In another embodiment of the invention, the groups $R^a$ both are hydrogen, i.e. the group $C(R^a)_2$ is the group $CH_2$. In one embodiment, a $(C_1-C_4)$-alkyl group representing $R^a$ is a $(C_1-C_2)$-alkyl group, in another embodiment it is a methyl group.

In one embodiment of the invention, one, two, three or four of the groups R, in another embodiment one, two or three of the groups R, in another embodiment one or two of the groups R, in another embodiment one of the groups R, which are present in the diazacycloalkane moiety depicted in formulae Ia and Ib, are defined as above or below and are chosen from all denotations comprised by the respective definition of R including hydrogen, and all other groups R are hydrogen, where all groups R which are not hydrogen, are independent of each other and can be identical or different. In one embodiment of the invention, all groups R are hydrogen and the diazacycloalkane moiety depicted in formulae Ia and Ib is a piperazine ring, homopiperazine ring or 1,5-diazocane ring which carries the group $R^{10}$ but is not substituted by any substituents on ring carbon atoms. In another embodiment, all groups R are hydrogen and the diazacycloalkane moiety depicted in formulae Ia and Ib is a piperazine ring which carries the group $R^{10}$ but is not substituted by any substituents on ring carbon atoms. Groups R which are different from hydrogen can be present in any positions of the diazacycloalkane moiety. For example, in case one group R is present which is different from hydrogen, in one embodiment this group R is present on a ring carbon atom which is adjacent to the ring nitrogen atom which carries the group $R^{10}$, in another embodiment this group R is present on a ring a carbon atom which is adjacent to the ring nitrogen atom which does not carry the group $R^{10}$, and in another embodiment, which applies to the case that at least one of the numbers p and q is 3, this group R is present on a carbon atom which is not adjacent to any ring nitrogen. In case two groups R are present which are different from hydrogen, in one embodiment these two groups R are present on one and the same ring carbon atom which is adjacent to the ring nitrogen atom which carries the group $R^{10}$, in another embodiment one of these two groups R is present on each of the two ring carbon atoms which are adjacent to the ring nitrogen atom which carries the group $R^{10}$, in another embodiment these two groups R are present on one and the same ring carbon which is adjacent to the ring nitrogen atom which does not carry the group $R^{10}$, in another embodiment one of these two groups R is present on each of the two ring carbon atoms which are adjacent to the ring nitrogen atom which does not carry the group $R^{10}$, in another embodiment one of these two groups R is present on a ring carbon atom which is adjacent to the ring nitrogen atom which carries the group $R^{10}$ and the other group R is present on a ring carbon atom adjacent to the ring nitrogen atom which does not carry the group $R^{10}$, wherein in this latter embodiment the two ring carbon atoms carrying the said groups R can be present on the same side of the diazacycloalkane moiety, either in the chain $(C(R)_2)_p$ or in the chain $(C(R)_2)_q$, or on different sides of the diazacycloalkane moiety, one being present in the chain $(C(R)_2)_p$ and the other in the chain $(C(R)_2)_q$.

In one embodiment of the invention the groups R are chosen from hydrogen, $(C_1-C_6)$-alkyl which is optionally substituted by one or more identical or different substituents $R^1$, and $(C_3-C_7)$-cycloalkyl, wherein all groups R are independent of each other and can be identical or different. In another embodiment, the groups R are chosen from hydrogen and $(C_1-C_6)$-alkyl which is optionally substituted by one or more identical or different substituents $R^1$, wherein all groups R are independent of each other and can be identical or different, or two groups R bonded to the same carbon atom together are a divalent ($C_2$-$C_5$)-alkyl group. In another embodiment, the groups R are chosen from hydrogen and ($C_1$-$C_6$)-alkyl which is optionally substituted by one or more identical or different substituents $R^1$, wherein all groups R are independent of each other and can be identical or different. In one embodiment of the invention, an optionally substituted ($C_1$-$C_6$)-alkyl group representing R is an optionally substituted ($C_1$-$C_4$)-alkyl group, in another embodiment an optionally substituted ($C_1$-$C_2$)-alkyl group, in another embodiment an optionally substituted methyl group. If two groups R together are a divalent ($C_2$-$C_5$)-alkyl group, in one embodiment of the invention the said divalent alkyl group is bonded to the carbon atom carrying the groups R via two distinct carbon atoms and forms, together with the carbon atom carrying the groups R, a spiro-fused cycloalkane ring. The said cycloalkane ring, like a cycloalkane ring in the compounds of the formulae Ia and Ib in general, can carry one or more ($C_1$-$C_4$)-alkyl groups, for example one, two, three or four methyl groups, and/or one or more, for example one, two, three or four fluorine atoms. The said cycloalkane ring can be a cyclopropane, cyclobutane, cyclopentane or cyclohexane ring which can all be unsubstituted or substituted by alkyl and/or fluorine as indicated. In one embodiment of the invention the said cycloalkane ring is a cyclopropane ring which can be unsubstituted or substituted by alkyl and/or fluorine as indicated, i.e., in this embodiment the divalent ($C_2$-$C_5$)-alkyl group is an ethane-1,2-diyl group (1,2-ethylene group) which is unsubstituted or substituted by alkyl and/or fluorine as indicated. In one embodiment, the divalent ($C_2$-$C_5$)-alkyl group is a ($C_2$-$C_4$)-alkyl group, in another embodiment a ($C_2$-$C_3$)-alkyl group, in another embodiment a $C_2$-alkyl group.

In one embodiment of the invention, an alkyl group representing R is optionally substituted by one, two, three or four identical or different substituents $R^1$, in another embodiment by one, two or three identical or different substituents $R^1$, in another embodiment by one or two identical or different substituents $R^1$, in another embodiment by one substituent $R^1$, and in another embodiment an alkyl group representing R is unsubstituted, wherein all alkyl groups representing R are independent of each other with respect to their substitution pattern. In one embodiment, $R^1$ is chosen from ($C_3$-$C_7$)-cycloalkyl, phenyl, heteroaryl, hydroxy, $R^2$—N($R^3$)—C(O)—, $R^4$—O—C(O)— and cyano, in another embodiment from phenyl, heteroaryl, hydroxy, $R^2$—N($R^3$)—C(O)—, $R^4$—O—C(O)— and cyano, in another embodiment from phenyl, hydroxy, $R^2$—N($R^3$)—C(O)— and $R^4$—O—C(O)—, in another embodiment from phenyl, hydroxy and $R^2$—N($R^3$)—C(O)—, in another embodiment from hydroxy, $R^2$—N($R^3$)—C(O)— and $R^4$—O—C(O)—, in another embodiment from hydroxy and $R^2$—N($R^3$)—C(O)—, in another embodiment from $R^2$—N($R^3$)—C(O)— and $R^4$—O—C(O)—, and in another embodiment $R^1$ is $R^2$—N($R^3$)—C(O)—.

In one embodiment of the invention the groups $R^2$ are chosen from hydrogen and ($C_1$-$C_6$)-alkyl which is optionally substituted by one or more identical or different substituents $R^5$, in another embodiment the groups $R^2$ are chosen from ($C_1$-$C_6$)-alkyl which is optionally substituted by one or more identical or different substituents $R^5$, and ($C_3$-$C_7$)-cycloalkyl, and in another embodiment the groups $R^2$ are ($C_1$-$C_6$)-alkyl which is optionally substituted by one or more identical or different substituents $R^5$, wherein all groups $R^2$ are independent of each other and can be identical or different. In one embodiment, an optionally substituted ($C_1$-$C_6$)-alkyl group representing $R^2$ is an optionally substituted ($C_2$-$C_6$)-alkyl group, in another embodiment an optionally substituted ($C_1$-$C_4$)-alkyl group, in another embodiment an optionally substituted ($C_2$-$C_4$)-alkyl group. In one embodiment, an alkyl group representing $R^2$ is optionally substituted by one, two, three or four identical or different substituents $R^5$, in another embodiment by one, two or three identical or different substituents $R^5$, in another embodiment by one or two identical or different substituents $R^5$, in another embodiment by one substituent $R^5$, and in another embodiment an alkyl group representing $R^2$ is unsubstituted, wherein all alkyl groups representing $R^2$ are independent of each other with respect to their substitution pattern.

In one embodiment of the invention, $R^3$ is chosen from hydrogen and ($C_1$-$C_2$)-alkyl, in another embodiment from hydrogen and methyl, in another embodiment $R^3$ is ($C_1$-$C_4$)-alkyl, in another embodiment $R^3$ is hydrogen.

In one embodiment of the invention, $R^4$ is chosen from hydrogen and ($C_1$-$C_3$)-alkyl, in another embodiment $R^4$ is ($C_1$-$C_4$)-alkyl, in another embodiment $R^4$ is ($C_1$-$C_3$)-alkyl, in another embodiment $R^4$ is hydrogen.

in one embodiment of the invention, $R^5$ is chosen from hydroxy, ($C_1$-$C_4$)-alkyl-O—, ($C_1$-$C_4$)-alkyl-S(O)$_m$—, $R^6$—N($R^7$)—C(O)—, $R^8$—O—C(O)—, ($C_3$-$C_7$)-cycloalkyl, heteroaryl and Het$^1$, in another embodiment from hydroxy, ($C_1$-$C_4$)-alkyl-O—, ($C_1$-$C_4$)-alkyl-S(O)$_m$—, $R^6$—N($R^7$)—C(O)—, ($C_3$-$C_7$)-cycloalkyl, heteroaryl and Het$^1$, in another embodiment from hydroxy, ($C_1$-$C_4$)-alkyl-O—, ($C_1$-$C_4$)-alkyl-S(O)$_m$—, $R^6$—N($R^7$)—C(O)—, ($C_3$-$C_7$)-cycloalkyl and Het$^1$, in another embodiment from hydroxy, ($C_1$-$C_4$)-alkyl-O—, $R^6$—N($R^7$)—C(O)—, ($C_3$-$C_7$)-cycloalkyl and Het$^1$, in another embodiment from hydroxy, ($C_1$-$C_4$)-alkyl-O—, ($C_3$-$C_7$)-cycloalkyl and Het$^1$, in another embodiment from hydroxy and ($C_1$-$C_4$)-alkyl-O—, in another embodiment from ($C_1$-$C_4$)-alkyl-O—, ($C_3$-$C_7$)-cycloalkyl and Het$^1$, in another embodiment from hydroxy, ($C_1$-$C_4$)-alkyl-O—, ($C_1$-$C_4$)-alkyl-S(O)$_m$—, $R^6$—N($R^7$)—C(O)—, $R^8$—O—C(O)—, heteroaryl and Het$^1$, in another embodiment from hydroxy, ($C_1$-$C_4$)-alkyl-O—, ($C_1$-$C_4$)-alkyl-S(O)$_m$—, $R^6$—N($R^7$)—C(O)—, heteroaryl and Het$^1$, in another embodiment from hydroxy, ($C_1$-$C_4$)-alkyl-O—, ($C_1$-$C_4$)-alkyl-S(O)$_m$—, $R^6$—N($R^7$)—C(O)— and Het$^1$, in another embodiment from hydroxy, ($C_1$-$C_4$)-alkyl-O—, $R^6$—N($R^7$)—C(O)— and Het$^1$, in another embodiment from hydroxy, ($C_1$-$C_4$)-alkyl-O— and Het$^1$, in another embodiment from hydroxy, ($C_1$-$C_4$)-alkyl-O— and ($C_1$-$C_4$)-alkyl-S(O)$_m$—, and in another embodiment from ($C_1$-$C_4$)-alkyl-O— and Het$^1$, in another embodiment $R^5$ is ($C_1$-$C_4$)-alkyl-O—, in another embodiment $R^5$ is Het$^1$, in another embodiment $R^5$ is hydroxy, in another embodiment $R^5$ is $R^6$—N($R^7$)—C(O)—. In one embodiment, a group heteroaryl representing $R^5$ is a pyridinyl group. In one embodiment, a group Het$^1$ representing $R^5$ comprises one or two ring heteroatoms one of which is an oxygen atom and the other of which, which is optionally present, is chosen from oxygen and nitrogen, in another embodiment it comprises one ring heteroatom which is an oxygen atom and optionally one further ring heteroatom which is a nitrogen atom, in another embodiment it comprises one ring heteroatom which is an oxygen atom, and in another embodiment a group Het$^1$ representing $R^5$ is a tetrahydropyranyl group.

In one embodiment of the invention, $R^6$ is chosen from hydrogen and ($C_1$-$C_2$)-alkyl, in another embodiment from hydrogen and methyl, in another embodiment $R^6$ is ($C_1$-$C_4$)-alkyl, in another embodiment $R^6$ is hydrogen.

In one embodiment of the invention, $R^7$ is chosen from hydrogen and ($C_1$-$C_2$)-alkyl, in another embodiment from hydrogen and methyl, in another embodiment $R^7$ is ($C_1$-$C_4$)-alkyl, in another embodiment $R^7$ is hydrogen.

In one embodiment of the invention, $R^8$ is chosen from hydrogen and $(C_1-C_3)$-alkyl, in another embodiment $R^8$ is $(C_1-C_4)$-alkyl, in another embodiment $R^8$ is $(C_1-C_3)$-alkyl, in another embodiment $R^8$ is hydrogen.

In one embodiment of the invention, $R^{10}$ is chosen from hydrogen and $(C_1-C_6)$-alkyl-O—CO—, in another embodiment from hydrogen and $(C_1-C_4)$-alkyl-O—CO—, in another embodiment $R^{10}$ is hydrogen.

In one embodiment of the invention, $R^{20}$ is chosen from phenyl and heteroaryl wherein heteroaryl is chosen from thiophenyl, thiazolyl and pyridinyl, in another embodiment from phenyl and heteroaryl wherein heteroaryl is chosen from thiophenyl and pyridinyl, in another embodiment from phenyl and heteroaryl wherein heteroaryl is thiophenyl, in another embodiment from phenyl and heteroaryl wherein heteroaryl is pyridinyl, which are all optionally substituted as indicated. In another embodiment of the invention, $R^{20}$ is phenyl which is optionally substituted as indicated. In one embodiment, the number of optional substituents in the group $R^{20}$ is one, two, three or four, in another embodiment one, two or three, in another embodiment one or two, in another embodiment one. The substituents in a substituted group $R^{20}$ can be present on carbon atoms in any positions as indicated above with respect to substituted phenyl and heteroaryl groups in general. Thus, for example, in the case of a monosubstituted phenyl group representing $R^{20}$, the substituent can be present in the 2-position, the 3-position or the 4-position, and in the case of a disubstituted phenyl group the substituents can be present in positions 2 and 3, or positions 2 and 4, or positions 2 and 5, or positions 2 and 6, or positions 3 and 4, or positions 3 and 5. Likewise, a trisubstituted phenyl group representing $R^{20}$ can carry the substituents in any positions and can be a group such as 3-chloro-2,6-dimethyl-phenyl, 3-fluoro-2,6-dimethyl-phenyl, 6-chloro-3-fluoro-2-methyl-phenyl or 2-chloro-3-fluoro-6-methyl-phenyl, for example, in case of a phenyl group trisubstituted by fluorine and/or chlorine and methyl. In one embodiment, the substituents which can be present in the group $R^{20}$, are chosen from halogen, $(C_1-C_4)$-alkyl, $(C_1-C_4)$-alkyl-O— and $(C_1-C_4)$-alkyl-$S(O)_m$—, in another embodiment from halogen, $(C_1-C_4)$-alkyl and $(C_1-C_4)$-alkyl-O—, in another embodiment from halogen and $(C_1-C_4)$-alkyl, for example from chlorine, fluorine and methyl, wherein in one embodiment of the invention the alkyl groups in substituents in the group $R^{20}$ can be unsubstituted or substituted by one or more fluorine atoms and, as an example of substituents containing fluorine-substituted alkyl, the substituents comprising the group trifluoromethyl such as $CF_3$ itself, $CF_3$—O— or $CF_3$—S— may be included in each list of substituents in addition to substituents comprising unsubstituted alkyl, and in another embodiment of the invention the alkyl groups in substituents in the group $R^{20}$ are not substituted by fluorine and in this latter embodiment the said alkyl thus means unsubstituted alkyl. Specific groups in addition to the afore-mentioned specific groups, which can represent the group $R^{20}$ and from any one or more of which $R^{20}$ is chosen in one embodiment of the invention, include phenyl, i.e. unsubstituted phenyl, 2-fluoro-phenyl, 3-fluoro-phenyl, 4-fluoro-phenyl, 2-chloro-phenyl, 3-chloro-phenyl, 4-chloro-phenyl, 2-methyl-phenyl (o-tolyl), 3-methyl-phenyl (m-tolyl), 4-methyl-phenyl (p-tolyl), 2-ethyl-phenyl, 3-ethyl-phenyl, 4-ethyl-phenyl, 2-methoxy-phenyl, 3-methoxy-phenyl, 4-methoxy-phenyl, 2,3-difluoro-phenyl, 2,4-difluoro-phenyl, 2,5-difluoro-phenyl, 2,6-difluoro-phenyl, 3,4-difluoro-phenyl, 3,5-difluoro-phenyl, 2,3-dichloro-phenyl, 2,4-dichloro-phenyl, 2,5-dichloro-phenyl, 2,6-dichloro-phenyl, 3,4-dichloro-phenyl, 3,5-dichloro-phenyl, 2-chloro-3-fluoro-phenyl, 2-chloro-4-fluoro-phenyl, 2-chloro-5-fluoro-phenyl, 2-chloro-6-fluoro-phenyl, 3-chloro-2-fluoro-phenyl, 3-chloro-4-fluoro-phenyl, 3-chloro-5-fluoro-phenyl, 4-chloro-2-fluoro-phenyl, 4-chloro-3-fluoro-phenyl, 5-chloro-2-fluoro-phenyl, 2,3-dimethyl-phenyl, 2,4-dimethyl-phenyl, 2,5-dimethyl-phenyl, 2,6-dimethyl-phenyl, 3,4-dimethyl-phenyl, 3,5-dimethyl-phenyl, 2-fluoro-3-methyl-phenyl, 2-fluoro-4-methyl-phenyl, 2-fluoro-5-methyl-phenyl, 2-fluoro-6-methyl-phenyl, 3-fluoro-2-methyl-phenyl, 3-fluoro-4-methyl-phenyl, 3-fluoro-5-methyl-phenyl, 4-fluoro-2-methyl-phenyl, 4-fluoro-3-methyl-phenyl, 5-fluoro-2-methyl-phenyl, 2-chloro-3-methyl-phenyl, 2-chloro-4-methyl-phenyl, 2-chloro-5-methyl-phenyl, 2-chloro-6-methyl-phenyl, 3-chloro-2-methyl-phenyl, 3-chloro-4-methyl-phenyl, 3-chloro-5-methyl-phenyl, 4-chloro-2-methyl-phenyl, 4-chloro-3-methyl-phenyl, 5-chloro-2-methyl-phenyl, 2-methoxy-3-methyl-phenyl, 2-methoxy-4-methyl-phenyl, 2-methoxy-5-methyl-phenyl, 2-methoxy-6-methyl-phenyl, 3-methoxy-2-methyl-phenyl, 3-methoxy-4-methyl-phenyl, 3-methoxy-5-methyl-phenyl, 4-methoxy-2-methyl-phenyl, 4-methoxy-3-methyl-phenyl, 5-methoxy-2-methyl-phenyl, for example.

In one embodiment of the invention, $R^{30}$ is chosen from $(C_5-C_7)$-cycloalkyl, $(C_5-C_7)$-cycloalkenyl, tetrahydropyranyl and phenyl, in another embodiment from $(C_5-C_7)$-cycloalkyl, tetrahydropyranyl and phenyl, in another embodiment from $(C_5-C_7)$-cycloalkyl, $(C_5-C_7)$-cycloalkenyl and phenyl, in another embodiment from $(C_5-C_7)$-cycloalkyl, $(C_5-C_7)$-cycloalkenyl and tetrahydropyranyl, in another embodiment from $(C_5-C_7)$-cycloalkyl, $(C_5-C_7)$-cycloalkenyl, phenyl and heteroaryl, in another embodiment from $(C_5-C_7)$-cycloalkyl, tetrahydropyranyl, phenyl and heteroaryl, in another embodiment from $(C_5-C_7)$-cycloalkyl, phenyl and heteroaryl, in another embodiment from $(C_5-C_7)$-cycloalkyl and $(C_5-C_7)$-cycloalkenyl, in another embodiment from $(C_5-C_7)$-cycloalkyl and phenyl, in another embodiment from phenyl and heteroaryl, in another embodiment $R^{30}$ is phenyl, wherein the cycloalkyl, cycloalkenyl, phenyl and heteroaryl groups are all optionally substituted as indicated. In one embodiment, a cycloalkyl group representing $R^{30}$ is $(C_5-C_6)$-cycloalkyl, in another embodiment cyclohexyl. In one embodiment, a cycloalkenyl group representing $R^{30}$ is $(C_5-C_6)$-cycloalkenyl, in another embodiment cyclohexenyl. In one embodiment, a heteroaryl group representing $R^{30}$ is chosen from thiophenyl and pyridinyl, in another embodiment it is thiophenyl, in another embodiment it is pyridinyl, which are all optionally substituted as indicated. In one embodiment, the number of optional substituents in the group $R^{30}$ is one, two, three or four, in another embodiment one, two or three, in another embodiment one or two, in another embodiment one, and in another embodiment the group $R^{30}$ is unsubstituted. The substituents in a substituted group $R^{30}$ can be present on carbon atoms in any positions as indicated above with respect to substituted cycloalkyl, cycloalkenyl, phenyl and heteroaryl groups in general. For example, in the case of a monosubstituted phenyl group representing $R^{30}$, the substituent can be present in the 2-position, the 3-position or the 4-position, and in the case of a disubstituted phenyl group the substituents can be present in positions 2 and 3, or positions 2 and 4, or positions 2 and 5, or positions 2 and 6, or positions 3 and 4, or positions 3 and 5. In one embodiment, the substituents which can be present in a cycloalkyl or cycloalkenyl group representing $R^{30}$ are chosen from fluorine, methyl and hydroxy, in another embodiment from fluorine and methyl. In one embodiment of the invention, the substituents in a cycloalkyl or cycloalkenyl group representing $R^{30}$ are hydroxy. In another embodiment, a cycloalkyl or cycloalkenyl group representing $R^{30}$ is unsubstituted. In one embodiment, the substituents which are optionally present in a phenyl or heteroaryl group representing $R^{30}$, are chosen from halogen, $(C_1-C_4)$-alkyl and $(C_1-C_4)$-alkyl-O—, in another embodiment from halogen, $(C_1-C_4)$-alkyl and cyano, in another embodiment from halogen and $(C_1-C_4)$-alkyl, wherein in one embodiment of the invention the alkyl groups in substituents in phenyl and heteroaryl groups representing $R^{30}$ can be unsubstituted or substituted by one or more fluorine atoms and, as an example of substituents containing fluorine-substituted alkyl, the substituents comprising the group trifluoromethyl such as $CF_3$ itself or $CF_3$—O— may be included in each list of substituents in addition to substituents comprising unsubstituted alkyl, and in another embodiment of the invention the alkyl groups in substituents in the group $R^{30}$ are not substituted by fluorine and in this latter embodiment the said alkyl thus means unsubstituted alkyl. In one embodiment of the invention, the substituents which are optionally present in a phenyl or heteroaryl group representing $R^{30}$, are chosen from halogen, in another embodiment from fluorine, chlorine and bromine, in another embodiment from fluorine and chlorine. Specific groups which can occur as the group $R^{30}$ and from any one or more of which $R^{30}$ is chosen in one embodiment of the invention, include cyclopentyl, cyclohexyl, cycloheptyl, cyclopent-2-enyl, cyclohex-2-enyl, cyclohept-2-enyl, 4-fluoro-cyclohexyl, 4-methyl-cyclohexyl, 2-hydroxy-cyclopentyl, 3-hydroxy-cyclopentyl, 2-hydroxy-cyclohexyl, 3-hydroxy-cyclohexyl, 4-hydroxy-cyclohexyl, 2-hydroxy-cycloheptyl, 3-hydroxy-cycloheptyl, 4-hydroxy-cycloheptyl, 4,4-difluoro-cyclohexyl, 3,3-dimethyl-cyclohexyl, 4,4-dimethyl-cyclohexyl, tetrahydropyran-3-yl, tetrahydropyran-4-yl, phenyl, i.e. unsubstituted phenyl, 2-fluoro-phenyl, 3-fluoro-phenyl, 4-fluoro-phenyl, 2-chloro-phenyl, 3-chloro-phenyl, 4-chloro-phenyl, 3-bromo-phenyl, 4-bromo-phenyl, 2-methyl-phenyl, 3-methyl-phenyl, 4-methyl-phenyl, 2-methoxy-phenyl, 3-methoxy-phenyl, 4-methoxy-phenyl, thiophen-2-yl, thiophen-3-yl, pyridin-2-yl, pyridin-3-yl, pyridin-4-yl, 2-methoxy-pyridin-3-yl, 4-methoxy-pyridin-3-yl, 5-methoxy-pyridin-3-yl, 6-methoxy-pyridin-3-yl, 2-methoxy-pyridin-4-yl, 3-methoxy-pyridin-4-yl, for example.

The substituents $R^{40}$ can be present on ring carbon atoms in any of the positions in the 6-membered ring of the (aza) indolizine moiety depicted in formulae Ia and Ib, which is not occupied by the group Y and is not a fusion position. In case the number n of the substituents $R^{40}$ is less than 3, all carbon atoms in the said positions of the 6-membered ring of the (aza)indolizine moiety depicted in formulae Ia and Ib, which are not occupied by the group Y or are a fusion position, which do not carry a substituent $R^{40}$, carry a hydrogen atom, i.e., in the respective positions CH groups are present. In case the number n is 0, all three of such ring carbon atoms carry hydrogen atoms. In the case of a compound of the formula Ia or Ib which carries one substituent $R^{40}$, in one embodiment of the invention the substituent $R^{40}$ is present on the ring carbon atom in the 6-membered ring in the (aza)indolizine moiety depicted in formulae Ia and Ib which is adjacent to the group Y, in another embodiment the substituent $R^{40}$ is present on the ring carbon atom which is separated from the group Y by one ring carbon atom, and in another embodiment the substituent $R^{40}$ is present on the ring carbon atom which is separated from the group Y by two ring carbon atoms. In the case of a compound of the formula Ia or Ib which carries two substituents $R^{40}$, in one embodiment the substituents $R^{40}$ are present on the ring carbon atom which is adjacent to the group Y and on the ring carbon atom which is separated from the group Y by one ring carbon atom, in another embodiment the substituents $R^{40}$ are present on the ring carbon atom which is adjacent to the group Y and on the ring carbon atom which is separated from the group Y by two ring carbon atoms, and in another embodiment the substituents $R^{40}$ are present on the ring carbon atom which is separated from the group Y by one ring carbon atom and on the ring carbon atom which is separated from the group Y by two ring carbon atoms. In one embodiment of the invention, the number n of the substituents $R^{40}$ is 0, 1 or 2, in another embodiment it is 0 or 1. In one embodiment of the invention the number n is 1 or 2, in another embodiment it is 1. In another embodiment the number n is 0, i.e. no substituent $R^{40}$ is present in the compound of the formula Ia or Ib. In one embodiment of the invention, $R^{40}$ is chosen from halogen, $(C_1-C_4)$-alkyl, hydroxy, $(C_1-C_4)$-alkyl-O—, $R^{41}$—$N(R^{42})$—, $Het^2$, $R^{41}$—$N(R^{42})$—C(O)—, $Het^2$-C(O)—, cyano, $R^{41}$—$N(R^{42})$—$S(O)_2$— and $Het^2$-$S(O)_2$—, in another embodiment from halogen, $(C_1-C_4)$-alkyl, hydroxy, $(C_1-C_4)$-alkyl-O—, $(C_1-C_4)$-alkyl-$S(O)_m$—, $R^{41}$—$N(R^{42})$—, $Het^2$, $R^{41}$—$N(R^{42})$—C(O)—, $Het^2$-C(O)—, $R^{41}$—$N(R^{42})$—$S(O)_2$— and $Het^2$-$S(O)_2$—, in another embodiment from halogen, $(C_1-C_4)$-alkyl, hydroxy, $(C_1-C_4)$-alkyl-O—, $(C_1-C_4)$-alkyl-$S(O)_m$—, $Het^2$, $R^{41}$—$N(R^{42})$—C(O)—, $Het^2$-C(O)—, $R^{41}$—$N(R^{42})$—$S(O)_2$— and $Het^2$—$S(O)_2$—, in another embodiment from halogen, $(C_1-C_4)$-alkyl, hydroxy, $(C_1-C_4)$-alkyl-O—, $(C_1-C_4)$-alkyl-$S(O)_m$—, $R^{41}$—$N(R^{42})$—C(O)—, $Het^2$-C(O)—, $R^{41}$—$N(R^{42})$—$S(O)_2$— and $Het^2$-$S(O)_2$—, in another embodiment from halogen, $(C_1-C_4)$-alkyl, hydroxy, $(C_1-C_4)$-alkyl-O—, $R^{41}$—$N(R^{42})$—, $Het^2$, $R^{41}$—$N(R^{42})$—C(O)— and $Het^2$-C(O)—, in another embodiment from halogen, $(C_1-C_4)$-alkyl, hydroxy, $(C_1-C_4)$-alkyl-O—, $R^{41}$—$N(R^{42})$—C(O)— and $Het^2$-C(O)—, in another embodiment from halogen, hydroxy, $(C_1-C_4)$-alkyl-O—, $Het^2$, $R^{41}$—$N(R^{42})$—C(O)— and $Het^2$-C(O)—, in another embodiment from halogen, hydroxy, $(C_1-C_4)$-alkyl-O—, $R^{41}$—$N(R^{42})$—C(O)— and $Het^2$-C(O)—, in another embodiment from halogen, $(C_1-C_4)$-alkyl-O—, $R^{41}$—$N(R^{42})$—C(O)— and $Het^2$-C(O)—, in another embodiment from halogen, $(C_1-C_4)$-alkyl, $R^{41}$—$N(R^{42})$—, $Het^2$, $R^{41}$—$N(R^{42})$—C(O)— and $Het^2$-C(O)—, in another embodiment from halogen, $(C_1-C_4)$-alkyl, $R^{41}$—$N(R^{42})$—C(O)— and $Het^2$-C(O)—, in another embodiment from halogen, $Het^2$, $R^{41}$—$N(R^{42})$—C(O)— and $Het^2$-C(O)—, in another embodiment from halogen, $R^{41}$—$N(R^{42})$—C(O)— and $Het^2$-C(O)—, in another embodiment from $R^{41}$—$N(R^{42})$—C(O)— and $Het^2$-C(O)—, in another embodiment from halogen and $R^{41}$—$N(R^{42})$—C(O)—, in another embodiment from halogen and $Het^2$-C(O)—, in another embodiment from halogen, hydroxy and $(C_1-C_4)$-alkyl-O—, in another embodiment from halogen and $(C_1-C_4)$-alkyl-O—, in another embodiment $R^{40}$ is $(C_1-C_4)$-alkyl-O—, in another embodiment $R^{40}$ is $R^{41}$—$N(R^{42})$—C(O)—, in another embodiment $R^{40}$ is $Het^2$-C(O), wherein all substituents $R^{40}$ are independent of each other and can be identical or different.

In one embodiment of the invention, $R^{41}$ is chosen from hydrogen and $(C_1-C_4)$-alkyl, in another embodiment from hydrogen and $(C_3-C_7)$-cycloalkyl-$C_vH_{2v}$—, in another embodiment from $(C_1-C_4)$-alkyl and $(C_3-C_7)$-cycloalkyl-$C_vH_{2v}$—, in another embodiment $R^{41}$ is $(C_1-C_4)$-alkyl, in another embodiment $R^{41}$ is hydrogen, wherein all groups $R^{41}$ are independent of each other and can be identical or different.

In one embodiment of the invention, $R^{42}$ is chosen from hydrogen and methyl, in another embodiment $R^{42}$ is $(C_1-C_4)$-alkyl, in another embodiment $R^{42}$ is hydrogen, wherein all groups $R^{42}$ are independent of each other and can be identical or different.

In one embodiment of the invention, Y is chosen from CH and C((C$_1$-C$_4$)-alkyl), in another embodiment from N, CH and C(CH$_3$), in another embodiment from N and CH, in another embodiment Y is CH, and in another embodiment Y is N. In one embodiment of the invention, the compound of the formula Ia or Ib is a compound of the formula Ia, in any of its stereoisomeric forms or a mixture of stereoisomeric forms in any ratio, or a physiologically acceptable salt thereof, or a physiologically acceptable solvate of any of them, in another embodiment it is a compound of the formula Ia in which the group Y is chosen from CH and C((C$_1$-C$_4$)-alkyl), in any of its stereoisomeric forms or a mixture of stereoisomeric forms in any ratio, or a physiologically acceptable salt thereof, or a physiologically acceptable solvate of any of them, i.e. it is an indolizine-3-carboxamide derivative which may be represented by the formula Ic, and in another embodiment it is a compound of the formula Ia in which the group Y is N, in any of its stereoisomeric forms or a mixture of stereoisomeric forms in any ratio, or a physiologically acceptable salt thereof, or a physiologically acceptable solvate of any of them, i.e. it is a 5-azaindolizine-3-carboxamide derivative, or a pyrrolo[1,2-b]pyridazine-7-carboxamide derivative, which may be represented by the formula Id.

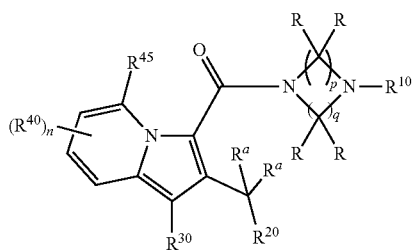

Ic

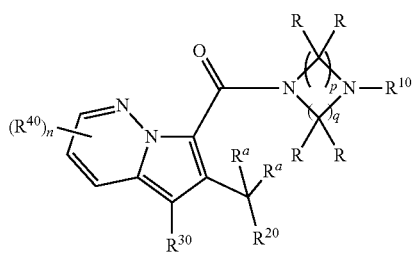

Id

In another embodiment of the invention, the compound of the formula Ia or Ib is a compound of the formula Ib, in any of its stereoisomeric forms or a mixture of stereoisomeric forms in any ratio, or a physiologically acceptable salt thereof, or a physiologically acceptable solvate of any of them, in another embodiment it is a compound of the formula Ib in which the group Y is chosen from CH and C((C$_1$-C$_4$)-alkyl), in any of its stereoisomeric forms or a mixture of stereoisomeric forms in any ratio, or a physiologically acceptable salt thereof, or a physiologically acceptable solvate of any of them, i.e. it is an indolizine-1-carboxamide derivative which may be represented by the formula Ie, and in another embodiment it is a compound of the formula Ib in which the group Y is N, in any of its stereoisomeric forms or a mixture of stereoisomeric forms in any ratio, or a physiologically acceptable salt thereof, or a physiologically acceptable solvate of any of them, i.e. it is a 5-azaindolizine-1-carboxamide derivative, or a pyrrolo[1,2-b]pyridazine-5-carboxamide derivative, which may be represented by the formula If.

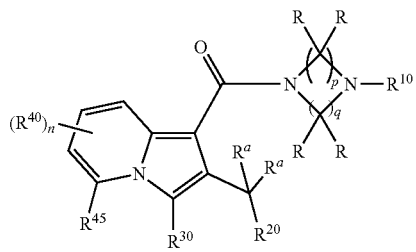

Ie

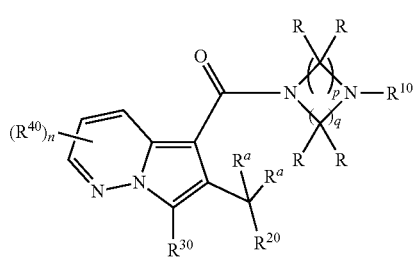

If

All statements and explanations above and below with respect to the compounds of the formulae Ia and Ib and the present invention in general apply correspondingly to the compounds of the formulae Ic, Id, Ie and If. In particular are R, R$^a$, R$^{10}$, R$^{20}$, R$^{30}$, R$^{40}$, n, p and q in the compounds of the formulae Ic, Id, Ie and If defined as in the general definition of the compounds of the formulae Ia and Ib or in any embodiment specified above or below. The group R$^{45}$ in the compounds of the formulae Ic and Ie is chosen from hydrogen and (C$_1$-C$_4$)-alkyl. In one embodiment, R$^{45}$ is chosen from hydrogen and methyl, and in another embodiment R$^{45}$ is hydrogen. In one embodiment of the invention the compound of the formula Ia or Ib is a compound of the formula Ia in which the group Y is chosen from N, CH and C((C$_1$-C$_4$)-alkyl), or a compound of the formula Ib in which the group Y is chosen from CH and C((C$_1$-C$_4$)-alkyl), in any of its stereoisomeric forms or a mixture of stereoisomeric forms in any ratio, or a physiologically acceptable salt thereof, or a physiologically acceptable solvate of any of them, i.e., in this embodiment the compounds of the formulae Ia and Ib may be represented by the formulae Ic, Id and Ie.

In one embodiment of the invention the number p is 2 and the number q is chosen from 2 and 3. In another embodiment of the invention both p and q are 2, i.e., the diazacycloalkane ring depicted in formulae Ia and Ib is a piperazine ring and the compound of the formula Ia or Ib is a compound of the formula Ig or 1 h, in any of its stereoisomeric forms or a mixture of stereoisomeric forms in any ratio, or a physiologically acceptable salt thereof, or a physiologically acceptable solvate of any of them. All statements and explanations with respect to the compounds of the formulae Ia and Ib and the present invention in general apply correspondingly to the compounds of the formulae Ig and Ih. In particular are R, R$^a$, R$^{10}$, R$^{20}$, R$^{30}$, R$^{40}$, Y and n in the compounds of the formulae Ig and 1 h defined as in the general definition of the compounds of the formulae Ia and Ib or in any embodiment specified above or below.

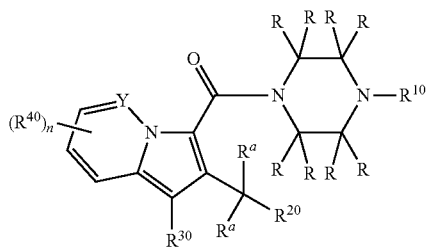

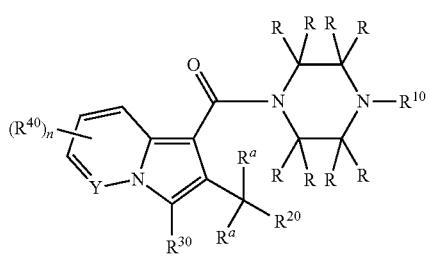

A subject of the invention are all compounds of the formulae Ia and Ib wherein any one or more structural elements such as groups, substituents and numbers are defined as in any of the specified embodiments or definitions of the elements or have any one or more of the specific meanings which are mentioned herein as examples of elements, wherein all combinations of one or more specified embodiments and/or definitions and/or specific meanings of the elements are a subject of the present invention, and wherein structural elements in the compounds of the formula Ia are defined independent from the structural elements in the compounds of the formula Ib and can be identical or different in the compounds of the two formulae. Also with respect to all such compounds of the formulae Ia and Ib, all their stereoisomeric forms and mixtures of stereoisomeric forms in any ratio, and their physiologically acceptable salts, and the physiologically acceptable solvates of any of them, are a subject of the present invention. Likewise, also with respect to all specific compounds disclosed herein, such as the example compounds which represent embodiments of the invention wherein the structural elements in the general definition of the compounds of the formulae Ia and Ib have the specific meanings present in the respective specific compound, it applies that they are a subject of the present invention in any of their stereoisomeric forms and or a mixture of stereoisomeric forms in any ratio, and in the form of their physiologically acceptable salts, and in the form of the physiologically acceptable solvates of any of them. Irrespective thereof whether a specific compound is disclosed herein as a free compound and/or as a specific salt, it is a subject of the invention both in the form of the free compound and in the form of all its physiologically acceptable salts, and if a specific salt is disclosed, additionally in the form of this specific salt, and in the form of the physiologically acceptable solvates of any of them.

As an example of compounds of the invention in which any one or more structural elements are defined as in any of the specified embodiments or definitions, compounds of the formulae Ia and Ib may be mentioned wherein p and q both are 2, $R^{10}$ is chosen from hydrogen and $(C_1-C_6)$-alkyl-O—C(O)—, and the groups $R^a$ both are hydrogen, i.e. the compounds of the formulae Ig and Ih wherein $R^{10}$ is chosen from hydrogen and $(C_1-C_6)$-alkyl-O—C(O)— and $R^a$ is hydrogen. Another example are compounds of the formulae Ia and Ib wherein p and q both are 2, one, two or three of the groups R are independently of each other chosen from hydrogen, $(C_1-C_6)$-alkyl which is optionally substituted by one, two or three identical or different substituents $R^1$, and $(C_3-C_7)$-cycloalkyl, or two of these groups R bonded to the same carbon atom together are a divalent $(C_2-C_5)$-alkyl group, and all other groups R are hydrogen, $R^{10}$ is chosen from hydrogen and $(C_1-C_6)$-alkyl-O—C(O)—, and the groups $R^a$ both are hydrogen. Another example are compounds of the formulae Ia and Ib wherein p and q both are 2, one, two or three of the groups R are independently of each other chosen from hydrogen and $(C_1-C_6)$-alkyl which is optionally substituted by one, two or three identical or different substituents $R^1$, and all other groups R are hydrogen, $R^{10}$ is hydrogen, and the groups $R^a$ both are hydrogen. All these compounds, in which all other groups and numbers are defined as in the general definition of the compounds of the formulae Ia and Ib or in any of the specified embodiments or definitions, are a subject of the invention in any of their stereoisomeric forms or a mixture of stereoisomeric forms in any ratio, and the physiologically acceptable salts thereof, and the physiologically acceptable solvates of any of them.

Another such example are compounds of the formulae Ia and Ib, in any of their stereoisomeric forms or a mixture of stereoisomeric forms in any ratio, and the physiologically acceptable salts thereof, and the physiologically acceptable solvates of any of them, wherein $R^a$ is chosen from hydrogen and fluorine;

R is chosen from hydrogen and $(C_1-C_6)$-alkyl which is optionally substituted by one or more identical or different substituents $R^1$, wherein all groups R are independent of each other and can be identical or different, or two groups R bonded to the same carbon atom together are a divalent $(C_2-C_5)$-alkyl group;

$R^1$ is chosen from phenyl, hydroxy, $(C_1-C_4)$-alkyl-O—, $R^2$—N($R^3$)—C(O)—, $R^4$—O—C(O)— and cyano;

$R^2$ is chosen from hydrogen and $(C_1-C_6)$-alkyl which is optionally substituted by one or more identical or different substituents $R^5$, wherein all groups $R^2$ are independent of each other and can be identical or different;

$R^3$, $R^4$, $R^6$, $R^7$ and $R^8$ are chosen from hydrogen and $(C_1-C_4)$-alkyl, wherein all groups $R^3$, $R^4$, $R^6$, $R^7$ and $R^8$ are independent of each other and can be identical or different;

$R^5$ is chosen from hydroxy, $(C_1-C_4)$-alkyl-O—, $(C_1-C_4)$-alkyl-S(O)$_m$—, $R^6$—N($R^7$)—C(O)—, $R^8$—O—C(O)—, cyano, $(C_3-C_7)$-cycloalkyl, phenyl, heteroaryl and Het$^1$;

$R^{10}$ is chosen from hydrogen and $(C_1-C_6)$-alkyl-O—C(O)—;

$R^{20}$ is chosen from phenyl and heteroaryl which are optionally substituted by one or more identical or different substituents chosen from halogen, $(C_1-C_4)$-alkyl, $(C_1-C_4)$-alkyl-O—, $(C_1-C_4)$-alkyl-S(O)$_m$— and cyano;

$R^{30}$ is chosen from $(C_5-C_7)$-cycloalkyl, tetrahydropyranyl, phenyl and heteroaryl, wherein cycloalkyl is optionally substituted by one or more identical or different substituents chosen from fluorine, $(C_1-C_4)$-alkyl and hydroxy, and phenyl and heteroaryl are optionally substituted by one or more identical or different substituents chosen from halogen, $(C_1-C_4)$-alkyl, $(C_1-C_4)$-alkyl-O— and cyano;

$R^{40}$ is chosen from halogen, $(C_1-C_4)$-alkyl, $(C_3-C_7)$-cycloalkyl-$C_vH_{2v}$—, hydroxy, $(C_1-C_4)$-alkyl-O—, $(C_1-C_4)$-alkyl-S(O)$_m$—, $R^{41}$—N($R^{42}$)—, Het$^2$, $R^{41}$—N($R^{42}$)—C(O)—, Het$^2$-C(O)—, cyano, $R^{41}$—N($R^{42}$)—S(O)$_2$— and Het$^2$-S(O)$_2$—, wherein all substituents $R^{40}$ are independent of each other and can be identical or different;

$R^{41}$ is chosen from hydrogen and $(C_1-C_4)$-alkyl, wherein all groups $R^{41}$ are independent of each other and can be identical or different;

$R^{42}$ is chosen from hydrogen and $(C_1-C_4)$-alkyl, wherein all groups $R^{42}$ are independent of each other and can be identical or different;

Y is chosen from N, CH and $C((C_1-C_4)\text{-alkyl})$;

heteroaryl is an aromatic monocyclic, 5-membered or 6-membered, heterocyclic group which comprises 1 or 2 identical or different ring heteroatoms chosen from N, O and S, wherein one of the ring nitrogen atoms can carry a hydrogen atom or a $(C_1-C_4)$-alkyl substituent, and wherein the heteroaryl group is bonded via a ring carbon atom;

$Het^1$ is a saturated, monocyclic, 4-membered to 7-membered heterocyclic group which comprises 1 or 2 identical or different ring heteroatoms chosen from N, O and S, wherein the group $Het^1$ is bonded via a ring carbon atom or a ring nitrogen atom, wherein ring nitrogen atoms can carry a hydrogen atom or a substituent chosen from $(C_1-C_4)$-alkyl and $(C_1-C_6)$-alkyl-O—C(O)—, wherein ring sulfur atoms can carry one or two oxo groups, and wherein $Het^1$ is optionally substituted on ring carbon atoms by one or more identical or different substituents chosen from fluorine, $(C_1-C_4)$-alkyl and oxo;

$Het^2$ is a saturated, monocyclic, 4-membered to 7-membered heterocyclic group which comprises a ring nitrogen atom via which the group $Het^2$ is bonded and optionally an additional ring heteroatom chosen from N, O and S, wherein the additional ring nitrogen atom carries a hydrogen atom or a substituent chosen from $(C_1-C_4)$-alkyl and $(C_1-C_6)$-alkyl-O—C(O)—, wherein the ring sulfur atom can carry one or two oxo groups, and wherein $Het^2$ is optionally substituted on ring carbon atoms by one or more identical or different substituents chosen from fluorine, $(C_1-C_4)$-alkyl and oxo;

m is chosen from 0, 1 and 2, wherein all numbers m are independent of each other and can be identical or different;

n is chosen from 0, 1 and 2;

p and q are 2;

v is chosen from 0, 1 and 2, wherein all numbers v are independent of each other and can be identical or different;

wherein all alkyl groups, independently of each other, are optionally substituted by one or more fluorine atoms;

wherein all cycloalkyl groups, independently of each other, are optionally substituted by one or more identical or different substituents chosen from fluorine and $(C_1-C_4)$-alkyl, unless specified otherwise;

wherein all phenyl and heteroaryl groups present in $R^1$ and $R^5$, independently of each other, are optionally substituted by one or more identical or different substituents chosen from halogen, $(C_1-C_4)$-alkyl, $(C_1-C_4)$-alkyl-O—, $(C_1-C_4)$-alkyl-S$(O)_2$— and cyano.

Another such example are compounds of the formulae Ia and Ib, in any of their stereoisomeric forms or a mixture of stereoisomeric forms in any ratio, and the physiologically acceptable salts thereof, and the physiologically acceptable solvates of any of them, wherein $R^a$ is hydrogen;

one or two of the groups R are independently of each other chosen from hydrogen and $(C_1-C_6)$-alkyl which is optionally substituted by one or two identical or different substituents $R^1$, and the other groups R are hydrogen;

$R^1$ is chosen from hydroxy, $R^2$—N($R^3$)—C(O)— and $R^4$—O—C(O)—;

$R^2$ is chosen from hydrogen and $(C_1-C_6)$-alkyl which is optionally substituted by one or two identical or different substituents $R^5$, wherein all groups $R^2$ are independent of each other and can be identical or different;

$R^3$, $R^4$, $R^6$, $R^7$ and $R^8$ are chosen from hydrogen and $(C_1-C_4)$-alkyl, wherein all groups $R^3$, $R^4$, $R^6$, $R^7$ and $R^8$ are independent of each other and can be identical or different;

$R^5$ is chosen from hydroxy, $(C_1-C_4)$-alkyl-O—, $(C_1-C_4)$-alkyl-S$(O)_m$—, $R^6$—N($R^7$)—C(O)—, $R^8$—O—C(O)—, heteroaryl and $Het^1$, $R^{10}$ is chosen from hydrogen and $(C_1-C_6)$-alkyl-O—C(O)—;

$R^{20}$ is phenyl which is optionally substituted by one, two or three identical or different substituents chosen from halogen and $(C_1-C_4)$-alkyl;

$R^{30}$ is phenyl which is optionally substituted by one or two identical or different substituents chosen from halogen and $(C_1-C_4)$-alkyl;

$R^{40}$ is chosen from halogen, $(C_1-C_4)$-alkyl, hydroxy, $(C_1-C_4)$-alkyl-O—, $R^{41}$—N($R^{42}$)—, $Het^2$, $R^{41}$—N($R^{42}$)—C(O)— and $Het^2$-C(O)—, wherein all substituents $R^{40}$ are independent of each other and can be identical or different;

$R^{41}$ is chosen from hydrogen and $(C_1-C_4)$-alkyl, wherein all groups $R^{41}$ are independent of each other and can be identical or different;

$R^{42}$ is chosen from hydrogen and $(C_1-C_4)$-alkyl, wherein all groups $R^{42}$ are independent of each other and can be identical or different;

Y is chosen from N, CH and $C((C_1-C_4)\text{-alkyl})$;

heteroaryl is an aromatic monocyclic, 5-membered or 6-membered, heterocyclic group which comprises 1 or 2 identical or different ring heteroatoms chosen from N, O and S, wherein one of the ring nitrogen atoms can carry a hydrogen atom or a $(C_1-C_4)$-alkyl substituent, and wherein the heteroaryl group is bonded via a ring carbon atom;

$Het^1$ is a saturated, monocyclic, 4-membered to 7-membered heterocyclic group which comprises 1 or 2 identical or different ring heteroatoms chosen from N, O and S, wherein the group $Het^1$ is bonded via a ring carbon atom or a ring nitrogen atom, wherein ring nitrogen atoms can carry a hydrogen atom or a substituent chosen from $(C_1-C_4)$-alkyl and $(C_1-C_6)$-alkyl-O—C(O)—, wherein ring sulfur atoms can carry one or two oxo groups, and wherein $Het^1$ is optionally substituted on ring carbon atoms by one or more identical or different substituents chosen from fluorine and $(C_1-C_4)$-alkyl;

$Het^2$ is a saturated, monocyclic, 4-membered to 7-membered heterocyclic group which comprises a ring nitrogen atom via which the group $Het^2$ is bonded and optionally an additional ring heteroatom chosen from N, O and S, wherein the additional ring nitrogen atom carries a hydrogen atom or a substituent chosen from $(C_1-C_4)$-alkyl and $(C_1-C_6)$-alkyl-O—C(O)—, wherein the ring sulfur atom can carry one or two oxo groups, and wherein $Het^2$ is optionally substituted on ring carbon atoms by one or more identical or different substituents chosen from fluorine and $(C_1-C_4)$-alkyl;

m is chosen from 0, 1 and 2, wherein all numbers m are independent of each other and can be identical or different;

n is chosen from 0, 1 and 2;

p and q are 2;

wherein all alkyl groups, independently of each other, are optionally substituted by one or more fluorine atoms;

wherein all heteroaryl groups present in $R^5$, independently of each other, are optionally substituted by one or more identical or different substituents chosen from halogen, $(C_1-C_4)$-alkyl, $(C_1-C_4)$-alkyl-O—, $(C_1-C_4)$-alkyl-S$(O)_2$— and cyano.

Another subject of the present invention are processes for the preparation of the compounds of the formulae Ia and Ib, including their salts and solvates, which are outlined below and by which the compounds are obtainable. For example, in one approach for the preparation of a compound of the formula Ia or Ib a compound of the formula IIa or IIb, or a compound in which instead of the carboxylic acid group depicted in formulae IIa and IIb a reactive carboxylic acid derivative group is present, for example a carboxylic acid chloride group, is reacted with a compound of the formula III to give a compound of the formula IVa or IVb, respectively,

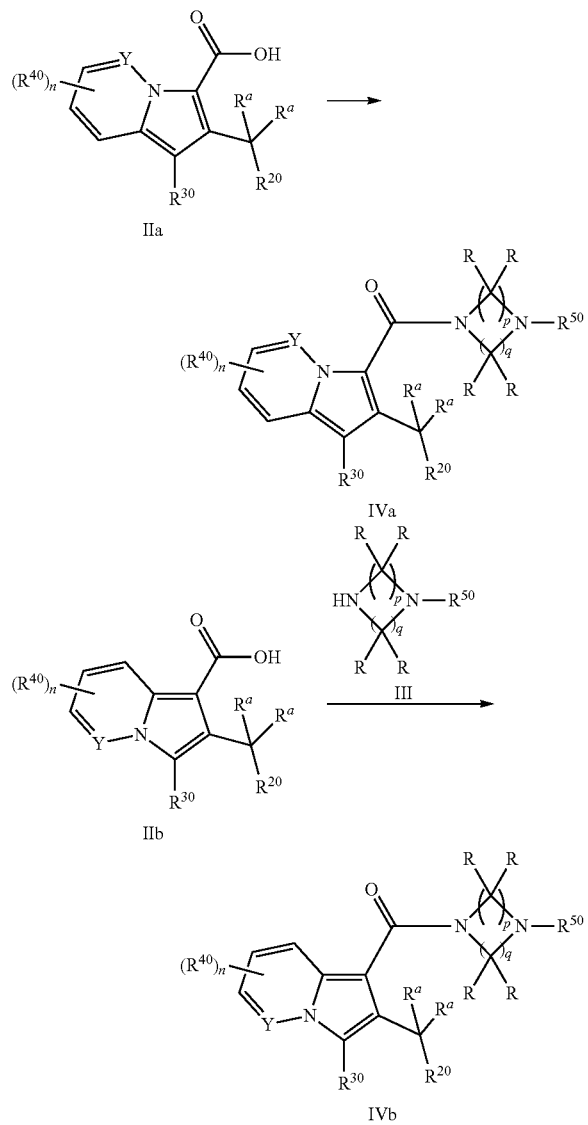

wherein R, $R^a$, $R^{20}$, $R^{30}$, $R^{40}$, Y, n, p and q in the compounds of the formulae IIa, IIb, III, IVa and IVb are defined as in the compounds of the formulae Ia and Ib and additionally functional groups can be present in protected form or in the form of a precursor group, which is later converted into the final group, and $R^{50}$ is defined as $R^{10}$ in the compounds of the formulae Ia and Ib with the exception of hydrogen, or $R^{50}$ is a protective group, and removing the protective group $R^{50}$ in the compound of the formula IVa or IVb in the case of the preparation of a compound of the formula Ia or Ib in which $R^{10}$ is hydrogen, and optionally converting any other protected groups or precursor groups into the final groups. I.e., the group $R^{50}$ in the compounds of the formulae III, IVa and IVb can be $(C_1-C_6)$-alkyl-O—CO— or $(C_3-C_7)$-cycloalkyl-$C_vH_{2v}$—O—CO—, which groups protect the nitrogen atom carrying $R^{50}$ against a reaction with the compound of the formula IIa or IIb, or $R^{50}$ can be another protective group which prevents a reaction at the said nitrogen atom and can later be removed to give a final compound of the formula Ia or Ib in which $R^{10}$ is hydrogen. Examples of groups which prevent a reaction at the said nitrogen atom, besides groups such as the tert-butyloxycarbonyl group which can later be removed by treatment with an acid such as trifluoroacetic acid or hydrogen chloride, are the benzyloxycarbonyl group and the benzyl group which can later be removed by hydrogenation in the presence of a catalyst such as a palladium catalyst, or the fluoren-9-yloxycarbonyl group which can later be removed by treatment with piperidine.

The reaction of the carboxylic acids of the formulae IIa and IIb or reactive derivatives thereof with the diazacycloalkane of the formula III to give the compounds of the formulae IVa and IVb comprises the formation of an amide bond, and can be performed under standard conditions for such amide couplings. If a carboxylic acid of the formula IIa or IIb is employed in the reaction, it is usually converted into a reactive derivative, which can be isolated or prepared in situ, or activated in situ by a customary amide coupling reagent. For example, the compound of the formula IIa or IIb can be converted into a carboxylic acid chloride by treatment with thionyl chloride, oxalyl chloride or (1-chloro-2-methyl-propenyl)-dimethylamine, into a reactive ester, or into a mixed anhydride by treatment with an alkyl chloroformate like ethyl chloroformate or isobutyl chloroformate, or it can be activated with a reagent such as propanephosphonic anhydride, an N,N'-carbonyldiazole like N,N'-carbonyldiimidazole (CDI), a carbodiimide like N,N'-diisopropylcarbodiimide (DIC), N,N'-dicyclohexylcarbodiimide (DCC) or N-ethyl-N'-(3-dimethylaminopropyl)carbodiimide hydrochloride (EDC), a carbodiimide together with an additive like 1-hydroxybenzotriazole (HOBT) or 1-hydroxy-7-azabenzotriazole (HOAT), a uronium-based coupling reagent like O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), or a phosphonium-based coupling reagent like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromotripyrrolidinophosphonium hexafluorophosphate (PyBroP). The activation of the compound of the formula IIa or IIb and the reaction of the activated compound of the formula IIa or IIb or a reactive carboxylic acid derivative with the compound of the formula III is generally carried out in an inert solvent, such as an ether like tetrahydrofuran (THF), dioxane or 1,2-dimethoxyethane (DME), or a hydrocarbon like toluene or a chlorinated hydrocarbon like dichloromethane or chloroform, or an amide like dimethylformamide (DMF) or N-methylpyrrolidin-2-one (NMP), for example, or a mixture of solvents, at temperatures from about 0° C. to about 60° C. in the presence of a suitable base such as a tertiary amine like triethylamine, ethyl-diisopropylamine, N-methylmorpholine or pyridine, or a basic alkaline metal compound such as an alkaline metal carbonate like sodium carbonate, potassium carbonate or cesium carbonate, for example.

The carboxylic acids of the formula IIa, or compounds which instead of the carboxylic acid group depicted in formula IIa contain a carboxylic acid derivative group, for example a carboxylic acid chloride group, can be obtained from the (aza)indolizines of the formula V by directly introducing a carboxylic acid group or carboxylic acid derivative group, or by first introducing an aldehyde group into the compound of the formula V to give a compound of the formula VI, and subsequently oxidizing the aldehyde group to the carboxylic group.

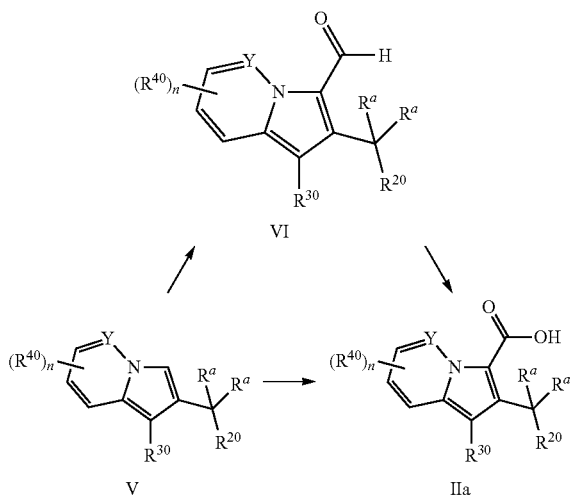

$R^a$, $R^{20}$, $R^{30}$, $R^{40}$, Y and n in the compounds of the formulae V and VI are defined as in the compounds of the formula Ia and additionally functional groups can be present in protected form or in the form of a precursor group, which is later converted into the final group.

The direct introduction of a carboxylic acid group or carboxylic acid derivative group into the compounds of the formula V can conveniently be accomplished by reaction with phosgene or a phosgene derivative such as triphosgene, which reaction results in the formation of the acid chlorides of the compounds of the formula IIa which can then be used in the subsequent reaction with the compound of the formula III without a further activation step and without isolation. The reaction with phosgene or a phosgene derivative such as triphosgene is generally carried out in an inert solvent, such as a hydrocarbon like toluene or benzene or a chlorinated hydrocarbon like dichloromethane, or a mixture of solvents at temperatures from about 0° C. to about 30° C., favorably in the presence of a base such as pyridine (cf. G. A. M. Giardina et al., Farmaco 54 (1999), 364). The formylation of the (aza) indolizines of the formula V to the compounds of the formula VI can conveniently be carried out under the conditions of the Vilsmeier reaction (cf. G. Jones, Organic Reactions 49 (1997), 1). The Vilsmeier reagent can be prepared in situ from dimethylformamide (DMF) and a suitable inorganic or organic chloride such as phosgene, oxalyl chloride or phosphorus oxychloride in an inert aprotic solvent, such as a hydrocarbon or a chlorinated hydrocarbon like benzene, dichloromethane or chloroform, or an ether like DME or an excess of DMF, or a mixture thereof, at temperatures from about 0° C. to about 10° C. Favorably, phosphorus oxychloride in an excess of DMF as solvent is employed. The reaction of the Vilsmeier reagent with the compound of the formula V is usually carried out at temperatures from about 0° C. to about 60° C. Hydrolytic workup of the reaction mixture, which like the workup of all reactions in the preparation of the compounds of the formulae Ia and Ib can generally be performed under standard conditions, then yields the aldehyde of the formula VI. Reagents for the oxidation of the aldehyde to the carboxylic acid of the formula IIa are permanganates such as potassium permanganate, which can be used in a mixture of water and an inert organic solvent, such as a ketone like acetone, or an ether like THF, at temperatures from about 10° C. to about 30° C. at about neutral pH values, or halogen oxidants such as chlorites like sodium chlorite, which can be used in the presence of 2-methylbut-2-ene in a mixture of water and an inert organic solvent, such as an alcohol like tert-butanol or an ether like THF, or a mixture thereof, at temperatures from about 0° C. to about 30° C. at weakly acidic pH values, for example in the presence of a dihydrogenphosphate.

Synthetic procedures which can be used in the preparation of the compounds of the formula V and further (aza)indolizine derivatives, are described in T. Uchida et al., Synthesis (1976), 209, for example. Compounds of the formula V in which the group Y is an optionally substituted carbon atom, i.e. compounds of the formula Va, can be synthesized from pyridine derivatives carrying an $R^{30}$—$CH_2$— substituent in the 2-position, i.e. compounds of the formula VII, and 3-substituted 1-halo-propanones of the formula VIII by the well-known Tschitschibabin method (cf. A. E. Tschitschibabin, Ber. Dtsch. Chem. Ges. 60 (1927), 1607; W. Chai et al., Synlett (2003), 2086), for example.

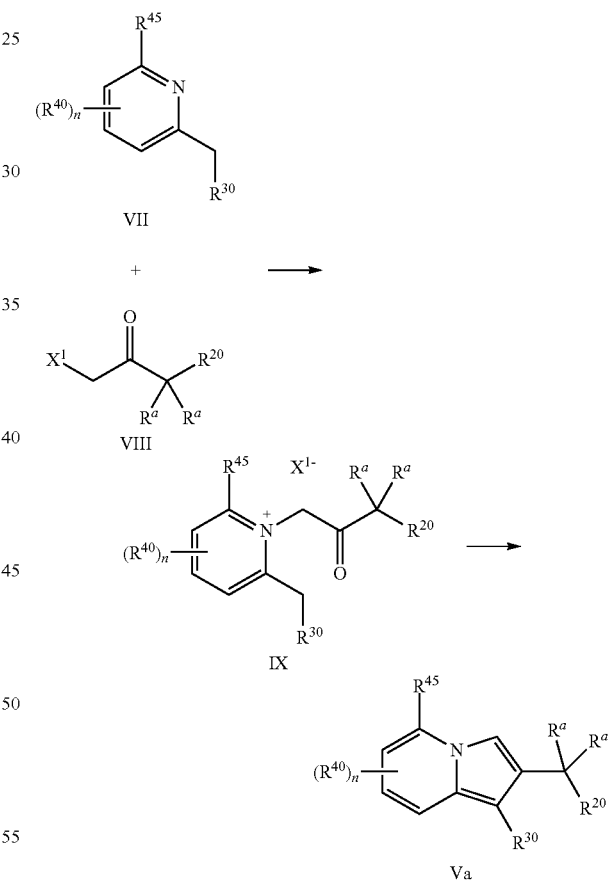

$R^a$, $R^{20}$, $R^{30}$, $R^{40}$ and n in the compounds of the formulae Va, VII, VIII and IX are defined as in the compounds of the formula Ia and additionally functional groups can be present in protected form or in the form of a precursor group, which is later converted into the final group. The group $R^{45}$ in the compounds of the formulae Va, VII and IX is defined as in the compounds of the formula Ic, i.e. $R^{45}$ is chosen from hydrogen and $(C_1-C_4)$-alkyl and corresponds to the hydrogen atom or the alkyl group present in the group Y in case Y in the compounds of the formula Ia is an optionally substituted carbon atom. The group $X^1$ in the compounds of the formula VIII favorably is chlorine or bromine, and accordingly the anion $X^{1-}$ in the compounds of the formula IX then is the chloride ion or the bromide ion, but can also be another anion, for example in case an anion exchange is performed and the compound of the formula IX is isolated.

According to the Tschitschibabin method for the preparation of indolizine derivatives, the 2-($R^{30}$—$CH_2$)-substituted pyridine derivative of the formula VII is quaternized with the halo-propanone of the formula VIII to give the quaternary salt of the formula IX, which is then cyclized in the presence of a base to give the compound of the formula Va. The procedure can be carried out with or without isolation of the compound of the formula IX. The reaction of the compounds of the formulae VII and VIII and the cyclization are generally carried out in a solvent, such as a hydrocarbon like toluene, or an ether like THF or dioxane, or a ketone like acetone or 2-butanone, or an alcohol like methanol, ethanol or isopropanol, or water, for example, or a mixture of solvents, with heating, for example at temperatures from about 50° C. to about 110° C. As a base in the cyclization step, an inorganic base, such as a basic alkaline metal salt, for example a carbonate or hydrogencarbonate like sodium carbonate, potassium carbonate or sodium hydrogencarbonate, or an organic base, for example an amine like triethylamine, or 1,8-diazabicyclo[5.4.0]undec-7-ene (DBU), can be employed. The reaction can also be performed with an excess of the pyridine derivative of the formula VII which then acts as the base in the cyclization step.

Compounds of the formula VII are commercially available or can be obtained by various procedures under standard conditions, for example from the respective compound containing a chlorine atom instead of the group $R^{30}$—$CH_2$— in the 2-position by reaction with the respective 9-($R^{30}$—$CH_2$)-substituted 9-borabicyclo[3.3.1]nonane (cf. A. Flaherty et al., Org. Lett. 7 (2005), 4975, for example), or from the respective compound containing a methyl group instead of the $R^{30}$—$CH_2$— group in the 2-position by metalation, for example with a lithium amide or an organolithium compound like n-butyllithium, and direct reaction of the compound metalated on the methyl group with an electrophilic reagent introducing the group $R^{30}$, for example a suitable reactive halo-substituted or sulfonyloxy-substituted cycloalkane, cycloalkene, tetrahydropyran, benzene or heteroarene derivative, or by first reacting the compound metalated on the methyl group with diisopropylketone and then reacting the obtained 1,1-diisopropyl-2-(pyridin-2-yl)-ethanol derivative with such an electrophilic reagent according to the procedure in T. Niwa et al., Angew. Chem. Int. Ed. 46 (2007), 2643, where such reactions are performed in the presence of a palladium compound like tetrakis(triphenylphosphine)palladium(0), tris(dibenzylideneacetone)dipalladium(0), palladium(II) acetate or palladium(II) trifluoroacetate and a phosphine like triphenylphosphine, tricyclohexylphosphine or 2-dicyclohexylphosphino-2',6'-dimethoxy-biphenyl, if necessary. Compounds of the formula VIII likewise are commercially available or can be prepared by various procedures under standard conditions, for example by reaction of the respective compound of the formula VIII containing a hydrogen atom instead of the group $X^1$ with bromine according to the bromination-debromination procedure described in H. Y. Choi et al., Org. Lett. 5 (2003), 411, to give the compound of the formula VIII in which $X^1$ is bromine, or by reaction of the respective 2-$R^{20}$-substituted acetyl chloride with trimethylsilyl diazomethane and treatment of the intermediary 3-$R^{20}$-substituted 1-diazo-propan-2-one with hydrobromic acid to give the compound of the formula VIII in which $X^1$ is bromine (cf. N. Desideri, Lett. Org. Chem. 3 (2006), 546), or by reaction of the respective compound of the formula $R^{20}$-$M^1$, in which $R^{20}$ is defined as in the compounds of the formula Ia and additionally functional groups can be present in protected form or in the form of a precursor group, and $M^1$ is a magnesium monohalide group and the compound of the formula $R^{20}$-$M^1$ is a Grignard compound, or $M^1$ is a metal like lithium, with a chloromethyl-oxirane, in particular epichlorohydrine, favorably in the presence of a copper compound like copper (I) iodide, followed by oxidation of the obtained 3-$R^{20}$-substituted 1-chloro-propan-2-ol to the ketone by means of one of the many common agents for the oxidation of secondary alcohols, for example by means of the Dess-Martin periodinane reagent, i.e. 1,1,1-triacetoxy-1,1-dihydro-1,2-benziodoxol-3(1H)-one, to give the compound of the formula VIII in which $X^1$ is chlorine (cf. H.-D. Becker et al., J. Org. Chem. 54 (1989), 3182; K. Okano et al., J. Am. Chem. Soc. 128 (2006), 7136). If desired, a compound of the formula VIII in which $X^1$ is chlorine, can conveniently be converted by treatment with lithium bromide in a solvent such as acetone, for example, into the respective compound of the formula VIII in which $X^1$ is bromine.

Compounds of the formula V in which Y is a nitrogen atom, i.e. compounds of the formula Vb, can be synthesized via pyrrole derivatives of the formula XIV, which can be obtained according to the Barton-Zard pyrrole synthesis (cf. D. H. R. Barton et al., Tetrahedron 46 (1990), 7587) from isocyanoacetates of the formula XIII and nitroolefines of the formula XII, which in turn can be obtained from nitro compounds of the formula X and aldehydes of the formula XI, N-amination on the pyrrole ring to give the compound of the formula XV, reaction with a malonaldehydic acid ester acetal of the formula XVI and introduction and/or modification of functional groups in the 6-membered ring of the azaindolizine ring system in the compound of the formula XVII.

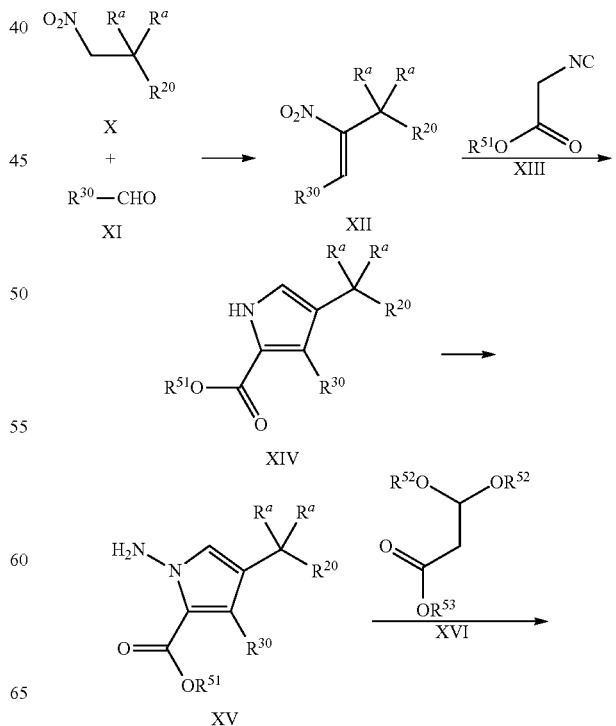

-continued

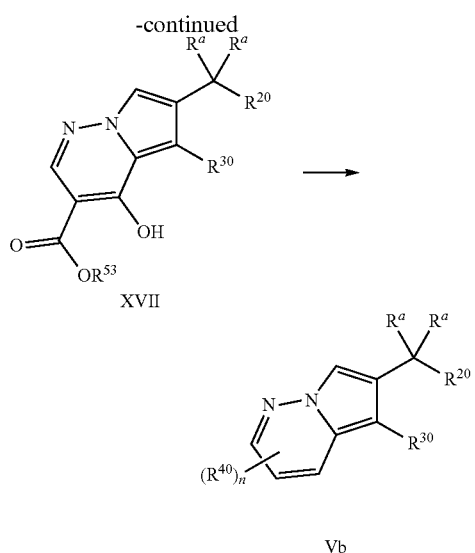

XVII

Vb $R^a$, $R^{20}$, $R^{30}$, $R^{40}$ and n in the compounds of the formulae Vb, X, XI, XII, XIII, XIV, XV, XVI and XVII are defined as in the compounds of the formula Ia and additionally functional groups can be present in protected form or in the form of a precursor group, which is later converted into the final group. The groups $R^{51}$, $R^{52}$ and $R^{53}$, which can be identical or different, conveniently are ($C_1$-$C_4$)-alkyl groups like methyl, ethyl or tert-butyl, for example. The starting compounds for this synthesis of compounds of the formula Vb are commercially available or can be obtained according to standard procedures which are described in the literature and known to the person skilled in the art, and are also outlined in the following.

The condensation reaction of the nitro compound of the formula X with the aldehyde of the formula XI to give the nitroolefin of the formula XII is generally carried out by heating the components in an inert solvent, such as a hydrocarbon like toluene or xylene, for example under removal of water by azeotropic distillation at reflux temperature of the solvent, and/or with addition of an acid like acetic acid or an amine like n-butylamine or an ammonium salt like ammonium acetate or n-butylammonium acetate, for example. By a similar condensation reaction of an aldehyde of the formula $R^{20}$—CHO, in which $R^{20}$ is defined as in the compounds of the formula Ia and additionally functional groups can be present in protected form or in the form of a precursor group, and nitromethane according to the Knoevenagel reaction, for example in acetic acid at reflux temperature in the presence of ammonium acetate, and reduction of the obtained nitrostyrene of the formula $R^{20}$—CH═CH—$NO_2$, in which $R^{20}$ is defined as in the compounds of the formula Ia and additionally functional groups can be present in protected form or in the form of a precursor group, for example by means of sodium borohydride in the presence of silica gel as described in A. K. Sinhababu et al., Tetrahedron Lett. 24 (1983), 227, compounds of the formula X can be obtained in which the groups $R^a$ are hydrogen. A procedure for the preparation of compounds of the formula X in which $R^a$ is different from hydrogen, in which the respective compound of the formula $R^{20}$—C($R^a$)$_2$—$NO_2$, in which $R^a$ and $R^{20}$ are defined as in the compounds of the formula Ia and additionally functional groups can be present in protected form or in the form of a precursor group, is reacted with nitromethane in the presence of sodium hydride in dimethyl sulfoxide, is described in N. Kornblum et al., J. Org. Chem. 46 (1981), 1037. The reaction of the compound of the formula XII with the isocyanoacetic acid ester of the formula XIII to give the pyrrole derivative of the formula XIV is favorably carried out in an inert solvent, such as an ether like THF or dioxane or an alcohol such as isopropanol, or a mixture of solvents, in the presence of a base, for example tetramethylguanidine or DBU (cf. D. H. R. Barton et al., Tetrahedron 46 (1990), 7587; J. A. Pfefferkorn et al., Bioorg. Med. Chem. Lett. 17 (2007), 4538).

As reagents for the N-amination of the compound of the formula XIV to give the compound of the formula XV, hydroxylamine-O-sulfonic acid/potassium hydroxide, ammonia/ammonium chloride/sodium hypochlorite/sodium hydroxide, or O-(4-nitrobenzoyl)-hydroxylamine/potassium tert-butoxide may be mentioned. Favorably, the N-amination is performed by treating the compound of the formula XIV in an inert solvent such as an amide like DMF with a base such as sodium hydride and with O-(2,4-dinitrophenyl)-hydroxylamine as aminating reagent at temperatures from about 0° C. to about 30° C. (cf. C. Legault et al., J. Org. Chem. 68 (2003), 7119; P. H. Boyle et al., ARKIVOC (2003) (vii), 67; K. S. Kim et al., Bioorg. Med. Chem. Lett. 16 (2006), 3937). The condensation of the 1-amino-group of the pyrrole derivative of the formula XV with the masked aldehyde group of the malonaldehydic acid ester acetal of the formula XVI and the subsequent cyclization of give the 4-hydroxy-pyrrolo[1,2-b]pyridazine derivative of the formula XVII, which can also be present in a tautomeric form and designated as a 4-oxo-1,4-dihydro-pyrrolo[1,2-b]pyridazine or 1H-pyrrolo[1,2-b]pyridazin-4-one derivative, can be carried out by reacting the components in an inert solvent, for example an amide like DMF, with heating, for example to temperatures from about 40° C. to about 100° C., first under acidic conditions, for example in the presence of a sulfonic acid like toluene-4-sulfonic acid, and subsequently under basic conditions, for example in the presence of an organic base like DBU.

Depending on the desired substituents in compound of the formula Vb or the final compound of the formula Ia, substituents can then be introduced in the 6-membered ring in the azaindolizine ring system in the compound of the formula XVII and/or the ester group and/or the hydroxy group in the compound of the XVII modified or removed. For example, the hydroxy group can be alkylated, or it can be replaced with a halogen atom, for example a chlorine atom, by treatment with a halogenating agent such as a phosphorus halide, for example phosphorus oxychloride. Such a replacement can also occur concomitantly with a Vilsmeier formylation of a compound of the formula XVII or Vb with DMF and phosphorus oxychloride, for example, to give a compound of the formula VI as outlined above. In a compound of the formula XVII, in which the hydroxy group is replaced with a chlorine atom, or in a compound which has been obtained from the compound of the formula XVII by a Vilsmeier formylation and subsequent oxidation to a carboxylic acid of the formula IIa and optionally further reactions, the chlorine atom in the 6-membered ring of the azaindolizine ring system can then be replaced with another group in a substitution reaction, or it can be replaced with a hydrogen atom, for example by hydrogenation in the presence of a transition metal catalyst such as palladium on charcoal and a base such as triethylamine. The ester group can likewise be replaced with a hydrogen atom by hydrolysis to the carboxylic acid, for example by treatment with an alkaline metal hydroxide like lithium hydroxide or sodium hydroxide, and decarboxylation of the carboxylic acid by heating it with copper in quinoline. The said carboxylic acid can also be converted into a carboxamide as outlined above with respect to the reaction of the carboxylic acids of the formula IIa with the compounds of the formula III. The ester group, or the said carboxylic acid or a suitable carboxamide obtained therefrom can either directly be reduced to the aldehyde, or they can be reduced to the hydroxymethyl compound which can be oxidized to the aldehyde, and the aldehyde group can be converted into a hydroxy group according to the Baeyer-Villiger procedure by oxidation with a peracid and hydrolysis, where the hydroxy group can then be alkylated. A primary carboxamide group obtained from the ester or the said carboxylic acid can be converted into a nitrile group, and various other modifications can be carried out, if desired. These explanations on the introduction, modification and removal of functional groups in the 6-membered ring of the (aza)indolizine ring system in the compounds of the formulae Vb and XVII apply correspondingly to the compounds of the formulae IIa, IIb, Va, XX and other compounds defined above or below, in which likewise functional groups can be introduced, modified or removed. As further examples of such reactions of these compounds the introduction of bromine substituents may be mentioned, which can conveniently be carried out via a bromination/debromination sequence by treatment with bromine and subsequently with a base such as DBU (cf. A. Kakehi et al., Chem. Pharm. Bull. 52 (2004), 279), or the preparation of amino-substituted compounds via the replacement of a halogen substituent such as a bromine or iodine substituent with an amine under the conditions of the Buchwald-Hartwig reaction in the presence of a palladium catalyst such as tris(dibenzylideneacetone)dipalladium(0) and a phosphine such as tri(o-tolyl)phosphine, for example (cf. J. P. Wolfe et al., Acc. Chem. Res. 31 (1998), 8052).

Compounds of the formula IIb, or respective compounds which instead of the carboxylic acid group depicted in formula IIb contain a carboxylic acid derivative group such as an ester group, i.e. compounds of the formula XX, can be synthesized in a procedure which starts from a pyridin-2-yl-acetic acid ester or a pyridazin-3-yl-acetic acid ester of the formula XVIII and a 3-substituted 1-halo-propanone of the formula VIII and involves the well-known Tschitschibabin method like the synthesis of the compounds of the formula Va described above. Further information on this procedure can likewise be found in T. Uchida et al., Synthesis (1976), 209, for example.

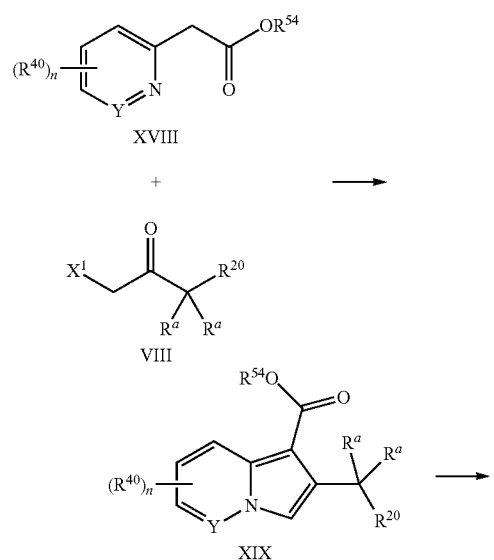

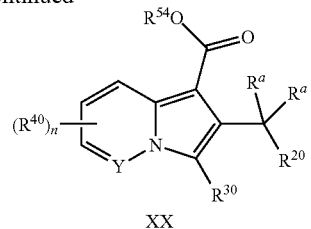

$R^a$, $R^{20}$, $R^{30}$, $R^{40}$, Y and n in the compounds of the formulae XVIII, XIX and XX are defined as in the compounds of the formula Ib and additionally functional groups can be present in protected form or in the form of a precursor group, which is later converted into the final group. The group $R^{54}$ in the compounds of the formulae XVIII, XIX and XX can be a ($C_1$-$C_4$)-alkyl group like methyl, ethyl or tert-butyl, for example, but can also be another group such as benzyl. Compounds of the formula XX which contain a carboxylic acid group COOH instead of the group $COOR^{54}$, which compounds are readily obtained from the compounds of the formula XX, are compounds of the formula IIb, and hydrogen can accordingly be regarded as a further denotation of $R^{54}$ in the compounds of the formula XX.

Compounds of the formula XVIII are commercially available or can be obtained by various procedures under standard conditions, for example from the respective heteroarene containing a chlorine atom instead of the group $CH_2$—$COOR^{54}$ by reaction with a dialkyl malonate and hydrolysis and decarboxylation of one of the ester groups of the obtained dialkyl heteroarene-malonate, or from the respective heteroarene containing a methyl group instead of the group $CH_2$—$COOR^{54}$ by metalation, for example by means of a lithium compound such as n-butyllithium or lithium diisopropylamide and reaction with a dialkyl carbonate (cf. EP 1958946; A. Ohsawa et al., Chem. Pharm. Bull. 26 (1978), 3633). The reaction of the compounds of the formulae VIII and XVIII to give the compound of the formula XIX can be performed analogously as outlined above with respect to the reaction of the compounds of the formulae VII and VIII to give the compound of the formula IX and the cyclization of the latter compound to give the compound of the formula Va, favorably without isolation of the intermediary salt corresponding to the compound of the formula IX, for example by heating the components together with a base such as an alkaline metal hydrogencarbonate like sodium hydrogencarbonate in a solvent such as a ketone like acetone or 2-butanone to temperatures from about 50° C. to about 100° C. For the introduction of the group $R^{30}$ to give the compound of the formula XX, the compound of the formula XIX is favorably reacted with a compound of the formula $R^{30}$—$X^2$ in which $R^{30}$ is defined as in the compounds of the formula Ib and additionally functional groups can be present in protected form or in the form of a precursor group, and $X^2$ is a suitable leaving group, for example halogen like bromine or iodine, in a transition metal-catalyzed coupling reaction, for example in the presence of a palladium compound such as bis(triphenylphosphine)palladium(II) chloride or tetrakis(triphenylphosphine)palladium(0) and a base such as a basic alkaline metal salt like potassium acetate in an inert solvent such as an amide like DMF or NMP at temperatures from about 60° C. to about 120° C.

The diazacycloalkanes of the formula III, which are reacted in an amide coupling reaction with the compounds of the formulae IIa and IIb to give the compounds of the formulae IVa and IVb and, after optional conversion of the group $R^{50}$ into the group $R^{10}$, the final compounds of the formulae Ia and Ib, are commercially available or can be prepared according to, or analogously to, standard procedures described in the literature (cf. WO 96/31501; WO 2005/026177; WO 2005/061510; S. Fustero et al., Org. Lett. 9 (2007), 5283, for example) which are also illustrated in an exemplary manner in the following. Chiral compounds of the formula III in which p and q both are 2, one of the groups R is different from hydrogen and all other groups R are hydrogen, for example, can be prepared in a procedure starting from chiral α-amino acid derivatives of the formula XXI and an N-benzyl-glycine ester of the formula XXII. According to this procedure, compounds of the formula III can be obtained in which the chiral carbon atom carrying the group R which is different from hydrogen, is present adjacent to the group NH in the compound of the formula III, for example compounds of the formula IIIa, and compounds in which the chiral carbon atom carrying the group R which is different from hydrogen, is present adjacent to the group $NR^{50}$ in the compound of the formula III, for example compounds of the formula IIIb. Furthermore, according to this procedure compounds of the formula III can be obtained in which the chiral carbon atom has S configuration or has R configuration or is present as a racemic mixture, for example, depending on whether an α-amino acid derivative having S configuration or R configuration (or L configuration or D configuration) or a racemic mixture thereof is employed.

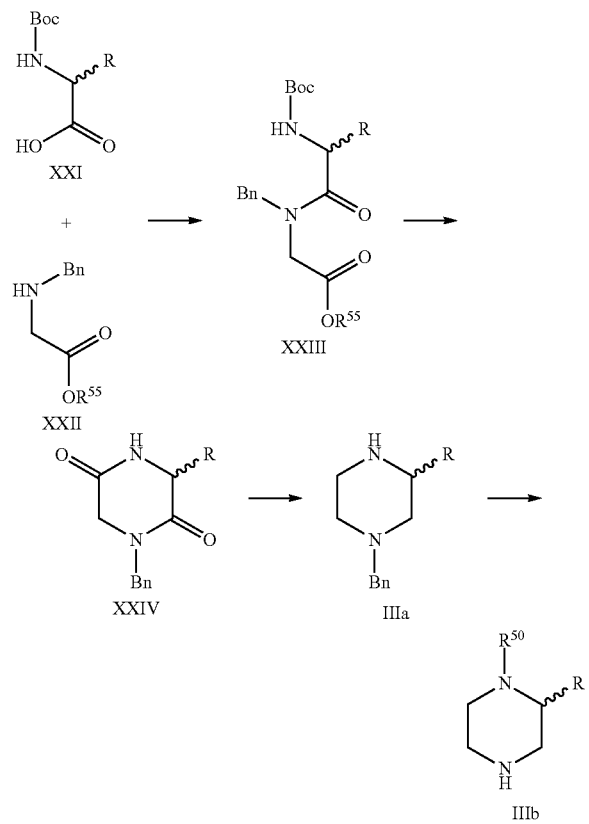

The groups R and $R^{50}$ in the compounds of the formulae IIIa, IIIb, XXI, XXIII and XXIV are defined as in the compounds of the formulae Ia and Ib and additionally functional groups can be present in protected form or in the form of a precursor group, which is later converted into the final group, i.e. they are defined as in the compounds of the formula III, except that such a procedure will not be carried out in case R is hydrogen. The group $R^{55}$ conveniently is a ($C_1$-$C_4$)-alkyl group, for example methyl or ethyl. The group Bn in the compounds of the formulae IIIa, XXII, XXIII and XXIV is the benzyl group. The group Boc in the compounds of the formulae XXI and XXIII is the tert-butyloxycarbonyl group. The starting compounds of the formulae XXI and XXII are commercially available or can be obtained according to standard procedures from the respective amino acids. For the amide coupling reaction of the compounds of the formula XXI with the compounds of the formula XXII, the compound of the formula XXI is activated or converted into a reactive derivative, and the reaction is performed, under standard conditions as outlined above with respect to the reaction of the compounds of the formulae IIa and IIb with the compounds of the formula III. Likewise, the removal of the Boc group from the compound of the formula XXIII, for example by treatment with trifluoroacetic acid, the cyclization of the obtained compound of the formula XXIII in which the Boc group is replaced with a hydrogen atom, to give the diketopiperazine derivative of the formula XXIV, for example by treatment with an organic base such as an amine like triethylamine, the reduction of the compound of the formula XXIV to give the compound of the formula IIIa, for example by treatment with a metal hydride reducing agent such as lithium aluminium hydride, and, in case a compound of the formula IIIb is to be prepared, the introduction of the group $R^{50}$, for example by treatment with a chloroformate or a dicarbonate such as di-tert-butyl dicarbonate in case the group $R^{50}$ in the compound of the formula IIIb is to be an ester group such as an alkyl-O—C(O)—, cycloalkyl-O—C(O)— or cycloalkylalkyl-O—C(O)— group like the Boc group, for example, and the removal of the Bn group, for example by hydrogenation in the presence a transition metal catalyst such as a palladium catalyst like palladium(II) hydroxide on charcoal, can be performed under standard conditions.

In the compounds of the formulae IIIa and IIIb various modifications in the group R and/or on the ring nitrogen atoms can be carried out to give further compounds of the formula III. For example, if the compound of the formula XXI which is employed in the procedure outlined afore, is an (S)—N-tert-butoxycarbonyl-aspartic acid β alkyl ester such as the β methyl ester or (S)—N-tert-butoxycarbonyl-aspartic acid β-benzyl ester, i.e. the group R is the group —$CH_2$—C(O)—$OCH_3$ or —$CH_2$—C(O)—O-benzyl, for example, in the reduction of the compound of the formula XXIV, for example with lithium aluminium hydride in THF at a temperature of about 60° C., simultaneously the β ester group can be reduced to a hydroxymethyl group, and thus the compound of the formula IIIc, i.e. the compound (S)-2-(2-hydroxyethyl)-piperazine-1-carboxylic acid tert-butyl ester, can be obtained in case the introduced group $R^{50}$ is the Boc group. In the compound of the formula IIIc, in which the hydroxy group can be protected as a silyl ether by treatment with tert-butyl-dimethyl-silyl chloride and later deprotected by treatment with a fluoride such as potassium fluoride, cesium fluoride of tetrabutylammonium fluoride, for example, can the NH group in the ring be protected by introduction of the benzyloxycarbonyl group by treatment with benzyl chloroformate in the presence of a base such as sodium hydrogencarbonate, for example.

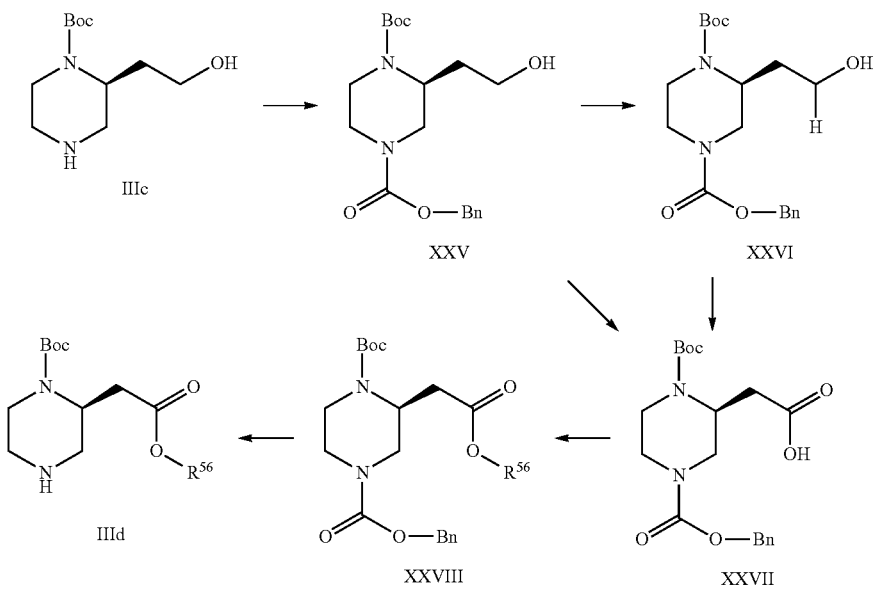

In the obtained compound of the formula XXV can the hydroxy group be alkylated to give an alkyl-O— group, or it can be activated, for example by conversion into the methanesulfonate, and reacted with an alkanethiol or a metal cyanide to give a thioether or a nitrile, or it can be oxidized to give the aldehyde of the formula XXVI, for example by treatment with the Dess-Martin periodinane reagent (cf. above). The methanesulfonate of the compound of the formula XXV and the compound of the formula XXVI can also be reacted with other nucleophilic compounds, for example amino compounds, and heterocycles prepared, and the compound of the formula XXVI can be oxidized to the carboxylic acid of the formula XXVII, for example by treatment with sodium chlorite as outlined above with respect to the oxidation of the aldehydes of the formula VI. The compound of the formula XXV can also be oxidized directly to the compound of the formula XXVII, for example by treatment with pyridinium dichromate. The carboxylic acid of the formula XXVII can be activated as outlined above with respect to the compounds of the formulae IIa and IIb and converted into carboxamides and heterocycles, or esterified, for example by treatment with a haloalkane in the presence of a base such as potassium carbonate in a solvent such as a ketone like acetone or butanone to give a compound of the formula XXVIII.

The group $R^{56}$ in the compounds of the formula XXVIII, as well as in the compounds of the formula IIId, is a ($C_1$-$C_4$)-alkyl group such as methyl or ethyl, for example. In the compounds of the XXVIII can the benzyloxycarbonyl group Bn-O—C(O)— be removed by catalytic hydrogenation in the presence of a transition metal catalyst such as palladium on charcoal to give the compounds of the formula IIId, which can then be reacted with the compounds of the formulae IIa and IIb to give compounds of the formulae IVa and IVb. Like in the compounds of the formula XXVIII can in all other compounds, which can be obtained from the compounds of the formula IIIc as outlined afore, the benzyloxycarbonyl group be removed and the respective compounds containing a free NH group reacted with the compounds of the formulae IIa and IIb to give compounds of the formulae IVa and IVb. Further compounds of the formulae IVa and IVb can be obtained by removing the Boc group instead of the benzyloxycarbonyl group, for example by treatment with trifluoroacetic acid, and reacting the obtained compounds with the compounds of the formulae IIa and IIb, and finally removing the benzyloxycarbonyl group.

Besides in the compounds of the formula III, or in the course of the preparation of compounds of the formula III, as outlined afore, can respective modifications of functional groups also be made, or functional groups also be introduced, subsequent to the reaction of the compounds of the formula III with the compounds of the formulae IIa and IIb, i.e. in the compounds of the formulae IVa and IVb. All explanations made afore apply correspondingly to such a synthetic approach. For example, a compound of the formula IIa or IIb can be reacted with the compound of the formula IIIc, wherein in such a reaction the hydroxy group in the compound of the formula IIIc generally is protected, for example as the tert-butyl-dimethyl-silyl ether which has been obtained by treatment with tert-butyl-dimethyl-silyl chloride in the presence of imidazole and later is cleaved by treatment with a fluoride, to give a compound of the formula IVc or IVd. Analogously to the procedures outlined afore, the $CH_2OH$ group depicted in the formulae IVc and IVd can be oxidized to the aldehyde group C(O)H by treatment with the Dess-Martin periodinane reagent, and the aldehyde group can in turn be oxidized with sodium chlorite to give the carboxylic acids of the formulae IVe and IVf.

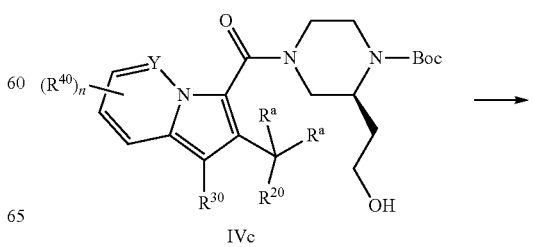

IVc

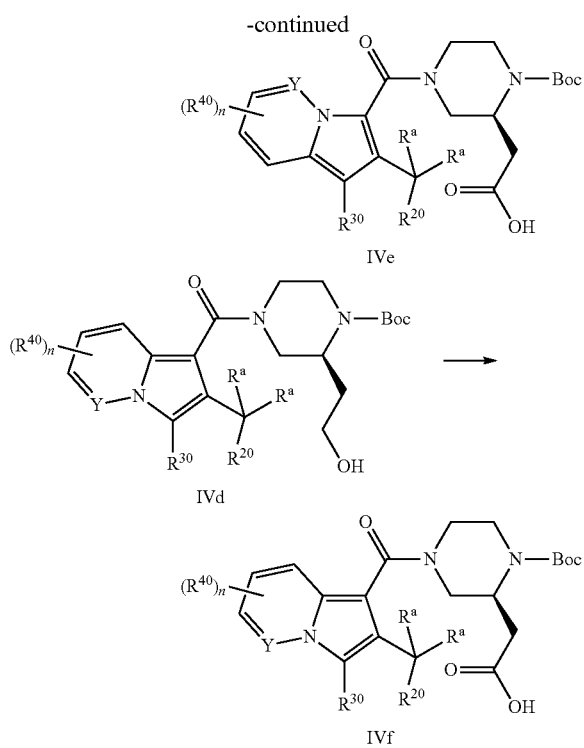

$R^a$, $R^{20}$, $R^{30}$, $R^{40}$, Y and n in the compounds of the formulae IVc, IVd, IVe and IVf are defined as in the compounds of the formulae IVa and IVb, and Boc is the tert-butyloxycarbonyl group. The compounds of the formulae IVe and IVf are as well obtained by reaction of the compounds of the formula IIId with the compounds of the formulae IIa and IIb and hydrolysis of the ester group C(O)—$OR^{56}$, for example by treatment with lithium hydroxide in case $R^{56}$ is methyl or ethyl. The C(O)—OH group depicted in the formulae IVe and IVf can be activated or converted into a reactive derivative as outlined above with respect to the compounds of the formulae IIa and IIb and reacted with an amine of the formula $R^2$—N($R^3$)—H, in which the groups $R^2$ and $R^3$ are defined as in the compounds of the formulae Ia and Ib and additionally functional groups can be present in protected form or in the form of a precursor group, which is later converted into the final group, to give the respective compounds of the formulae IVe and IVf in which the group C(O)—OH is replaced with the group C(O)—N($R^3$)—$R^2$, and which can be converted into compounds of the formulae Ia and Ib in which $R^{10}$ is hydrogen by treatment with trifluoroacetic acid or hydrogen chloride for removal of the Boc group. As another example of modifications of functional groups which can be made in the compounds of the formulae IVc and IVd, the conversion of the hydroxy group depicted in formulae IVc and IVd into an alkoxy group may be mentioned, which can be performed by alkylating a compound of the formula IVc or IVd with a reactive haloalkane, for example a bromoalkane or a iodoalkane, or reacting an alkanol with a compound containing a leaving group instead of the hydroxy group, such as a methanesulfonyloxy group obtained by reaction of the compound of the formula IVc or IVd with methanesulfonyl chloride, for example, in the presence of a base such as potassium carbonate or cesium carbonate in an inert solvent such as a ketone like acetone or butanone or an amide such as DMF or NMP. All explanations relating to the preparation of compounds in which p and q both are 2, one of the groups R is different from hydrogen and all other groups R are hydrogen, apply correspondingly to other compounds.

In order to obtain further compounds of the formulae Ia and Ib, various other transformations of functional groups can be carried out in compounds of the formulae Ia and Ib as well as in the compounds occurring as intermediates in the synthesis of the compounds of the formulae Ia and Ib. With respect to all parts of the molecules it applies that, for example, a hydroxy group can be etherified under standard conditions by alkylation with the respective halogen compound, in particular a bromide or iodide, in the presence of a base such an alkaline metal carbonate in an inert solvent, or with the respective alcohol under the conditions of the Mitsunobu reaction in the presence of an azodicarboxylate like diethyl azodicarboxylate or diisopropyl azodicarboxylate and a phosphine like triphenylphosphine or tributylphosphine in an inert aprotic solvent such as an ether like THF or dioxane (cf. O. Mitsunobu, Synthesis (1981), 1). An amino group can be modified under standard conditions for alkylation, for example by reaction with a halogen compound or by reductive amination of a carbonyl compound, or for acylation, for example by reaction with an activated carboxylic acid or a carboxylic acid derivative like an acid chloride or anhydride. A carboxylic acid group can be activated or converted into a reactive derivative as outlined above and reacted with an alcohol or amine to give an ester or amide. An alkyl-S— group can be oxidized with a peroxide like hydrogen peroxide or a peracid to give an alkyl-S(O)— or alkyl-S(O)$_2$— group, and a protected mercapto group can be deprotected and oxidized to give a sulfonic acid which can then be activated and reacted with an amine under standard conditions to give a sulfonamide. Hydroxy groups which have been activated, for example by conversion into the methanesulfonyl or the trifluoromethanesulfonyl derivative, and reactive halogen atoms can be replaced with groups bonded via an oxygen, sulfur, nitrogen or carbon atom in nucleophilic substitution reactions and metal-catalyzed reactions.

As already indicated above, in case the group $R^{50}$ in the compound of the formulae IVa and IVb has any of the meanings of the group $R^{10}$ in the compounds of the formulae Ia and Ib and all other groups have the desired meanings comprised by the definition of the compounds of the formulae Ia and Ib, the compounds of the formulae IVa and IVb are already the final compounds of the formulae Ia and Ib. In case $R^{50}$ is a protective group and a compound of the formula Ia or Ib is to be prepared in which $R^{10}$ is hydrogen, and/or any other groups are present in protected form or in the form of a precursor group, the compound of the formula IVa or IVb can finally be converted into the desired compound of the formula Ia or Ib by removal of protection groups and/or conversion of any other groups. As already indicated above, in order to avoid an undesired course of a reaction or side reactions, in any one or more steps in the synthesis of the compounds of the formulae Ia and Ib functional groups can generally be present in protected form or in the form of a precursor group. Besides in the final step of the synthesis of a compound of the formula Ia or Ib, protective groups can be removed, and precursor groups can be converted, also at other stages of the synthesis. Respective synthetic strategies and details about suitable protective groups and their introduction and removal are known to a person skilled in the art and are found in P. G. M. Wuts and T. W. Greene, Greene's Protective Groups in Organic Synthesis, 4. ed. (2007), John Wiley & Sons, for example. Examples of protective groups which may be mentioned in general, are benzyl protective groups such as in benzyl ethers of hydroxy groups and benzyl esters of carboxylic acid groups from which the benzyl group can be removed by catalytic hydrogenation in the presence of a palladium catalyst, tert-butyl protective groups such as in tert-butyl esters of carboxylic acid groups from which the tert-butyl group can be removed by treatment with trifluoroacetic acid, acyl protective groups which can protect hydroxy groups and amino groups in the form of esters and amides and which can be cleaved by acidic or basic hydrolysis, alkyloxycarbonyl protective groups such as in tert-butoxycarbonyl derivatives of amino groups, including the cyclic amino group being part of the diazacycloalkane moiety depicted in formulae Ia and Ib in case $R^{10}$ is hydrogen, which can be cleaved by treatment with trifluoroacetic acid, and silyl protective groups like tert-butyl-dimethyl-silyl and trimethylsilyl which can protect hydroxy groups in the form of the silyl ethers and which be can cleaved by treatment with a fluoride. Examples of precursor groups which may be mentioned are nitro groups which can be converted to amino groups by catalytic hydrogenation or by reduction with sodium dithionite, for example, and cyano groups which can be converted to carboxamide groups and carboxylic acid groups by hydrolysis.

The reactions carried out in the preparation of the compounds of the formulae Ia and Ib are known per se and can be carried out in a manner familiar to a person skilled in the art by, or analogously to, procedures which are described in the standard literature, for example in Houben-Weyl, Methods of Organic Chemistry, Thieme; Organic Reactions, John Wiley & Sons; or R. C. Larock, Comprehensive Organic Transformations: A Guide to Functional Group Preparations, 2. ed. (1999), John Wiley & Sons, and the references quoted therein.

A subject of the present invention also are the novel starting compounds and intermediates occurring in the synthesis of the compounds of the formulae Ia and Ib, including the compounds of the formulae IIa, IIb, III, IIIa, IIIb, IIId, IVa, IVb, IVc, IVd, IVe, IVf, V, Va, Vb, VI, VII, VIII, IX, X, XI, XII, XIV, XV, XVII, XVIII, XIX, XX, XXI, XXIII, XXIV, XXVI, XXVII, XXVIII, wherein R, $R^a$, $R^{20}$, $R^{30}$, $R^{40}$, $R^{45}$, $R^{50}$, $R^{51}$, $R^{53}$, $R^{54}$, $R^{55}$, $R^{56}$, Bn, Boc, $X^1$, Y, n, p and q are defined as above, in any of their stereoisomeric forms or a mixture of stereoisomeric forms in any ratio, and their salts, and solvates of any of them, and their use as intermediates. The general explanations, preferred definitions of groups and numbers and embodiments of the invention given above with respect to the compounds of the formulae Ia and Ib apply correspondingly to the said intermediates and starting compounds. A subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The compounds of the formulae Ia and Ib inhibit the enzyme renin as can be demonstrated in the pharmacological tests described below and in other pharmacological tests which are known to a person skilled in the art, for example in in vitro tests in which the inhibition of human renin is determined, or in animal models in which the antihypertensive activity and other effects are determined in vivo. The compounds of the formulae Ia and Ib are suitable for the treatment of hypertension including pulmonary hypertension, for example, and other disorders of the cardiovascular system and heart diseases, such as heart failure, cardiac infarction, angina pectoris, cardiac insufficiency, cardiac failure, cardiac hypertrophy, cardiac fibrosis, vascular hypertrophy, left ventricular dysfunction, in particular left ventricular dysfunction after myocardial infarction, endothelial dysfunction, ischemic and obstructive peripheral circulation disorders and restenosis including restenosis post-angioplasty, for example, for the treatment of renal diseases such as renal fibrosis, renal ischemia, renal failure and kidney insufficiency, for example, and for the treatment of other diseases, for example diabetes complications, such as nephropathy and retinopathy, cerebral afflictions, such as cerebral hemorrhage, glaucoma, and end-organ damage. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals who are susceptible thereto and are in need of such a prophylaxis or prevention, with the aim of prevention or suppression of their occurrence or of an attenuation in the case of their occurrence. For example, in patients who on account of their disease history are susceptible to ventricular dysfunction after myocardial infarction, by means of the prophylactic or preventive medicinal treatment the occurrence of ventricular dysfunction can be prevented or its extent and sequelae decreased. The treatment of diseases can occur both in acute cases and in chronic cases.

The compounds of the formulae Ia and Ib and their physiologically acceptable salts and physiologically acceptable solvates thereof can therefore be used in animals, in particular in mammals and specifically in humans, as a pharmaceutical or medicament on their own, in mixtures with one another or in the form of pharmaceutical compositions. A subject of the present invention also are the compounds of the formulae Ia and Ib and their physiologically acceptable salts and physiologically acceptable solvates thereof for use as a pharmaceutical, as well as pharmaceutical compositions and medicaments which comprise an efficacious dose of at least one compound of the formula Ia or Ib and/or a physiologically acceptable salt thereof and/or a physiologically acceptable solvate of any of them as an active ingredient and a pharmaceutically acceptable carrier, i.e. one or more pharmaceutically innocuous vehicles and/or excipients. A subject of the present invention furthermore are the compounds of the formulae Ia and Ib and their physiologically acceptable salts and physiologically acceptable solvates thereof for use in the treatment of the diseases mentioned above or below, for example of hypertension, or for the inhibition of renin, as well as the use of the compounds of the formulae Ia and Ib and their physiologically acceptable salts and physiologically acceptable solvates thereof for the manufacture of a medicament for the treatment of the diseases mentioned above or below, for example of hypertension, or for the manufacture of a medicament for the inhibition of renin, wherein the treatment of diseases comprises their therapy and prophylaxis. A subject of the invention also are methods for the treatment of the diseases mentioned above or below, which comprise administering an efficacious amount of at least one compound of the formula Ia or Ib or a physiologically acceptable salt thereof or a physiologically acceptable solvate of any of them to a human or an animal who is in need thereof. The compounds of the formulae Ia and Ib and pharmaceutical compositions and medicaments comprising them can be administered enterally, for example by oral, buccal, sublingual or rectal administration, parenterally, for example by intravenous, intramuscular or subcutaneous injection or infusion, or by another type of administration such as topical, percutaneous, transdermal, intratracheal, intranasal or intraocular administration.

The pharmaceutical compositions and medicaments according to the invention normally contain about 0.5 to about 90 percent by weight of compounds of the formulae Ia and Ib and/or their physiologically acceptable salts and/or physiologically acceptable solvates thereof. The amount of active ingredient of the compound of the formula Ia or Ib and/or its physiologically acceptable salt and/or a physiologically acceptable solvate of any of them in the pharmaceutical compositions and medicaments is in general about 0.2 mg to about 1000 mg, preferably about 0.2 mg to about 500 mg, particularly preferably about 1 mg to about 300 mg, per unit dose. The production of the pharmaceutical compositions and medicaments can be carried out in a manner known per se. For this, the compounds of the formulae Ia and Ib and/or their physiologically acceptable salts and/or physiologically acceptable solvates thereof are mixed together with one or more solid or liquid vehicles and/or excipients, if desired also in combination with one or more other active ingredients such as, for example, an angiotensin converting enzyme inhibitor, an angiotensin receptor antagonist, a diuretic, an endothelin receptor antagonist, an endothelin converting enzyme inhibitor, a neutral endopeptidase inhibitor, a calcium channel blocker, a nitrate like isosorbiddinitrate, a β-receptor blocker, an α1-adrenoreceptor antagonist, a cannabinoid receptor antagonist, a potassium channel modulator, a thromboxane synthetase inhibitor, an anti-serotoninergic agent, or another agent useful for treating hypertension, heart failure, vascular diseases related to diabetes or renal diseases such as acute or chronic renal failure, for example, and are brought into a suitable form for dosage and administration which can then be used in human medicine or veterinary medicine. A subject of the present invention also is in particular a pharmaceutical composition which comprises an efficacious dose of at least one compound of the formula Ia or Ib and/or a physiologically acceptable salt thereof and/or a physiologically acceptable solvate of any of them and one or more other active ingredients and a pharmaceutically acceptable carrier, wherein the other active ingredients are useful for the treatment of hypertension, cardiac infarction, heart failure, vascular diseases related to diabetes, end-organ damage such as cardiac insufficiency or kidney insufficiency, renal diseases such as acute or chronic renal failure, restenosis or glaucoma, and wherein as examples of such other active ingredients angiotensin converting enzyme inhibitors, angiotensin receptor antagonists, diuretics, endothelin receptor antagonists, endothelin converting enzyme inhibitors, neutral endopeptidase inhibitors, calcium channel blockers, nitrates like isosorbiddinitrate, β-receptor blockers, α1-adrenoreceptor antagonists, cannabinoid receptor antagonists, potassium channel modulators, thromboxane synthetase inhibitors and anti-serotoninergic agents may be mentioned.

As vehicles and excipients, suitable organic and inorganic substances can be used which do not react in an undesired manner with the compounds of the formulae Ia and Ib. Examples which may be mentioned are water, vegetable oils, waxes, alcohols such as ethanol, isopropanol, 1,2-propanediol, benzyl alcohols or glycerol, polyols, polyethylene glycols, polypropylene glycols, glycerol triacetate, gelatin, carbohydrates such as lactose or starch, stearic acid and its salts such as magnesium stearate, talc, lanolin, petroleum jelly, or mixtures thereof, for example mixtures of water with one or more organic solvents such as mixtures of water with alcohols. For oral and rectal use, in particular pharmaceutical forms such as, for example, tablets, film-coated tablets, sugar-coated tablets, granules, hard and soft gelatin capsules, suppositories, solutions, preferably oily, alcoholic or aqueous solutions, syrups, juices or drops, furthermore suspensions or emulsions, can be used. For parenteral use, for example by injection or infusion, in particular pharmaceutical forms such as solutions, preferably aqueous solutions, can be used. For topical use, in particular pharmaceutical forms such as ointments, creams, pastes, lotions, gels, sprays, foams, aerosols, solutions or powders can be used. Further suitable pharmaceutical forms are, for example, implants and patches and forms adapted to inhalation. The compounds of the formulae Ia and Ib and their physiologically acceptable salts and physiologically acceptable solvates of any of them can also be lyophilized and the obtained lyophilizates used, for example, for the production of injectable compositions. In particular for topical application, liposomal compositions are also suitable. As examples of types of excipients or additives which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants and flavoring substances may be mentioned. The pharmaceutical compositions and medicaments can also contain one or more other active ingredients and/or, for example, one or more vitamins.

As usual, the dosage of the compounds of the formulae Ia and Ib depends on the circumstances of the specific case and is adjusted by the physician according to the customary rules and procedures. It depends, for example, on the compound of the formula Ia or Ib administered and its potency and duration of action, on the nature and severity of the individual syndrome, on the sex, age, weight and the individual responsiveness of the human or animal to be treated, on whether the treatment is acute or chronic or prophylactic, or on whether further pharmaceutical active compounds are administered in addition to the compound of the formula Ia or Ib. Normally, in the case of administration to an adult weighing about 75 kg, a dose of from about 0.1 mg to about 100 mg per kg per day, preferably from about 1 mg to about 10 mg per kg per day (in each case in mg per kg of body weight), is sufficient. The daily dose can be administered in the form of a single dose or divided into a number of individual doses, for example two, three or four individual doses. The administration can also be carried out continuously, for example by continuous injection or infusion. Depending on the circumstances of the specific case, it may be necessary to deviate upward or downward from the indicated dosages.

Besides as a pharmaceutical active compound in human medicine and veterinary medicine, the compounds of the formulae Ia and Ib can also be employed as an aid in biochemical investigations or as a scientific tool or for diagnostic purposes, for example in in vitro diagnoses of biological samples, if an inhibition of renin is intended. The compounds of the formulae Ia and Ib and their salts can also be used as intermediates, for example for the preparation of further pharmaceutical active substances.

The following examples illustrate the invention.

When compounds prepared in the examples which contain a basic group, were purified by preparative high pressure liquid chromatography (HPLC) on reversed phase (RP) column material and, as customary, the eluent was a gradient mixture of water and acetonitrile (ACN) containing trifluoroacetic acid (TFA), they were in general obtained in the form of an acid addition salt with trifluoroacetic acid, depending on the details of the workup such as the lyophilization conditions. Such contained trifluoroacetic acid, whose amount can vary and can be up to about two equivalents of acid in the case of a compound containing two basic groups, for example, is not specified in the names in the headings of the examples and not depicted in the structural formulae, but indicated in the description of the examples. This applies accordingly to compounds which were obtained in the form of another acid addition salt such as an acid addition salt with hydrochloric acid, whose amount can likewise vary and can be up to about two equivalents of acid in the case of a compound containing two basic groups, for example, and which is not specified in the names in the headings of the examples and not depicted in the structural formulae, but indicated in the description of the examples.

Characterization of the Compounds

The prepared compounds were in general characterized by spectroscopic data and chromatographic data, in particular mass spectra (MS) and HPLC retention times (Rt; in min) which were obtained by combined analytical HPLC/MS characterization (LC/MS), and nuclear magnetic resonance (NMR) spectra, by melting points or decomposition points (Mp, in ° C.) and/or by optical rotations ($\alpha$, i.e. $[\alpha]_D^{20}$, in ° (degree) at the specified concentration c (in g/100 ml)). Unless specified otherwise, $^1$H-NMR spectra were recorded at 400 MHz and in DMSO-$D_6$ as solvent. In the NMR characterization, the chemical shift $\delta$ (in ppm), the number of hydrogen atoms and the multiplicity (s: singlet, d: doublet, dd: double doublet, t: triplet, dt: double triplet, q: quartet, m: multiplet; br: broad) of the peaks are given. In the MS characterization, in general the mass number (m/z) of the peak of the molecular ion (M, for example $M^+$) or of a related ion such as the ion M+1 (protonated molecular ion $MH^+$, i.e. $M+1^+$), which was formed depending on the ionization method used, is given. Generally, the ionization method was electrospray ionization (ESI). The particulars of the LC/MS methods used were as follows.

LC/MS Method LC1

Column: Waters Acquity BEH C18, 50×2.1 mm, 1.7 µm; flow: 1.0 ml/min; eluent A: water+0.05% TFA; eluent B: ACN+0.035% TFA; gradient: from 98% A+2% B to 0% A+100% B within 1.6 min, then 0% A+100% B for 1.5 min, then to 98% A+2% B within 3.0 min; MS ionization method: $ESI^+$ LC/MS Method LC2

Column: Waters XBridge C18, 30×4.6 mm, 3 µm; flow: 1.0 ml/min; eluent A: water+0.1% formic acid; eluent B: ACN+0.01% formic acid; gradient: from 95% A+5% B to 0% A+100% B within 5.5 min, then 0% A+100% B for 2 min, then to 95% A+5% B within 8 min; MS ionization method: $ESI^+$ LC/MS Method LC3

Column: YMC J'sphere ODS H80, 20×2.1 mm, 4 µm; flow: 1 ml/min; eluent A: water+0.05% TFA; eluent B: ACN; gradient: from 96% A+4% B to 5% A+95% B within 2 min, then 5% A+95% B for 0.4 min, then to 96% A+4% B within 0.05 min; MS ionization method: $ESI^+$ LC/MS Method LC4

Column: Luna C18, 10×2 mm, 3 µm; flow: 1.1 ml/min; eluent A: water+0.05% TFA; eluent B: ACN+0.05% TFA; gradient: from 93% A+7% B to 5% A+95% B within 1.2 min, then 5% A+95% B for 0.2 min, then to 93% A+7% B within 0.05 min; MS ionization method: $ESI^+$

ABBREVIATIONS

ACN acetonitrile
DBU 1,8-diazabicyclo[5.4.0]undec-7-ene
DCM dichloromethane
DMF dimethylformamide
DMSO dimethyl sulfoxide
EA ethyl acetate
EDIA ethyl-diisopropylamine
HEP n-heptane
MOH methanol
NMP N-methylpyrrolidin-2-one
TBTU O-(benzotriazol-1-yl)-N,N,N',N'-tetramethyluronium tetrafluoroborate
TFA trifluoroacetic acid
THF tetrahydrofuran Example 1

[2-(3-Fluoro-2-methyl-benzyl)-1-phenyl-indolizin-3-yl]-piperazin-1-yl-methanone

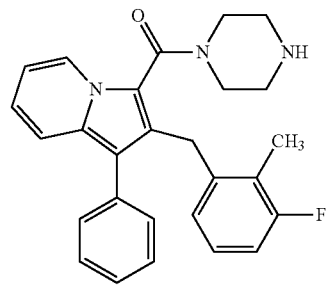 [SMILES: Cc1c(F)cccc1Cc1c(-c2ccccc2)c2ccccn2c1C(=O)N1CCNCC1]

Step 1: 1-Chloro-3-(3-fluoro-2-methyl-phenyl)-propan-2-one 0.867 g (35.67 mmol) of magnesium turnings were dried and suspended in 17 ml of anhydrous THF under argon. A solution of 1,2-dibromoethane (0.14 ml, 1.62 mmol) and 2-bromo-6-fluoro-toluene (6.74 g, 35.67 mmol) in 17 ml of anhydrous THF was then added dropwise so as to maintain a gentle reflux. Once the magnesium had been consumed, copper(I) iodide (0.432 g, 2.27 mmol) was then added, followed by a solution of epichlorohydrine (3.00 g, 32.42 mmol) in DMF (8 ml). The mixture was stirred for 3.5 h at room temperature and then quenched with a saturated solution of ammonium chloride (120 ml). The organic layer was separated, and the aqueous phase was extracted twice with EA. The combined organic phases were washed twice with a saturated solution of ammonium chloride, dried over sodium sulfate, filtered and evaporated to dryness. The product was purified by chromatography on silica gel (cyclohexane/EA, from 100:0 to 90:10) to give 6.89 g of 1-chloro-3-(3-fluoro-2-methyl-phenyl)-propan-2-ol. 3.92 g (16.23 mmol) of this alcohol were dissolved in DCM under argon, and 1,1,1-triacetoxy-1,1-dihydro-1,2-benziodoxol-3(1H)-one (Dess-Martin periodinane reagent; 7.57 g, 16.23 mmol) was added. The mixture was stirred at room temperature overnight and then diethyl ether (150 ml) was added. The mixture was washed three times with 1 N hydrochloric acid (70 ml) and twice with a saturated solution of sodium chloride, and extracted with ether. The extracts were dried over sodium sulfate, filtered and evaporated to dryness. 2.69 g of the title compound were obtained as a white powder.

Step 2: 1-Bromo-3-(3-fluoro-2-methyl-phenyl)-propan-2-one

The compound of step 1 (3.20 g, 15.95 mmol) was dissolved in acetone (70 ml), and lithium bromide (11.08 g, 127.59 mmol) was added. The mixture was stirred overnight. The solvent was evaporated, the resulting solid was dissolved in EA and the solution washed twice with water followed by a saturated solution of sodium chloride, dried over sodium sulfate, filtered and evaporated to dryness. 3.66 g of the title compound were obtained as a white powder.

Step 3: 2-(3-Fluoro-2-methyl-benzyl)-1-phenyl-indolizine

The compound of step 2 (1.50 g, 6.12 mmol) and 2-benzyl-pyridine (2.071 g, 12.24 mmol) were dissolved in acetone (30 ml) and the mixture was stirred under reflux overnight. The mixture was concentrated to dryness and the residue was purified by chromatography on silica gel (cyclohexane) to give 0.653 g of the title compound.

Step 4: [2-(3-Fluoro-2-methyl-benzyl)-1-phenyl-indolizin-3-yl]-piperazin-1-yl-methanone The compound of step 3 (0.635 g, 2.01 mmol) was dissolved in DCM (5 ml) under argon and cooled at 0° C. Pyridine (0.16 ml, 2.01 mmol) and triphosgene (0.598 g, 2.01 mmol) were added, and the mixture was stirred at room temperature for 80 min. The mixture was then added dropwise to a solution of 1-tert-butoxycarbonyl-piperazine (1.50 g, 8.05 mmol) and triethylamine (1.12 ml, 8.05 mmol) in DCM (15 ml) cooled to 0° C. After stirring at room temperature overnight, the mixture was diluted with 1 N hydrochloric acid and extracted with DCM. The extracts were washed with a saturated solution of sodium hydrogencarbonate and twice washed with saturated solution of sodium chloride. The organic phase was dried over sodium sulfate, filtered and evaporated to dryness. The residue was purified by silica gel chromatography with DCM/MOH (from 100:0 to 98:2) and subsequent silica gel chromatography with cyclohexane/EA (from 100:0 to 70:30) to give 0.815 g of 4-[2-(3-fluoro-2-methyl-benzyl)-1-phenyl-indolizin-3-carbonyl]-piperazine-1-carboxylic acid tert-butyl ester as a light pink powder. For removal of the tert-butoxycarbonyl group and conversion into the hydrochloride, 0.689 g of the obtained product were dissolved in DCM (10 ml), the solution cooled to 0° C. and saturated with gaseous hydrogen chloride. After stirring for 1 h at 0° C., the mixture was evaporated to dryness. The residue was triturated with diethyl ether, filtered, washed with diethyl ether and dried under reduced pressure to give 0.53 g of the title compound in the form of [2-(3-fluoro-2-methyl-benzyl)-1-phenyl-indolizin-3-yl]-piperazin-1-yl-methanone hydrochloride as an off-white powder with the following characteristics:

Mp: 263° C.
LC/MS (Method LC 1): m/z=428 [MH$^+$]; Rt=1.10 min
$^1$H-NMR: δ (ppm)=2.00 (s, 3H), 2.85 (m, 2H), 3.11 (m, 2H), 3.48 (m, 2H), 3.76 (m, 2H), 4.12 (s, 2H), 6.68 (d, 1H), 6.88 (t, 1H), 6.95 (m, 2H), 7.02 (m, 1H), 7.35 (m, 3H), 7.49 (m, 3H), 8.32 (d, 1H), 9.40 (br s, 1H)

Example 2

[1-Cyclohexyl-2-(3-fluoro-2-methyl-benzyl)-indolizin-3-yl]-piperazin-1-yl-methanone

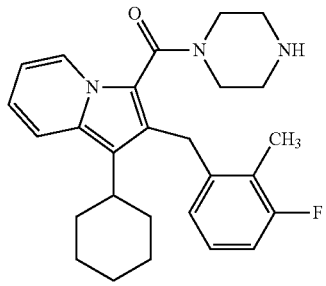 [SMILES: Cc1c(F)cccc1Cc1c(C2CCCCC2)c2ccccn2c1C(=O)N1CCNCC1]

Step 1: 2-Cyclohexylmethyl-pyridine

Following a modified version of the procedure given in J. M. Ontoria et al., Bioorg. Med. Chem. Lett. 16 (2006), 4026, a solution of 2-methyl-pyridine (0.50 g, 5.37 mmol) in 10 ml of anhydrous THF was cooled to −78° C. under an atmosphere of argon. n-Butyllithium (2.36 ml of a 2.5 M solution in hexane, 5.91 mmol) was added dropwise and the solution was stirred at −78° C. for 1 h. 3-bromo-cyclohexene (0.68 ml, 5.91 mmol) was added then dropwise and the temperature was allowed to rise to ambient temperature over 3 h. After stirring overnight, the mixture was quenched by addition of 20 ml of water and extracted twice with EA. The combined organic phases were washed with a saturated solution of sodium chloride, dried over sodium sulfate, filtered and evaporated to dryness to give 0.436 g of 2-(cyclohex-2-en-1-ylmethyl)-pyridine as an orange oil. This product was dissolved in 8.4 ml of ethanol, 5% palladium on charcoal (50% in water; 0.087 g) was added, and the mixture was hydrogenated under a hydrogen pressure of 3.2 bar for 4 h at room temperature. The catalyst was then filtered off and the filtrate was evaporated to dryness under reduced pressure to give 0.415 g of the title compound as an oil.

Step 2: 1-Cyclohexyl-2-(3-fluoro-2-methyl-benzyl) indolizine

The compound of step 1 (0.415 g, 2.37 mmol) and the compound of step 2 of example 1 (0.58 g, 2.37 mmol) were dissolved in 15 ml of acetone and the solution was stirred under reflux for 36 h. The solution was evaporated to dryness and the solid (0.92 g) dissolved in 10 ml of isopropanol. Sodium carbonate (0.70 g, 6.57 mmol) was added, the mixture was stirred under reflux for 2 h and then evaporated to dryness under reduced pressure. The residue was taken up in DCM and water, and the aqueous phase was extracted twice with DCM. The combined organic phases were dried over sodium sulfate, filtered and evaporated to dryness under reduced pressure. The residue was purified by chromatography on silica gel (HEP/EA, 100:0, then 70:30) to give 0.489 g of the title compound as a thick yellow oil.

Step 3: [1-Cyclohexyl-2-(3-fluoro-2-methyl-benzyl)-indolizin-3-yl]-piperazin-1-yl-methanone The compound of step 2 (0.488 g, 1.52 mmol) was dissolved in DCM (15.2 ml) under argon and cooled at 0° C. Pyridine (0.12 ml, 1.52 mmol) and triphosgene (0.45 g, 1.52 mmol) were added and the mixture stirred at room temperature for 2 h. The mixture was then cooled to 0° C. and triethylamine (0.85 ml, 6.07 mmol) and 1-tert-butoxycarbonyl-piperazine (1.13 g, 6.07 mmol) were added. The mixture was stirred at room temperature overnight, then diluted with 1 N hydrochloric acid and extracted with DCM. The organic phases were washed with a saturated solution of sodium hydrogencarbonate and twice with a saturated solution of sodium chloride, dried over sodium sulfate, filtered and evaporated to dryness. The residue was purified by silica gel chromatography (cyclohexane/EA, 100:0, then 50:50) to give 0.686 g of 4-[1-cyclohexyl-2-(3-fluoro-2-methyl-benzyl)-indolizine-3-carbonyl]-piperazine-1-carboxylic acid tert-butyl ester as a beige foam. The obtained product was dissolved in 10 ml of DCM, the solution cooled to 0° C. under a nitrogen atmosphere and a solution of TFA (1.91 ml, 25.7 mmol) in 1.91 ml of DCM added. After stirring at room temperature overnight, the mixture was evaporated to dryness under reduced pressure and the residue two times admixed with toluene and evaporated to dryness again. The residue was purified by chromatography on silica gel (DCM/MOH, 9:1, containing 1% of ammonia) to give 0.600 g of [1-cyclohexyl-2-(3-fluoro-2-methyl-benzyl)-indolizin-3-yl]-piperazin-1-yl-methanone. For conversion into the hydrochloride, the obtained product was dissolved in 15 ml of DCM and a 4 N solution of hydrogen chloride in dioxane (0.69 ml, 2.77 mmol) was added. The solution was stirred for 1 h at room temperature and concentrated to dryness under reduced pressure. The solid was triturated three times with diethyl ether, filtered and dried in vacuo at 65° C. to give 0.422 g of the title compound in the form of [1-cyclohexyl-2-(3-fluoro-2-methyl-benzyl)-indolizin-3-yl]-piperazin-1-yl-methanone hydrochloride as an off-white powder with the following characteristics:

Mp: 317-318° C.

LC/MS (Method LC2): m/z=434.2 [MH$^+$]; Rt=4.10 min $^1$H-NMR: δ (ppm)=1.0-1.25 (m, 3H), 1.45 (m, 2H), 1.61 (m, 5H), 2.13 (s, 3H), 2.47 (m, 1H), 2.78 (m, 2H), 3.01 (m, 2H), 3.35 (m, 2H), 3.56 (m, 2H), 3.94 (s, 2H), 6.52 (m, 2H), 7.02 (m, 1H), 6.90 (m, 1H), 6.98 (m, 1H), 7.55 (d, 1H), 8.09 (d, 1H), 9.08 (br s, 2H)

Example 3

[2-(2-Chloro-6-fluoro-benzyl)-1-phenyl-indolizin-3-yl]-piperazin-1-yl-methanone

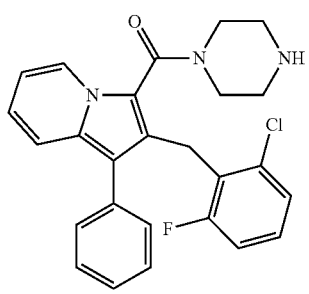 [SMILES: O=C(c1c(Cc2c(F)cccc2Cl)c(-c2ccccc2)c2ccccn12)N1CCNCC1]

Step 1: 1-Bromo-3-(2-chloro-6-fluoro-phenyl)-2-propanone

To a 2 M solution of trimethylsilyl-diazomethane in hexane (6.54 ml, 13.07 mmol) cooled to 0° C. under argon was added dropwise a solution of 2-chloro-6-fluoro-phenylacetyl chloride (1.23 g, 5.94 mmol) in 24 ml of a mixture of THF and ACN (1:1). The mixture was stirred at 0° C. for 5 h. Then 48% aqueous hydrobromic acid (5.91 ml, 52.28 mmol) was added dropwise and the solution was stirred at room temperature overnight. Then 40 ml of water were added. The aqueous phase was extracted twice with EA, and the combined organic phases were washed with water, a saturated solution of sodium hydrogencarbonate and brine, dried over sodium sulfate, filtered and evaporated to dryness under reduced pressure. The residue was purified by chromatography on silica gel (cyclohexane/EA, 100:0, then 95:5) to give 1.20 g of the title compound as a white powder having a melting point of 47° C.

Step 2: 2-(2-Chloro-6-fluoro-benzyl)-1-phenyl-indolizine

The compound of step 1 (1.17 g, 4.41 mmol) and 2-benzyl-pyridine (1.49 g, 8.82 mmol) were dissolved in acetone (15 ml) and the mixture was stirred under reflux overnight. The mixture was concentrated to dryness and the residue was purified by chromatography on silica gel (DCM/MOH, 100:0, then 95:5) to give 1.13 g of the title compound.

Step 3: 4-[2-(2-Chloro-6-fluoro-benzyl)-1-phenyl-indolizine-3-carbonyl]-piperazine-1-carboxylic acid tert-butyl ester The compound of step 2 (0.576 g, 1.72 mmol) was dissolved in DCM (8 ml) under argon and cooled at 0° C. Pyridine (0.14 ml, 1.72 mmol) and triphosgene (0.509 g, 1.72 mmol) were added and the mixture was stirred at room temperature for 2 h. The mixture was then added dropwise to a solution of 1-tert-butoxycarbonyl-piperazine (1.28 g, 6.85 mmol) and triethylamine (0.86 ml, 6.85 mmol) in DCM (8 ml) cooled to 0° C. The mixture stirred at room temperature overnight, then diluted with 1 N hydrochloric acid and extracted with DCM. The combined organic phases were washed with a saturated sodium hydrogencarbonate solution and twice with a saturated sodium chloride solution, were dried over sodium sulfate, filtered and evaporated to dryness. The residue was purified by silica gel chromatography (cyclohexane/EA, 100:0, then 75:25) to give 0.895 g of the title compound as an off-white powder.

Step 4: [2-(2-Chloro-6-fluoro-benzyl)-1-phenyl-indolizin-3-yl]-piperazin-1-yl-methanone The compound of step 3 (0.886 g, 1.62 mmol) was dissolved in DCM (6.5 ml). The solution was cooled at 0° C. and a 4 N solution of hydrogen chloride in dioxane (2.02 ml, 8.08 mmol) was added. After stirring overnight at room temperature, the mixture was concentrated to dryness. The residue was triturated several times with diethyl ether, filtered, rinsed with diethyl ether and dried in a vacuo at 65° C. to give 0.70 g of the title compound in the form of [2-(2-chloro-6-fluoro-benzyl)-1-phenyl-indolizin-3-yl]-piperazin-1-yl-methanone hydrochloride as an off-white powder with the following characteristics:

Mp: 304° C.

LC/MS (method LC1): m/z=448 [MH$^+$]; Rt=1.05 min $^1$H-NMR: δ (ppm)=3.01 (m, 2H), 3.11 (m, 2H), 3.35 (m, 6H), 3.73 (m, 2H), 4.21 (s, 2H), 6.73 (t, 1H), 6.88 (dd, 1H), 6.98 (t, 1H), 7.10 (d, 1H), 7.18 (q, 1H), 7.38 (m, 3H), 8.23 (d, 1H), 9.35 (br s, 2H)

Example 4

2-(3-Fluoro-2-methyl-benzyl)-1-phenyl-3-(piperazine-1-carbonyl)-indolizine-7-carboxylic acid methylamide

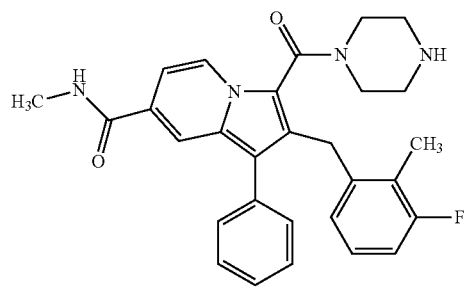 [SMILES: CNC(=O)c1ccn2c(C(=O)N3CCNCC3)c(Cc3cccc(F)c3C)c(-c3ccccc3)c2c1]

Step 1: Methyl 2-benzyl-pyridine-4-carboxylate

To 35 ml of anhydrous DMF under argon in a sealed tube were added tripotassium phosphate (9.28 g, 43.71 mmol), 2-dicyclohexylphosphino-2',6'-dimethoxy-biphenyl (SPhos, 0.239 g, 0.58 mmol), palladium(II) acetate (0.065 g, 0.29 mmol) and then methyl 2-chloro-pyridine-4-carboxylate (2.50 g, 14.57 mmol) and B-benzyl-9-borabicyclo[3.3.1]nonane (6.80 g, 32.05 mmol). The mixture was heated overnight at 60° C. After cooling to room temperature, the mixture was diluted into 200 ml of EA, the solution washed three times with 100 ml of a 1 N sodium hydroxide solution and twice with 100 ml of brine. The organic phase was dried over sodium sulfate, filtered and evaporated to dryness under reduced pressure. The residue was then purified by chromatography on silica gel (cyclohexane/EA, 100:0, then 80:20) to give 2.784 g of the title compound as an orange oil.

Step 2: Methyl-2-(3-fluoro-2-methyl-benzyl)-1-phenyl-indolizine-7-carboxylate The compound of step 1 (1.555 g, 6.84 mmol) and the compound of example 1, step 2 (1.677 g, 6.84 mmol) were dissolved in 28.5 ml of acetone and the solution was heated to reflux overnight. The mixture was then evaporated to dryness under reduced pressure and the residue dissolved in 28.5 ml of isopropanol. Sodium carbonate (2.176 g, 20.53 mmol) was added and the mixture was heated at 105° C. with stirring for 2 h. The solids were filtered off and the filtrate was evaporated to dryness under reduced pressure. The residue was purified by chromatography on silica gel (cyclohexane/EA, 100:0, then 95:5) to give 0.497 g of the title compound as a yellow solid melting at 55° C.

Step 3: Methyl-2-(3-fluoro-2-methyl-benzyl)-3-formyl-1-phenyl-indolizine-7-carboxylate To phosphorus oxychloride (0.35 ml, 3.82 mmol) cooled at 0° C. under argon, was added dropwise anhydrous DMF (0.34 ml, 4.46 mmol) and the mixture was stirred for 5 min forming a precipitate. 1.5 ml of DMF were added and stirring was continued at 0° C. for 15 min. To this mixture was added dropwise a solution of the compound of step 2 (0.476 g, 1.27 mmol) in 5 ml of DMF, and the mixture was heated at 60° C. for 1.5 h and then stirred at room temperature overnight. A solution of sodium acetate (0.837 g) in 6.5 ml water was added, the mixture was heated at 50° C. for 1 h, and evaporated to dryness under reduced pressure. The residue was dissolved in EA, the solution was washed with a saturated solution of sodium hydrogencarbonate, water and brine, dried over sodium sulfate, filtered and evaporated to dryness under reduced pressure. The residue was purified by chromatography on silica gel (cyclohexane/EA, 100:0, then 90:10) to give 0.297 g of the title compound.

Step 4: 2-(3-fluoro-2-methyl-benzyl)-7-methoxycarbonyl-1-phenyl-indolizine-3-carboxylic acid The compound of step 3 (0.293 g, 0.73 mmol) was suspended in 4 ml of tert-butanol and cooled to 0° C. To this suspension were added a solution of sodium dihydrogenphosphate (0.263 g, 2.19 mmol) in 1 ml of water, a 2 M solution of 2-methyl-2-butene in THF (2.19 ml, 4.38 mmol) and sodium chlorite (0.124 g, 1.09 mmol) in small portions. After stirring at room temperature for 18 h, once more a solution of sodium dihydrogenphosphate (0.263 g, 2.19 mmol) in 2 ml water, a 2 M solution of 2-methyl-2-butene in THF (2.19 ml, 4.38 mmol) and sodium chlorite (0.124 g, 1.09 mmol) were added again and stirring was continued for an additional 48 h. Then 30 ml of a 1:1 mixture of brine and EA were added, the organic phase was separated, and the aqueous phase was extracted with EA. The combined organic phases were washed with brine, dried over sodium sulfate, filtered and evaporated to dryness under reduced pressure to give 0.420 g of the crude title compound as a yellow powder which was directly used in the next step.

Step 5: 3-(4-tert-Butoxycarbonyl-piperazine-1-carbonyl)-2-(3-fluoro-2-methyl-benzyl)-1-phenyl-indolizine-7-carboxylic acid methyl ester To a solution of the crude compound obtained in step 4 (0.420 g, 0.69 mmol), 1-tert-butoxycarbonyl-piperazine (0.142 g, 0.76 mmol) and triethylamine (0.48 ml, 2.78 mmol) in 3.5 ml of DMF cooled at 0° C., was added TBTU (0.490 g, 1.53 mmol) in small portions, and the mixture was stirred at room temperature overnight. 10 ml of EA and 20 ml of brine were then added, the aqueous phase was separated and extracted twice with EA. The combined organic phases were washed with water, 1 N hydrochloric acid, water, an saturated solution of sodium hydrogencarbonate and brine, dried over sodium sulfate, filtered and evaporated to dryness under reduced pressure. The residue was purified by chromatography on silica gel (cyclohexane/EA, 100:0, then 70:30) to give 0.162 g of the title compound as a beige solid.

Step 6: 3-(4-tert-Butoxycarbonyl-piperazine-1-carbonyl)-2-(3-fluoro-2-methyl-benzyl)-1-phenyl-indolizine-7-carboxylic acid The compound of step 5 (0.159 g, 0.27 mmol) was dissolved in 2 ml of dioxane, and a solution of lithium hydroxide hydrate (0.034 g, 0.82 mmol) in 0.8 ml water was added. The solution was stirred at 50° C. overnight. The solvents were then evaporated under reduced pressure, the residue was dissolved in 6 ml of water and acidified to pH 1 with 1 N hydrochloric acid. The product was filtered off, dissolved in EA and the solution washed with brine. The organic phase was dried over sodium sulfate, filtered and evaporated to give 0.139 g of the title compound as a light-brown powder.

Step 7: 4-[2-(3-fluoro-2-methyl-benzyl)-7-methyl-carbamoyl-1-phenyl-indolizine-3-carbonyl]-piperazine-1-carboxylic acid tert-butyl ester The compound of step 6 (0.139 g, 0.24 mmol), methylamine hydrochloride (0.022 g, 0.32 mmol) and triethylamine (0.17 ml, 0.97 mmol) were dissolved in 2 ml of DMF and cooled to 0° C. TBTU (0.195 g, 0.61 mmol) was added and the solution was stirred at room temperature overnight. Water (8 ml) was then added and the mixture was extracted three times with EA. The combined organic phases were washed with 1 N hydrochloric acid, water, a saturated solution of sodium hydrogencarbonate and brine, dried over sodium sulfate, filtered and evaporated to dryness under reduced pressure. The residue was purified by chromatography on silica gel (DCM/MOH, 100:0, then 96:4) to give 0.065 g of the title compound as a beige solid.

Step 8: 2-(3-Fluoro-2-methyl-benzyl)-1-phenyl-3-(piperazine-1-carbonyl)-indolizine-7-carboxylic acid methylamide The compound of step 7 (0.065 g, 0.11 mmol) was dissolved in 1.1 ml of DCM and cooled to 0° C. and a 4 N solution of hydrogen chloride in dioxane (0.54 ml, 2.20 mmol) was added. The mixture was stirred at room temperature overnight and then evaporated to dryness under reduced pressure. The obtained solid was triturated several times with diethyl ether and dried in vacuo at 40° C. 0.053 g of the title compound were obtained in the form of 2-(3-fluoro-2-methyl-benzyl)-1-phenyl-3-(piperazine-1-carbonyl)-indolizine-7-carboxylic acid methylamide hydrochloride as a light yellow solid with the following characteristics:

Mp: 205° C.
LC/MS (method LC1): m/z=485 [MH$^+$]; Rt=0.94 min
$^1$H-NMR: δ (ppm)=1.85 (s, 3H), 2.68 (d, 3H), 2.73 (m, 2H), 3.03 (m, 2H), 3.39 (m, 2H), 3.59 (m, 2H), 4.0 (s, 2H), 5.57 (d, 1H), 6.81 (t, 1H), 6.92 (q, 1H), 7.09 (dd, 1H), 7.30 (m, 3H), 7.39 (m, 2H), 7.89 (d, 1H), 8.08 (dd, 1H), 8.46 (dd, 1H), 9.04 (br s, 2H)

Example 5

[2-(3-Fluoro-2-methyl-benzyl)-1-phenyl-indolizin-3-yl]-[(S)-3-(2-hydroxy-ethyl)-piperazin-1]-yl-methanone

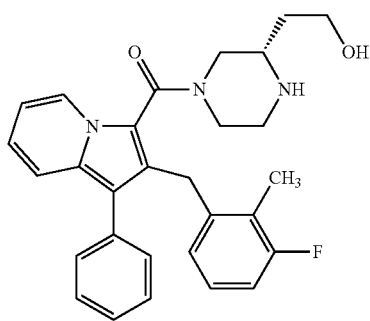 [SMILES: Cc1c(F)cccc1Cc1c(-c2ccccc2)c2ccccn2c1C(=O)N1CCN[C@@H](CCO)C1]

Step 1: (S)-4-Benzyl-2-(2-hydroxy-ethyl)-piperazine-1-carboxylic acid tert-butyl easter Di-tert-butyl dicarbonate (8.737 g, 40.3 mmol) was added to a solution of (S)-4-benzyl-piperazine-2-ethanol (prepared from methyl N-benzyl-glycinate and N-tert-butoxycarbonyl-L-aspartic acid β-methyl ester according to WO 2005/026177; 5.88 g, 26.69 mmol) in 130 ml of DCM. The solution was stirred at room temperature overnight and then evaporated to dryness under reduced pressure. The residue was purified by chromatography on silica gel (cyclohexane/EA, 100:0, then 70:30) to give 6.711 g of the title compound as a colorless oil.

Step 2: (S)-2-(2-hydroxy-ethyl)-piperazine-1-carboxylic acid tert-butyl ester

To a solution of the compound of step 1 (6.675 g, 20.83 mmol) in 100 ml of ethanol was added 0.293 g of 20% palladium hydroxide on charcoal and the solution was hydrogenated under a hydrogen pressure of 4 bar at room temperature overnight. The catalyst was filtered off and the filtrate was evaporated to dryness to give 4.636 g of the title compound as a grey oil.

Step 3: (S)-2-[2-(tert-butyl-dimethyl-silyloxy)-ethyl)-piperazine-1-carboxylic acid tert-butyl ester Tert-butyl-dimethyl-silyl chloride (3.62 g, 24.02 mmol) and imidazole (3.27 g, 48.03 mmol) were added to a solution of the compound of step 2 (4.609 g, 20.01 mmol) in 75 ml of DCM and the resulting solution was stirred at room temperature for 3 h. The mixture was washed with 50 ml of water and then 50 ml of brine. The aqueous phase was extracted once with DCM. The combined organic phases were dried over sodium sulfate, filtered and evaporated under reduced pressure to give 6.90 g of the title compound as a pale yellow oil.

Step 4: (S)-2-[2-(tert-Butyl-dimethyl-silyloxy)-ethyl]-4-[2-(3-fluoro-2-methyl-benzyl)-1-phenyl-indolizine-3-carbonyl]-piperazine-1-carboxylic acid tert-butyl ester The compound of example 1, step 3 (1.00 g, 3.17 mmol) was dissolved in 15 ml of DCM and cooled to 0° C. To this solution was added pyridine (0.26 ml, 3.17 mmol) and a 20% solution of phosgene in toluene (1.67 ml, 3.17 mmol) and the mixture was stirred for 2.5 h at room temperature. This solution was then added dropwise to a solution of the compound of step 3 (1.202 g, 3.49 mmol) in 25 ml of DCM containing triethylamine (0.44 ml, 3.49 mmol) and the mixture stirred overnight at room temperature. DCM (25 ml) was added and the solution was washed with 25 ml of 0.5 N hydrochloric acid, 25 ml of a saturated solution of sodium hydrogencarbonate and 25 ml of brine. The organic phase was dried over sodium sulfate, filtered and evaporated to dryness under reduced pressure. The residue was purified by chromatography on silica gel (cyclohexane/EA, 85:15, then 80:20) to give 1.33 g of the title compound as an off-white powder melting at 70° C.

Step 5: (S)-4-[2-(3-fluoro-2-methyl-benzyl)-1-phenyl-indolizine-3-carbonyl]-2-(2-hydroxy-ethyl)-piperazine-1-carboxylic acid tert-butyl ester A 1 M solution of tetrabutylammonium fluoride in THF (2.82 ml, 2.82 mmol) was added to a solution of the compound of step 4 (1.29 g, 1.88 mmol) in 7.5 ml of THF cooled to 0° C. under argon. The mixture was stirred at room temperature for 2 h and then 100 ml of a saturated solution of ammonium chloride were added. The solution was extracted twice with 50 ml each of EA, and the combined organic phases were washed with brine, dried over sodium sulfate, filtered and evaporated to dryness under reduced pressure. The residue was purified by chromatography on silica gel (DCM/MOH, 100:0, then 98:2) to give 1.069 g of the title compound as an off-white powder melting at 85° C.

Step 6: [2-(3-Fluoro-2-methyl-benzyl)-1-phenyl-indolizin-3-yl]-[(S)-3-(2-hydroxy-ethyl)-piperazin-1]-yl-methanone To a solution of the compound of step 5 (0.10 g, 0.17 mmol) in 1.75 ml of DCM cooled to 0° C. was added a 4 N solution of hydrogen chloride in dioxane (0.87 ml, 3.50 mmol). The mixture stirred at room temperature for 3.5 h and then evaporated to dryness. The obtained solid was triturated several times with diethyl ether and dried in vacuo at 60° C. to give 0.070 g of the title compound in the form of [2-(3-fluoro-2-methyl-benzyl)-1-phenyl-indolizin-3-yl]-[(S)-3-(2-hydroxy-ethyl)-piperazin-1]-yl-methanone hydrochloride as an off-white powder with the following characteristics:

Mp: 202° C.
LC/MS (method LC1): m/z=472 [MH$^+$]; Rt=1.07 min
$^1$H-NMR: δ (ppm)=1.68 (m, 2H), 2.0 (d, 3H), 2.95 (m, 1H), 3.21 (m, 3H), 3.50 (m, 3H), 3.85 (m, 1H), 4.10 (m, 3H), 4.86

(br s, 1H), 6.64 (m, 1H), 6.80 (dd, 1H), 6.97 (m, 3H), 7.48 (m, 6H), 8.30 (m, 1H), 9.21 (br s, 2H)
α=–0.291° (c=4.7 g/100 ml, MOH)

Example 6

2-{(S)-4-[2-(3-Fluoro-2-methyl-benzyl)-1-phenyl-indolizine-3-carbonyl]-piperazin-2-yl}-N-(tetrahydropyran-4-ylmethyl)-acetamide

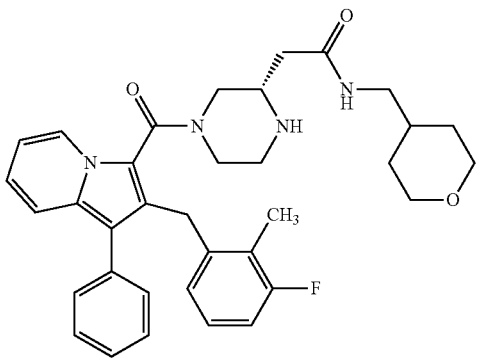 [SMILES: Cc1c(F)cccc1Cc1c(-c2ccccc2)c2ccccn2c1C(=O)N1CCN[C@@H](CC(=O)NCC2CCOCC2)C1]

Step 1: (S)-4-[2-(3-fluoro-2-methyl-benzyl)-1-phenyl-indolizine-3-carbonyl]-2-(2-oxo-ethyl)-piperazine-1-carboxylic acid tert-butyl ester To a solution of the compound of example 5, step 5 (0.955 g, 1.67 mmol) in 10 ml of DCM under argon was added 1,1,1-triacetoxy-1,1-dihydro-1,2-benziodoxol-3(1H)-one (7.78 g, 1.84 mmol). The mixture was stirred at room temperature for 3.5 h and then diluted with 40 ml of diethyl ether. The solution was washed three times with a 1 N solution of sodium hydroxide (15 ml) and twice with brine (15 ml). The organic phase was dried over sodium sulfate, filtered and evaporated to dryness under reduced pressure to give 0.965 g of the title compound as a green powder which was directly used in the next step.

Step 2: {(S)-1-tert-Butoxycarbonyl-4-[2-(3-fluoro-2-methyl-benzyl)-1-phenyl-indolizine-3-carbonyl]-piperazin-2-yl}-acetic acid The compound obtained in step 1 (0.960 g, 1.69 mmol) was suspended in 9.6 ml of tert-butanol and cooled to 0° C. A solution of sodium dihydrogenphosphate (0.607 g, 5.06 mmol) in 2.4 ml or water, a 2 M solution of 2-methyl-but-2-ene in THF (5.06 ml, 10.11 mmol) and sodium chlorite (0.286 g, 2.53 mmol) were then added and the mixture was stirred for 3.75 h. Brine (30 ml) was added and the mixture was extracted three times with EA. The combined organic phases were washed twice with 1 N hydrochloric acid and once with brine, dried over sodium sulfate, filtered and evaporated to dryness. The residue was purified by chromatography on silica gel (DCM/MOH, 100:0, then 96:4) to give 0.398 g of the title compound.

Step 3: (S)-4-[2-(3-Fluoro-2-methyl-benzyl)-1-phenyl-indolizine-3-carbonyl]-2-{[(tetrahydropyran-4-ylmethyl)-carbamoyl]-methyl}-piperazine-1-carboxylic acid tert-butyl ester To a stirred, ice-cold solution of 4-aminomethyl-tetrahydropyran (0.047 g, 0.40 mmol), EDIA (0.19 ml, 1.08 mmol) and the compound of step 2 (0.190 g, 0.27 mmol) was added TBTU (0.259 g, 0.81 mmol) in small portions. The solution was stirred at room temperature for 18 h. Then water (8 ml) was added and the mixture was extracted 3 times with EA. The combined organic phases were washed with 1 N hydrochloric acid, water, a saturated solution of sodium hydrogencarbonate and brine, dried over sodium sulfate, filtered and evaporated to dryness under reduced pressure. The residue was purified by chromatography on silica gel (cyclohexane/EA, 100:0, then 50:50) to give 0.117 g of the title compound as an orange gum.

Step 4: 2-{(S)-4-[2-(3-Fluoro-2-methyl-benzyl)-1-phenyl-indolizine-3-carbonyl]-piperazin-2-yl}-N-(tetrahydropyran-4-ylmethyl)-acetamide To a solution of the compound of step 3 (0.113 g, 0.17 mmol) in 1.65 ml of DCM cooled to 0° C. was added a 4 N solution of hydrogen chloride in dioxane (0.41 ml, 1.65 mmol). The mixture was stirred for 3 h at room temperature and then evaporated to dryness. The solid was triturated several times with diethyl ether and dried in vacuo at 40° C. to give 0.071 g of the title compound in the form of 2-{(S)-4-[2-(3-fluoro-2-methyl-benzyl)-1-phenyl-indolizine-3-carbonyl]-piperazin-2-yl}-N-(tetrahydropyran-4-ylmethyl)-acetamide hydrochloride with the following characteristics:
Mp: 147° C.
LC/MS (method LC1): m/z=583 [MH$^+$]; Rt=1.10 min
$^1$H-NMR: δ (ppm)=1.15 (m, 3H), 1.54 (m, 3H), 1.60 (m, 1H), 1.97 and 2.03 (two s, 1H), 2.51 (m, 2H), 2.98 (m, 5H), 3.2 (m, 4H), 3.81 (m, 4H), 4.15 (m, 2H), 6.60 (t, 1H), 6.78 (dd, 1H), 6.92 (m, 4H), 7.40 (m, 6H), 8.18 (m, 2H), 8.35 (m, 1H), 9.13 (br s, 2H)
α: –2.69° (c=0.346 g/100 ml, MOH)

Example 7

3-(2-{(S)-4-[2-(3-Fluoro-2-methyl-benzyl)-1-phenyl-indolizine-3-carbonyl]-piperazin-2-yl}-acetylamino)-2,2-dimethyl-propionamide

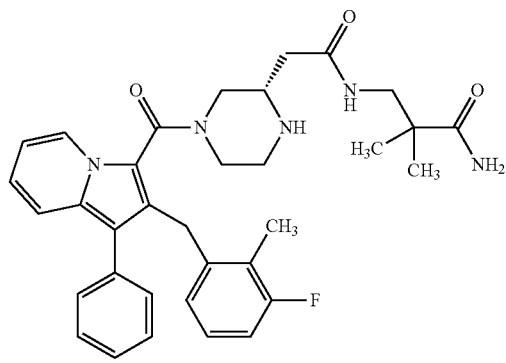 [SMILES: Cc1c(F)cccc1Cc1c(-c2ccccc2)c2ccccn2c1C(=O)N1CCN[C@@H](CC(=O)NCC(C)(C)C(N)=O)C1]

Step 1: [(S)-4-Benzyloxycarbonyl-1-tert-butoxycarbonyl-piperazin-2-yl]-acetic acid (S)-2-(2-Hydroxy-ethyl)-piperazine-1,4-dicarboxylic acid 4-benzyl ester 1-tert-butyl ester (cf. WO 96/31501; S. Fustero et al., Org. Lett. 9 (2007), 5283; 2.862 g, 7.85 mmol) was dissolved in 78.5 ml of DCM and pyridinium dichromate (14.772 g, 39.27 mmol) was added. The mixture was stirred at room temperature overnight, then diluted into brine (330 ml) and extracted three times with EA (70 ml). The combined organic phases were washed with water (300 ml), filtered over diatomaceous earth, dried over sodium sulfate, filtered and evaporated to dryness under reduced pressure. The product was dissolved in EA and extracted three times with a 1 N solution of sodium hydroxide. The combined aqueous phases were acidified to pH 1 with 6 N hydrochloric acid, extracted with EA and the combined extracts were washed with water and brine, dried over sodium sulfate, filtered and evaporated to dryness. 2.226 g of the title compound were obtained as a thick colorless oil.

Step 2: (S)-2-Methoxycarbonylmethyl-piperazine-1, 4-dicarboxylic acid 4-benzyl ester 1-tert-butyl ester To a solution of the compound of step 1 (2.52 g, 6.66 mmol) in 45 ml of acetone were added potassium carbonate (5.522 g, 39.96 mmol) and iodomethane (1.24 ml, 19.98 mmol) and the solution was stirred at room temperature overnight. The mixture was filtered and the filtrate was concentrated to dryness. The residue was dissolved in EA, washed twice with brine, dried over sodium sulfate, filtered and evaporated under reduced pressure. The residue was purified by chromatography on silica gel (cyclohexane/EA, 100:0, then 85:15) to give 2.334 g of the title compound as a colorless oil.

Step 3: (S)-2-Methoxycarbonylmethyl-piperazine-1-carboxylic acid tert-butyl ester To the compound of step 2 (2.317 g, 5.90 mmol) in 40 ml of MOH was added 0.063 g of 10% palladium on charcoal and the mixture was hydrogenated under a hydrogen pressure of 4 bar for 45 min at room temperature. The catalyst was filtered off and the filtrate evaporated to dryness under reduced pressure. 1.488 g of the title compound were obtained as a pale grey oil.

Step 4: (S)-4-[2-(3-Fluoro-2-methyl-benzyl)-1-phenyl-indolizine-3-carbonyl]-2-methoxycarbonylmethyl-piperazine-1-carboxylic acid tert-butyl ester To a solution of the compound of example 1, step 3 (1.32 g, 4.19 mmol) in 20 ml of DCM at 0° C. were added pyridine (0.34 ml, 4.19 mmol) and then a 20% solution of phosgene in toluene (2.20 ml, 4.19 mmol). The mixture was stirred at room temperature for 1.5 h and then added dropwise to an ice-cooled (0° C.) solution of the compound of step 3 (1.189 g, 4.60 mmol) and triethylamine (0.58 ml, 4.60 mmol) in 32 ml of DCM. The mixture was stirred at room temperature overnight, then diluted with 30 ml of DCM and washed twice with 1 N hydrochloric acid, twice with a saturated sodium hydrogencarbonate solution and twice with brine. The organic phase was dried over sodium sulfate, filtered and evaporated to dryness under reduced pressure. The residue was purified by chromatography on silica gel (cyclohexane/EA, 80:20, then 70:30) to give 1.44 g of the title compound as a pale yellow-green powder.

Step 5: {(S)-1-tert-Butoxycarbonyl-4-[2-(3-fluoro-2-methyl-benzyl)-1-phenyl-indolizine-3-carbonyl]-piperazin-2-yl}-acetic acid To a solution of the compound of step 4 (1.40 g, 2.33 mmol) in 15.5 ml of dioxane was added 3.5 ml of a 1 M aqueous solution of lithium hydroxide and the mixture was heated at 50° C. for 1 h. The solvents were evaporated under reduced pressure and the residue was dissolved in 45 ml of water. The solution was cooled to 0° C. and acidified to pH 2 with 5 N hydrochloric acid. The obtained suspension was extracted with EA and the combined organic phases were washed with brine, dried over sodium sulfate, filtered and evaporated to dryness. 1.37 g of the title compound were obtained as a green solid melting at 103-105° C.

Step 6: (S)-2-[(2-Carbamoyl-2-methyl-propylcarbamoyl)-methyl]-4-[2-(3-fluoro-2-methyl-benzyl)-1-phenyl-indolizine-3-carbonyl]-piperazine-1-carboxylic acid tert-butyl ester The compound of step 5 (0.176 g, 0.30 mmol) was dissolved in 2.5 ml of anhydrous DCM at 0° C. 3-Amino-2,2-dimethyl-propionamide (0.044 g, 0.38 mmol), EDIA (0.13 ml, 0.75 mmol) and TBTU (0.120 g, 0.38 mmol) were added and the solution was stirred at room temperature for 60 h. EA (15 ml) was then added and the solution was washed with water, 1 N hydrochloric acid, a saturated solution of sodium hydrogencarbonate and brine. The organic phase was dried over magnesium sulfate, filtered and evaporated under reduced pressure. The residue was purified by chromatography on silica gel (EA/MOH, 100:0, then 97:5, then 95:5) to give 0.188 g of the title compound as a greenish-brown wax.

Step 7: 3-(2-{(S)-4-[2-(3-Fluoro-2-methyl-benzyl)-1-phenyl-indolizine-3-carbonyl]-piperazin-2-yl}-acetylamino)-2,2-dimethyl-propionamide A 4 N solution of hydrogen chloride in dioxane (0.68 ml, 2.71 mmol) was added to a solution of the compound of step 6 (0.185 g, 0.27 mmol) in 2.7 ml of anhydrous DCM and the mixture stirred at room temperature for 2.5 h. After evaporation of the solvents, the obtained solid was triturated with anhydrous diethyl ether/DCM (9:1) and dried in vacuo at 45° C. to give 0.131 g of the title compound in the form of 3-(2-{(S)-4-[2-(3-fluoro-2-methyl-benzyl)-1-phenyl-indolizine-3-carbonyl]-piperazin-2-yl}-acetylamino)-2,2-dimethyl-propionamide hydrochloride as a light green powder with the following characteristics:

Mp: 174-176° C.
LC/MS (method LC1) m/z=584 [MH$^+$]; Rt=1.04 min
$^1$H-NMR: δ (ppm)=1.02 (s, 6H), 1.96 and 2.03 (two s, 3H), 2.60 (d, 2H), 3.20 (m, 5H), 3.52 (m, 3H), 3.95 (m, 2H), 4.11 (m, 2H), 6.61 (m, 1H), 6.9 (m, 4H), 7.32 (m, 3H), 7.40 (m, 3H), 7.96 (dd, 1H), 8.21 and 8.36 (two d, 1H), 9.30 (br s, 1H), 9.55 (br s, 1H)
α: −7.53° (c=0.425 g/100 ml, MOH)

Example 8

6-(3-Fluoro-2-methyl-benzyl)-5-phenyl-7-(piperazine-1-carbonyl)-pyrrolo[1,2-b]pyridazine-3-carboxylic acid methylamide

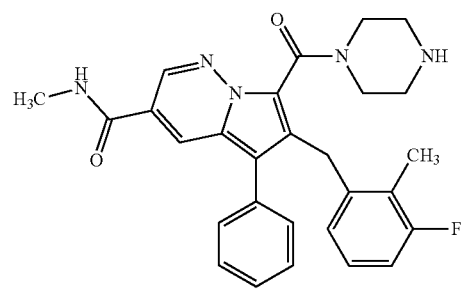 [SMILES: CNC(=O)c1cnn2c(C(=O)N3CCNCC3)c(Cc3cccc(F)c3C)c(-c3ccccc3)c2c1]

Step 1: 1-Fluoro-2-methyl-3-((E)-2-nitro-ethenyl)-benzene

A Knoevenagel condensation was carried out by stirring 3-fluoro-2-methyl-benzaldehyde (20.721 g, 150 mmol), nitromethane (48.75 ml, 900 mmol) and ammonium acetate (34.687 g, 450 mmol) in 300 ml of acetic acid at 115° C. for 3.5 h. The mixture was evaporated to dryness under reduced pressure and the residue was dissolved in 250 ml of EA. The solution was washed with water (250 ml), three times with a 1 N sodium hydroxide solution (125 ml) and with brine (125 ml), dried over magnesium sulfate, filtered and evaporated to dryness. 24.18 g of the title compound were obtained as a yellow solid.

Step 2: 1-Fluoro-2-methyl-3-(2-nitro-ethyl)-benzene

Analogously to the procedure described in A. K. Sinhababu et al., Tetrahedron Lett. 24 (1983), 227, to a solution of the compound of step 1 (16.85 g, 93.01 mmol) in isopropanol (275 ml) and chloroform (825 ml) were added dry silica gel (110 g) and then in small portions sodium borohydride (7.038 g, 186.02 mmol). The mixture was stirred at room temperature for 0.5 h, then cooled to 0° C. and quenched by slow addition of 10 ml of 5 N hydrochloric acid. After stirring for 10 min, the silica gel was filtered off and the filtrate was concentrated to dryness under reduced pressure. The residue was dissolved in 150 ml of DCM and the solution washed with water (75 ml) and brine (75 ml), dried over magnesium sulfate, filtered and evaporated to dryness to give 15.02 g of the title compound as a thick orange oil.

Step 3: 1-Fluoro-2-methyl-3-(2-nitro-3-phenyl-prop-2-en-1-yl)-benzene

The compound of step 2 (17.951 g, 98 mmol), benzaldehyde (10.43 ml, 102.90 mmol), n-butylamine (0.49 ml, 4.90 mmol) and acetic acid (0.28 ml, 4.90 mmol) in 49 ml of toluene were heated at 180° C. in a Dean-Stark apparatus for 6 h. After cooling to room temperature, the mixture was evaporated to dryness under reduced pressure. The residue was taken up in 49 ml of toluene, benzaldehyde (10.43 ml, 102.90 mmol), n-butylamine (0.49 ml, 4.90 mmol) and acetic acid (0.28 ml, 4.90 mmol) were added, and the mixture was heated at 180° C. in a Dean-Stark apparatus for 3 h. After cooling to room temperature, the mixture was evaporated to dryness under reduced pressure. The residue was triturated with 25 ml of diethyl ether/pentane (1:1). The solid was filtered off, rinsed with cyclohexane, and dissolved in 75 ml of DCM. The solution was dried with magnesium sulfate and evaporated to dryness to give 21.57 g of the title compound as a yellow solid melting at 111-112° C.

Step 4: 4-(3-Fluoro-2-methyl-benzyl)-3-phenyl-1H-pyrrole-2-carboxylic acid ethyl ester The compound of step 3 (21.45 g, 79.07 mmol) and ethyl isocyanoacetate (10.37 ml, 94.88 mmol) were dissolved in 225 ml of anhydrous THF under a nitrogen atmosphere at 5° C. and DBU (14.16 ml, 94.88 mmol) was added dropwise. The solution was stirred at room temperature for 18 h. Then 200 ml of water and 200 ml of EA were added. The organic phase was washed with 1 N hydrochloric acid (200 ml) and brine (150 ml), dried over magnesium sulfate, filtered and evaporated to dryness under reduced pressure. The residue was purified by chromatography on silica gel (cyclohexane/EA, 90:10, then 85:15) to give 16.68 g of the title compound as a yellow solid melting at 120-122° C.

Step 5: 1-Amino-4-(3-fluoro-2-methyl-benzyl)-3-phenyl-1H-pyrrole-2-carboxylic acid ethyl ester To a solution of the compound of step 4 (6.748 g, 20.00 mmol) in 60 ml of anhydrous DMF under a nitrogen atmosphere at 0° C. was added sodium hydride (60% in mineral oil, 0.960 g, 24 mmol) in small portions. After stirring for 10 min at 0° C., the mixture was allowed to warm to room temperature over 15 min. After cooling to 0° C. again, 0-(2,4-dinitro-phenyl)-hydroxylamine (cf. C. Legault et al., J. Org. Chem. 68 (2003), 7119; P. H. Boyle et al., ARKIVOC (2003) (vii), 67; 4.779 g, 24.00 mmol) was added in small portions and the mixture was stirred at room temperature for 1 h. Water (250 ml) and EA (250 ml) were added and the organic phase was washed twice with 125 ml each of a 1 N sodium hydroxide solution and 125 ml of brine, dried over magnesium sulfate, filtered and evaporated to dryness under reduced pressure. The residue was purified by chromatography on silica gel, first eluting with cyclohexane/DCM (40:60, then 20:80, then 0:100), then with DCM/EA (97.5:2.5, then 95:5) to give 6.33 g of the title compound as a beige solid melting at 87-88° C.

Step 6: 6-(3-Fluoro-2-methyl-benzyl)-4-oxo-5-phenyl-1,4-dihydro-pyrrolo[1,2-b]pyridazine-3-carboxylic acid ethyl ester To a solution of the compound of step 5 (6.290 g, 17.85 mmol) in 180 ml of anhydrous DMF under nitrogen were added ethyl 3,3-diethoxy-propanoate (10.42 ml, 53.55 mmol) and p-toluenesulfonic acid hydrate (0.509 g, 2.68 mmol), and the solution was heated at 90° C. for 1.5 h. After cooling to 60° C., DBU (13.32 ml, 89.24 mmol) was added dropwise and the mixture was stirred for 45 min at 60° C. The solution was then cooled to room temperature, water (600 ml) was added and the solution was extracted four times with EA (200 ml). The combined organic phases were washed with 0.5 N hydrochloric acid (300 ml) and brine (300 ml), dried over magnesium sulfate, filtered and evaporated to dryness under reduced pressure. The residue was triturated several times with cyclohexane and dried in vacuo at 50° C. 5.43 g of the title compound were obtained as a brown solid melting at 176-177° C.

Step 7: 4-Chloro-6-(3-fluoro-2-methyl-benzyl)-7-formyl-5-phenyl-pyrrolo[1,2-b]pyridazine-3-carboxylic acid ethyl ester Phosphorus oxychloride (24.5 ml, 268.00 mmol) was slowly added to the compound of step 6 (5.42 g, 13.40 mmol) followed by anhydrous DMF (5.18 ml, 67 mmol). The mixture was heated at 60° C. for 1 h and then concentrated to dryness. The residue was dissolved in DCM (200 ml) and the solution was added dropwise at room temperature to a saturated solution of sodium hydrogencarbonate. The mixture was stirred at room temperature for 1 h, then water (50 ml) and DCM (200 ml) were added, the phases were separated and the aqueous phase was extracted with DCM (100 ml). The combined organic phases were washed with a saturated solution of sodium hydrogencarbonate and brine, dried over sodium sulfate, filtered and evaporated to dryness. The residue was purified by chromatography on silica gel (cyclohexane/EA, 85:15, then 80:20) to give 5.19 g of the title compound as a yellow solid melting at 110-111° C.

Step 8: 4-Chloro-3-ethoxycarbonyl-6-(3-fluoro-2-methyl-benzyl)-5-phenyl-pyrrolo[1,2-b]pyridazine-7-carboxylic acid The compound of step 7 (5.15 g, 11.42 mmol) was suspended in tert-butanol (90 ml), and a 2 M solution of isobutene in THF (34.27 ml, 68.53 mmol), a solution of sodium dihydrogenphosphate (4.111 g, 34.27 mmol) in 25 ml of water and sodium chlorite (1.937 g, 17.13 mmol) were added. The mixture was stirred at room temperature for 2 h. Then brine (200 ml), water (50 ml), EA (400 ml) and DCM (100 ml) were added and the organic phase was separated, dried over magnesium sulfate, filtered and evaporated to dryness. The obtained solid was triturated several times with cyclohexane and dried in vacuo at 50° C. 5.23 g of the title compound were obtained as a yellow solid melting at 193-194° C.

Step 9: 7-(4-tert-Butoxycarbonyl-piperazine-1-carbonyl)-4-chloro-6-(3-fluoro-2-methyl-benzyl)-5-phenyl-pyrrolo[1,2-b]pyridazine-3-carboxylic acid ethyl ester The compound of step 8 (2.335 g, 5.00 mmol), 1-tert-butoxycarbonyl-piperazine (1.024 g, 5.50 mmol), EDIA (2.18 ml, 12.50 mmol) and TBTU (1.766 g, 5.50 mmol) in 50 ml of anhydrous DCM were stirred at room temperature for 1 h. The solution was then washed with 0.5 N hydrochloric acid (75 ml) and the aqueous phase was extracted with DCM (25 ml). The combined organic phases were washed with a saturated solution of sodium hydrogencarbonate (50 ml) and brine (50 ml), dried over magnesium sulfate, filtered and evaporated to dryness under reduced pressure. The residue was purified by chromatography on silica gel (cyclohexane/EA, 80:20, then 75:25) to give 3.01 g of the title compound as a yellow solid melting at 88-90° C.

Step 10: 7-(4-tert-Butoxycarbonyl-piperazine-1-carbonyl)-6-(3-fluoro-2-methyl-benzyl)-5-phenyl-pyrrolo[1,2-b]pyridazine-3-carboxylic acid ethyl ester The compound of step 9 (1.880 g, 2.96 mmol) in 29.6 ml of ethanol/THF (1:1) was hydrogenated under a hydrogen pressure of 2 bar for 3.5 h at room temperature in the presence of 0.315 g of 10% palladium on charcoal and triethylamine (0.62 ml, 4.44 mmol). The catalyst was filtered off and the filtrate was washed with brine (50 ml), dried with magnesium sulfate, filtered and concentrated to dryness under reduced pressure. 1.67 g of the title compound were obtained as a yellow solid.

Step 11: 7-(4-tert-Butoxycarbonyl-piperazine-1-carbonyl)-6-(3-fluoro-2-methyl-benzyl)-5-phenyl-pyrrolo[1,2-b]pyridazine-3-carboxylic acid The compound of step 10 (1.680 g, 2.80 mmol) was dissolved in 20 ml of dioxane and a 1 M aqueous solution of lithium hydroxide (4.30 ml, 4.30 mmol) was added. After stirring for 45 min at room temperature, the dioxane was evaporated under reduced pressure and 50 ml of water were added. The mixture was acidified to pH 2 with 5 N hydrochloric acid. The solid was filtered off, rinsed with water and dissolved in EA (100 ml). The solution was washed with water (50 ml) and brine (50 ml), dried over magnesium sulfate, filtered and evaporated to dryness under reduced pressure to give 1.64 g of the title compound which was directly used in the subsequent step.

Step 12: 4-[6-(3-Fluoro-2-methyl-benzyl)-3-methylcarbamoyl-5-phenyl-pyrrolo[1,2-b]pyridazine-7-carbonyl]-piperazine-1-carboxylic acid tert-butyl ester To a solution of the compound obtained in step 11 (0.286 g, 0.50 mmol) in 5 ml of DCM were added EDIA (0.26 ml, 1.50 mmol), methylamine hydrochloride (0.051 g, 0.75 mmol), a 2 M solution of methylamine in THF (2.5 ml, 0.50 mmol) and TBTU (0.107 g, 0.57 mmol). The solution was stirred at room temperature for 18 h, then diluted with DCM (15 ml), washed with 0.5 M hydrochloric acid, a saturated solution of sodium hydrogencarbonate and brine, dried over magnesium sulfate, filtered and evaporated to dryness under reduced pressure. The residue was purified by chromatography on silica gel (cyclohexane/EA, 30:70, then 20:80, then 10:90) to give 0.153 g of the title compound as a yellow solid melting at 153-154° C.

Step 13: 6-(3-Fluoro-2-methyl-benzyl)-5-phenyl-7-(piperazine-1-carbonyl)-pyrrolo[1,2-b]pyridazine-3-carboxylic acid methylamide To a solution of the compound of step 12 (0.150 g, 0.260 mmol) in 2.6 ml of DCM was added a 4 N solution of hydrogen chloride in dioxane (0.64 ml, 2.56 mmol). The mixture was stirred at room temperature for 5 h and then evaporated to dryness. The obtained solid was triturated several times with diethyl ether and dried in vacuo at 50° C. to give 0.118 g of the title compound in the form of 6-(3-fluoro-2-methyl-benzyl)-5-phenyl-7-(piperazine-1-carbonyl)-pyrrolo[1,2-b]pyridazine-3-carboxylic acid methylamide hydrochloride as a pale orange solid with the following characteristics:
Mp: 208-210° C.
LC/MS (method LC1): m/z=486 [MH$^+$]; Rt=0.93 min
$^1$H-NMR: δ (ppm)=1.85 (s, 3H), 2.71 (d, 3H), 2.92 (m, 4H), 3.49 (s, 2H), 3.65 (m, 2H), 4.02 (m, 2H), 6.69 (d, 1H), 6.88 (dd, 1H), 6.98 (dd, 1H), 7.37 (m, 3H), 7.45 (m, 2H), 8.22 (s, 1H), 8.60 (m, 2H), 9.06 (br s, 2H)

Example 9

[6-(3-Fluoro-2-methyl-benzyl)-5-phenyl-pyrrolo[1,2-b]pyridazin-7-yl]-piperazin-1-yl-methanone

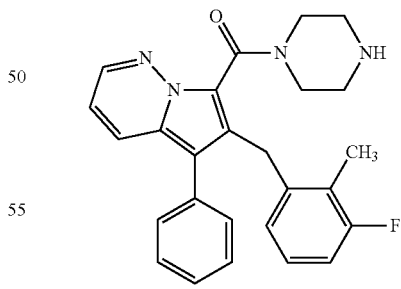

A mixture of the compound of example 8, step 11 (0.057 g, 0.10 mmol), copper powder (0.007 g, 0.10 mmol) and quinoline (0.40 ml) was plunged into an oil bath pre-heated at 170° C. for 1.25 h. After cooling to room temperature and evaporation of the volatiles under reduced pressure, the residue was dissolved in EA (10 ml) and the solution washed with water and brine, dried over magnesium sulfate, filtered and concentrated to dryness. The obtained orange oil was purified by chromatography on silica gel (DCM/MOH, 100:0, then 90:10). The product was dissolved in 2 ml of DCM and a 4 N solution of hydrogen chloride in dioxane (0.25 ml, 0.98 mmol) was added. After stirring at room temperature overnight, the solution was evaporated to dryness. The obtained solid was triturated several times with diethyl ether and dried in vacuo at 50° C. to give 0.016 g of the title compound in the form of [6-(3-fluoro-2-methyl-benzyl)-5-phenyl-pyrrolo[1,2-b]pyridazin-7-yl]-piperazin-1-yl-methanone hydrochloride as an orange solid with the following characteristics:

Mp: 140-142° C.
LC/MS (method LC1): m/z=429 [MH$^+$]; Rt=1.25 min
$^1$H-NMR: δ (ppm)=1.89 (s, 3H), 2.98 (m, 3H), 3.23 (s, 2H), 3.62 (m, 4H), 4.04 (m, 4H), 6.70 (d, 1H), 6.78 (m, 1H), 6.90 (t, 1H), 6.99 (dd, 1H), 7.32 (m, 3H), 7.41 (m, 2H), 7.89 (dd, 1H), 8.27 (d, 1H), 8.93 (br s, 2H)

Example 10

[6-(3-Fluoro-2-methyl-benzyl)-3-hydroxy-5-phenyl-pyrrolo[1,2-b]pyridazin-7-yl]-piperazin-1-yl-methanone

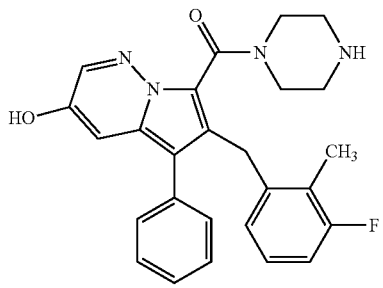 [SMILES: Cc1c(F)cccc1Cc1c(-c2ccccc2)c2cc(O)cnn2c1C(=O)N1CCNCC1]

Step 1: 4-[6-(3-Fluoro-2-methyl-benzyl)-3-(N-methoxy-N-methyl-carbamoyl)-5-phenyl-pyrrolo[1,2-b]pyridazin-7-carbonyl]-piperazine-1-carboxylic acid tert-butyl ester A solution of the compound of example 8, step 11 (1.002 g, 1.75 mmol), N,O-dimethylhydroxylamine hydrochloride (0.213 g, 2.19 mmol), EDIA (0.76 ml, 4.38 mmol) and TBTU (0.702 g, 2.19 mmol) in 15 ml of anhydrous DCM was stirred at room temperature for 4 h. DCM (15 ml) was then added and the solution was washed with 0.5 N hydrochloric acid (30 ml), a saturated solution of sodium hydrogencarbonate (15 ml) and brine (15 ml), dried over magnesium sulfate, filtered and evaporated to dryness under reduced pressure. The residue was purified by chromatography on silica gel (cyclohexane/EA, 50:50, then 40:60, then 35:65) to give 0.99 g of the title compound as a yellow oil.

Step 2: 4-[6-(3-Fluoro-2-methyl-benzyl)-3-formyl-5-phenyl-pyrrolo[1,2-b]pyridazin-7-carbonyl]-piperazine-1-carboxylic acid tert-butyl ester To a solution of the compound of step 1 (0.990 g, 1.61 mmol) in 11 ml of anhydrous THF, cooled to 0° C. under an atmosphere of nitrogen, was added a 1 M solution of lithium tri-tert-butoxy-aluminium hydride in THF. The mixture was stirred at 0-5° C. for 3.5 h. Then a 0.5 M aqueous solution of potassium hydrogensulfate (20 ml) was added, the mixture was vigorously stirred for 1 min and then extracted twice with EA (30 ml). The combined organic phases were washed with a saturated solution of sodium hydrogencarbonate (20 ml) and brine (40 ml), dried over magnesium sulfate and evaporated to dryness. The residue was purified by chromatography on silica gel (cyclohexane/EA, 70:30, then 65:35) to give 0.363 g of the title compound as a yellow solid melting at 208-209° C.

Step 3: 4-[6-(3-Fluoro-2-methyl-benzyl)-3-hydroxy-5-phenyl-pyrrolo[1,2-b]pyridazin-7-carbonyl]-piperazine-1-carboxylic acid tert-butyl ester To a solution of the compound of step 2 (0.395 g, 0.71 mmol) in 7.1 ml of DCM was added 77% 3-chloro-perbenzoic acid (0.239 g, 1.06 mmol) in small portions and the solution was stirred at room temperature for 2.75 h. Then DCM (15 ml) and a saturated solution of sodium hydrogencarbonate (15 ml) were added and the aqueous phase was separated and extracted with DCM (15 ml). The combined organic phases were washed with brine (30 ml), dried over magnesium sulfate, filtered and evaporated to dryness under reduced pressure. The obtained oil was dissolved in 14 ml of MOH and stirred in the presence of potassium carbonate (0.147 g, 1.06 mmol) at room temperature for 15 min. Then water was added (15 ml) and the mixture was acidified to pH 5 by dropwise addition of a 1 M aqueous solution of potassium hydrogensulfate. The solution was then extracted twice with 15 ml each of EA and the combined organic phases were washed with brine (15 ml), dried over magnesium sulfate, filtered and evaporated to dryness. The residue was purified by chromatography on silica gel (DCM/EA, 80:20, then 60:40, then 40:60) to give 0.180 g of the title compound as a yellow solid melting at 165° C.

Step 4: [6-(3-Fluoro-2-methyl-benzyl)-3-hydroxy-5-phenyl-pyrrolo[1,2-b]pyridazin-7-yl]-piperazin-1-yl-methanone The compound of step 3 (0.109 g, 0.20 mmol) was dissolved in 3 ml of anhydrous DCM and a 4 M solution of hydrogen chloride in dioxane (1.0 ml, 4.0 mmol) was added. After stirring at room temperature overnight, the mixture was evaporated to dryness under reduced pressure. The obtained solid was triturated several times with diethyl ether and dried in vacuo at 55° C. to give 0.073 g of the title compound in the form of [6-(3-fluoro-2-methyl-benzyl)-3-hydroxy-5-phenyl-pyrrolo[1,2-b]pyridazin-7-yl]-piperazin-1-yl-methanone hydrochloride as a greenish-yellow solid with the following characteristics:

Mp: 206-208° C.
LC/MS (method LC1): m/z=445 [MH$^+$]; Rt=0.96 min
$^1$H-NMR: δ (ppm)=2.00 (s, 3H), 2.91 (m, 4H), 3.46 (m, 4H), 4.08 (s, 2H), 6.77 (d, 1H), 6.96 (m, 1H), 7.05 (dd, 1H), 7.10 (s, 1H), 7.34 (m, 2H), 7.46 (m, 2H), 8.15 (s, 1H), 9.11 (br s, 2H), 10.42 (br s, 1H)

Example 11

[2-(3-Fluoro-2-methyl-benzyl)-3-phenyl-indolizin-1-yl]-piperazin-1-yl-methanone

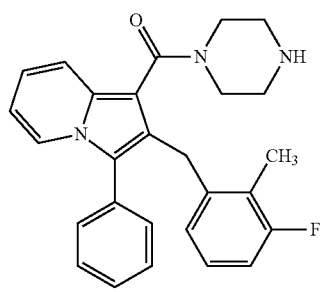 [SMILES: Cc1c(F)cccc1Cc1c(C(=O)N2CCNCC2)c2ccccn2c1-c1ccccc1]

Step 1: 1-Bromo-3-(3-fluoro-2-methyl-phenyl)-propan-2-one

Analogously to the procedure described in H. Y. Choi et al., Org. Lett. 5 (2003), 411, a solution of bromine (8.46 g, 52.95 mmol) in acetic acid (12 ml) was added at 0° C. to a solution of 1-(3-fluoro-2-methyl-phenyl)-propan-2-one (4.00 g, 24.07 mmol) in acetic acid (4 ml) and a 33% solution of hydrogen bromide in acetic acid (4 ml). The mixture was warmed to room temperature and stirred for 12 h. Then acetone was added and the mixture was stirred for 24 h. After evaporation under reduced pressure, the residue was extracted several times with DCM. The combined extracts were dried over sodium sulfate and evaporated to dryness. The residue was purified by preparative HPLC to give 4.10 g of the title compound as an oil.

LC/MS (method LC3): m/z=245 [M$^+$]

Step 2: 2-(3-Fluoro-2-methyl-benzyl)indolizine-1-carboxylic acid methyl ester The compound of step 1 (3.89 g, 15.88 mmol), pyridin-2-ylacetic acid methyl ester (1.65 g, 10.92 mmol) and sodium hydrogencarbonate (4.59 g, 54.60 mmol) in butan-2-one (43 ml) were heated under reflux for 24 h. The solid was removed by filtration and the filtrate was concentrated. The residue was purified by silica gel chromatography (HEP/EA) to give 1.99 g of the title compound.

LC/MS (method LC4): m/z=298 [MH$^+$]

Step 3: 2-(3-Fluoro-2-methyl-benzyl)-3-phenyl-indolizine-1-carboxylic acid methyl ester The compound of step 2 (1.79 g, 6.02 mmol), iodo-benzene (1.47 g, 7.22 mmol), potassium acetate (1.18 g, 12.03 mmol) and bis(triphenylphosphine)palladium(II) chloride (844 mg, 1.20 mmol) in NMP were heated at 100° C. for 10 min under argon. Then water (844 mg, 36.10 mmol) was added and heating continued for 12 h. The mixture was cooled to room temperature, diluted with DCM and washed with water. The organic phase was dried over sodium sulfate, and evaporated. The residue was purified by silica gel chromatography (HEP/EA) to give 729 mg of the title compound.

LC/MS (method LC4): m/z=374 [MH$^+$]

Step 4: 2-(3-Fluoro-2-methyl-benzyl)-3-phenyl-indolizine-1-carboxylic acid

The compound of step 3 (250 mg, 0.67 mmol) was dissolved in dioxane (10 ml) and treated with 10 ml of an aqueous 10 N solution of sodium hydroxide. The mixture was heated to 90° C. for 12 h, cooled to room temperature and neutralized with dilute hydrochloric acid. The aqueous phase was extracted with DCM and the combined organic phases dried over sodium sulfate and filtered. The solution was evaporated to give 258 mg of the crude title compound which was used in the next step without purification.

LC/MS (method LC4): m/z=360 [MH$^+$]

Step 5: 4-[2-(3-Fluoro-2-methyl-benzyl)-3-phenyl-indolizine-1-carbonyl]-piperazine-1-carboxylic acid tert-butyl ester To a solution of the crude compound obtained in step 4 (125 mg, 0.35 mmol), 1-tert-butoxycarbonyl-piperazine (67.9 mg, 0.37 mmol), N-ethyl-N'-(3-dimethylaminopropyl)carbodiimide hydrochloride (73.4 mg, 0.38 mmol) and 1-hydroxybenzotriazole (61.3 mg, 0.40 mmol) in DMF (2 ml) was added N-methyl-morpholine (0.115 ml, 1.04 mmol). The mixture was stirred at room temperature overnight, then quenched with water and extracted with EA. The organic layer was separated, dried over sodium sulfate, filtered and evaporated. The residue was purified by silica gel chromatography (HEP/EA) to give 158 mg of the title compound.

LC/MS (method LC4): m/z=528 [MH$^+$]

Step 6: [2-(3-Fluoro-2-methyl-benzyl)-3-phenyl-indolizin-1-yl]-piperazin-1-yl-methanone A solution of the compound of step 5 (158 mg, 299 mmol) in DCM (8 ml) and TFA (4 ml) was stirred at room temperature for 2 h. The solvents were evaporated and the residue was purified by preparative HPLC. The fractions containing the title compound were combined and lyophilized overnight. The obtained solid was dissolved in a small quantity of MOH, mixed with 0.1 N hydrochloric acid and the mixture lyophilized overnight to give 108 mg of the title compound in the form of [2-(3-fluoro-2-methyl-benzyl)-3-phenyl-indolizin-1-yl]-piperazin-1-yl-methanone hydrochloride with the following characteristics:

LC/MS (method LC4): m/z=428.20 [MH$^+$]; Rt=0.82 min
$^1$H-NMR (500 MHz, DMSO-D$_6$): δ (ppm)=1.93 (s, 3H), 2.56 (m, 6H), 3.10 (m, 2H), 3.47 (m, 2H), 3.59 (m, 2H), 4.01 (m, 2H), 6.71 (m, 2H), 6.92 (m, 1H), 7.01 (m, 2H), 7.47 (m, 4H), 7.58 (m, 2H), 8.06 (m, 1H), 9.05 (m, 1H), 9.28 (m, 1H)

Example 12

[7-Bromo-2-(3-fluoro-2-methyl-benzyl)-3-phenyl-indolizin-1-yl]-piperazin-1-yl-methanone

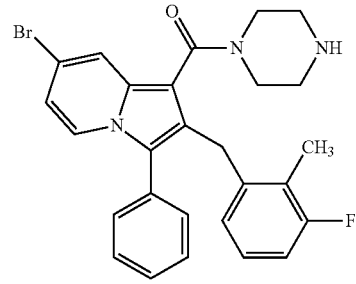 [SMILES: Cc1c(F)cccc1Cc1c(C(=O)N2CCNCC2)c2cc(Br)ccn2c1-c1ccccc1]

Step 1: 7-Bromo-2-(3-fluoro-2-methyl-benzyl)-3-phenyl-indolizine-1-carboxylic acid methyl ester The compound of example 11, step 3, (550 mg, 1.47 mmol) was dissolved in a mixture of benzene (15 ml) and chloroform (15 ml) and treated at room temperature with bromine (235 mg, 1.47 mmol) under stirring. After 2 h, DBU (224 mg, 1.47 mmol) was added and the mixture stirred for 18 h at room temperature. The solvent was removed in vacuo and the remaining residue was purified by silica gel chromatography (HEP/EA). 460 mg of the title compound were obtained.

LC/MS (method LC4): m/z=452 [M$^+$]

Step 2: 7-Bromo-2-(3-fluoro-2-methyl-benzyl)-3-phenyl-indolizine-1-carboxylic acid The compound of step 1 (450 mg, 0.99 mmol) was dissolved in 1,4-dioxane (10 ml) and treated with 10 ml of an aqueous 10 N solution of sodium hydroxide. The mixture was heated to 90° C. for 12 h, cooled to room temperature and neutralized with dilute hydrochloric acid. The aqueous phase was extracted with DCM, and the combined organic phase were dried over sodium sulfate. The crude title product obtained after evaporation was used without purification in the next step.

LC/MS (method LC4): m/z=439 [MH$^+$]

Step 3: 4-[7-Bromo-2-(3-fluoro-2-methyl-benzyl)-3-phenyl-indolizine-1-carbonyl]-piperazine-1-carboxylic acid tert-butyl ester To a solution of the crude compound obtained in step 2 (219 mg, 0.50 mmol), 1-tert-butoxycarbonyl-piperazine (98 mg, 0.55 mmol), N-ethyl-N'-(3-dimethylaminopropyl)carbodiimide hydrochloride (105 mg, 0.55 mmol) and 1-hydroxybenzotriazole (88 mg, 0.58 mmol) in DMF (5 ml) was added N-methyl-morpholine (330 µl, 3.00 mmol), and the mixture was stirred at room temperature overnight. The mixture was quenched with water and extracted with EA. The organic layer was separated, dried over sodium sulfate, filtered and evaporated. The residue was purified by silica gel chromatography (HEP/EA). 300 mg of the title compound were obtained.

LC/MS (method LC4): m/z=607 [MH$^+$]

Step 4: [7-Bromo-2-(3-fluoro-2-methyl-benzyl)-3-phenyl-indolizin-1-yl]-piperazin-1-yl-methanone A solution of the compound of step 3 (70 mg, 115 µmol) in DCM (4 ml) and TFA (2 ml) was stirred at room temperature for 2 h. The solvents were evaporated and the resulting solid was purified by preparative HPLC. The fractions containing the title compound were combined and lyophilized overnight. The obtained solid was dissolved in a small quantity of MOH, mixed with 0.1 N hydrochloric acid and the mixture lyophilized overnight to give 15 mg of the title compound in the form of [7-bromo-2-(3-fluoro-2-methyl-benzyl)-3-phenyl-indolizin-1-yl]-piperazin-1-yl-methanone hydrochloride with the following characteristics:

LC/MS (method LC4): m/z=508.2 [MH$^+$]; Rt=0.85 min
$^1$H-NMR (500 MHz, DMSO-D$_6$): δ (ppm)=1.92 (s, 3H), 3.13 (m, 2H), 3.58 (m, 2H), 4.01 (m, 2H), 6.71 (m, 1H), 6.79 (m, 1H), 6.93 (m, 1H), 7.01 (m, 1H), 7.46 (m, 3H), 7.58 (m, 2H), 7.74 (m, 1H), 7.97 (m, 1H), 9.01 (m, 2H)

Analogously to the example compounds described above, the compounds of examples 13 to 46 were prepared.

Example 13

2-(3-Fluoro-2-methyl-benzyl)-1-phenyl-3-(piperazine-1-carbonyl)-indolizine-6-carboxylic acid methylamide

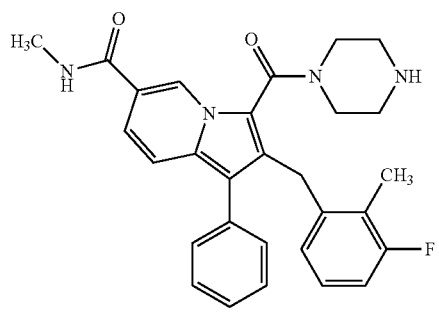 [SMILES: CNC(=O)c1ccc2c(-c3ccccc3)c(Cc3cccc(F)c3C)c(C(=O)N3CCNCC3)n2c1]

The title compound was obtained in the form of 2-(3-fluoro-2-methyl-benzyl)-1-phenyl-3-(piperazine-1-carbonyl)-indolizine-6-carboxylic acid methylamide hydrochloride.
Mp: 273° C.
LC/MS (method LC1): m/z=485; Rt=0.99 min

Example 14

(2-Benzyl-3-phenyl-indolizin-1-yl)-piperazin-1-yl-methanone

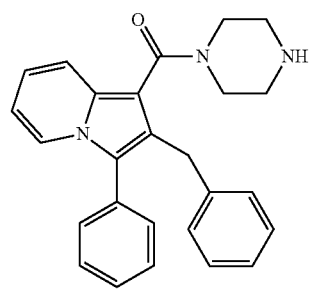 [SMILES: O=C(c1c(Cc2ccccc2)c(-c2ccccc2)n2ccccc12)N1CCNCC1]

The title compound was obtained in the form of (2-benzyl-3-phenyl-indolizin-1-yl)-piperazin-1-yl-methanone hydrochloride.
LC/MS (method LC3): m/z=396.20; Rt=1.09 min

Example 15

[2-(3-Fluoro-2-methyl-benzyl)-3-phenyl-indolizin-1-yl)-((S)-3-methyl-piperazin-1-yl)-methanone

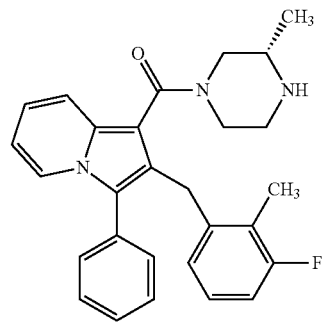 [SMILES: Cc1c(F)cccc1Cc1c(C(=O)N2CCN[C@@H](C)C2)c2ccccn2c1-c1ccccc1]

The title compound was obtained in the form of [2-(3-fluoro-2-methyl-benzyl)-3-phenyl-indolizin-1-yl)-((S)-3-methyl-piperazin-1-yl)-methanone hydrochloride.
LC/MS (method LC4): m/z=442.20; Rt=0.83 min

Example 16

[7-Bromo-2-(3-fluoro-2-methyl-benzyl)-3-phenyl-indolizin-1-yl)-((S)-3-methyl-piperazin-1-yl)-methanone

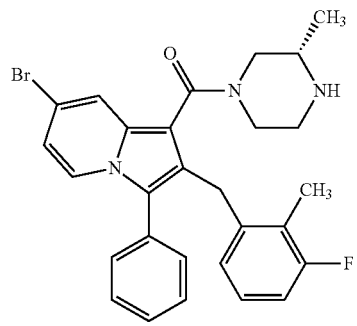 [SMILES: Cc1c(F)cccc1Cc1c(C(=O)N2CCN[C@@H](C)C2)c2cc(Br)ccn2c1-c1ccccc1]

The title compound was obtained in the form of [7-bromo-2-(3-fluoro-2-methyl-benzyl)-3-phenyl-indolizin-1-yl]-((S)-3-methyl-piperazin-1-yl)-methanone hydrochloride.
LC/MS (method LC4): m/z=521; Rt=0.88 min Example 17

[2-(2,6-Dimethyl-benzyl)-1-phenyl-indolizin-3-yl)-((R)-3-methyl-piperazin-1-yl)-methanone

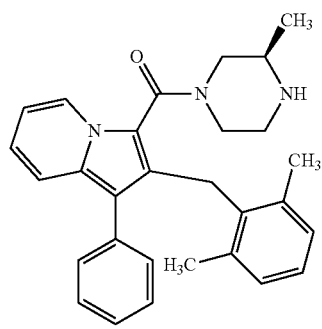 [SMILES: Cc1cccc(C)c1Cc1c(-c2ccccc2)c2ccccn2c1C(=O)N1CCN[C@H](C)C1]

The title compound was obtained in the form of [2-(2,6-dimethyl-benzyl)-1-phenyl-indolizin-3-yl)-((R)-3-methyl-piperazin-1-yl)-methanone hydrochloride.
Mp: 302° C.
LC/MS (method LC1): m/z=438; Rt=4.01 min The compounds of examples 18 to 21 listed in Table 1 are compounds of the formula Iv. They were obtained in the form of the hydrochloride. They can be named as [1-(optionally substituted phenyl)-2-(substituted benzyl)-indolizin-3-yl]-piperazin-1-yl-methanone, allowing for modifications due to the rules of nomenclature, for example as [2-(3-fluoro-2-methyl-benzyl)-1-(3-fluoro-phenyl)-indolizin-3-yl]-piperazin-1-yl-methanone in the case of example 20.

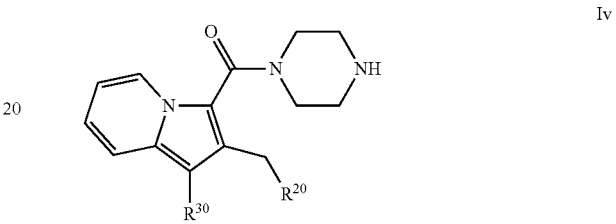

TABLE 1

Example compounds of the formula Iv

| Example no. | R²⁰ | R³⁰ | Rt [min] | MS (m/z) | LC/MS | Mp [° C.] |
|---|---|---|---|---|---|---|
| 18 | 5-fluoro-2-methyl-phenyl | phenyl | 1.08 | 428 | LC1 | 271 |
| 19 | 2,5-difluoro-phenyl | phenyl | 1.05 | 432 | LC1 | 295 |
| 20 | 3-fluoro-2-methyl-phenyl | 3-fluoro-phenyl | 5.50 | 446 | LC2 | 355 |
| 21 | 2,6-dimethyl-phenyl | phenyl | 3.90 | 424 | LC2 | 355-356 |

The compounds of examples 22 to 46 listed in Table 2 are compounds of the formula Iw. They were obtained in the form of the hydrochloride or, in the case of examples 32, 33 and 37, in the form of the dihydrochloride. They can be named as [2-(3-fluoro-2-methyl-benzyl)-(optionally 7-R⁴⁰-substituted)-1-phenyl-indolizin-3-yl]-R⁹⁰-methanone in case the group Y is CH, or as [6-(3-fluoro-2-methyl-benzyl)-(optionally 3-R⁴⁰-substituted)-5-phenyl-pyrrolo[1,2-b]pyridazin-7-yl]-R⁹⁰-methanone in case the group Y is N, allowing for modifications due to the rules of nomenclature, for example as [2-(3-fluoro-2-methyl-benzyl)-7-methoxy-1-phenyl-indolizin-3-yl]-piperazin-1-yl-methanone in the case of example 35, or as 6-(3-fluoro-2-methyl-benzyl)-7-{(S)-3-[(2-methoxy-ethylcarbamoyl)-methyl]-piperazine-1-carbonyl}-5-phenyl-pyrrolo[1,2-b]pyridazine-3-carboxylic acid ethylamide in the case of example 42.

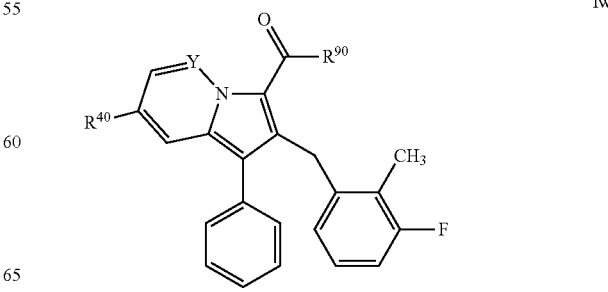

TABLE 2

Example compounds of the formula Iw

| Example no. | Y | R⁴⁰ | R⁹⁰ | Rt [min] | MS (m/z) | LC/MS | Mp [° C.] | α (1) |
|---|---|---|---|---|---|---|---|---|
| 22 | CH | hydrogen | (R)-3-hydroxymethyl-piperazin-1-yl | 3.62 | 458 | LC2 | 180-181 | |
| 23 | CH | hydrogen | (R)-3-methyl-piperazin-1-yl | 3.90 | 424 | LC2 | 174 | |
| 24 | CH | hydrogen | (S)-3-(butylcarbamoyl-methyl)-piperazin-1-yl | 1.19 | 541 | LC1 | 137 | |
| 25 | CH | hydrogen | (S)-3-(ethylcarbamoyl-methyl)-piperazin-1-yl | 1.09 | 513 | LC1 | 135 | |
| 26 | CH | hydrogen | (S)-3-(2-methylcarbamoyl-ethyl)-piperazin-1-yl | 1.09 | 513 | LC1 | 127-129 | |
| 27 | CH | hydrogen | (S)-3-[(3-methoxypropylcarbamoyl)-methyl]-piperazin-1-yl | 1.10 | 557 | LC1 | 103 | |
| 28 | CH | hydrogen | (S)-3-[(2-carboxyethylcarbamoyl)-methyl]-piperazin-1-yl | 1.04 | 557 | LC1 | 173-175 | +1.599 ° c = 0.319 |
| 29 | CH | hydrogen | (S)-3-[(2-dimethylcarbamoyl-ethylcarbamoyl)-methyl]-piperazin-1-yl | 1.07 | 584 | LC1 | 139-141 | −3.604 ° c = 0.283 |
| 30 | CH | hydrogen | (S)-3-[(2-methoxycarbonyl-ethylcarbamoyl)-methyl]-piperazin-1-yl | 1.10 | 571 | LC1 | 112-113 | +4.277 ° c = 0.325 |
| 31 | CH | hydrogen | (S)-3-[(2-methanesulfonyl-ethylcarbamoyl)-methyl]-piperazin-1-yl | 1.05 | 591 | LC1 | 166-168 | −3.538 ° c = 0.195 |
| 32 | CH | hydrogen | (S)-3-{[(pyridin-3-ylmethyl)-carbamoyl]-methyl}-piperazin-1-yl | 0.95 | 576 | LC1 | 181-182 | −2.414 ° c = 0.232 |
| 33 | CH | hydrogen | (S)-3-[(2-morpholin-4-yl-ethylcarbamoyl)-methyl]-piperazin-1-yl | 0.97 | 598 | LC1 | 125-127 | −5.021 ° c = 0.233 |
| 34 | CH | hydrogen | (S)-3-[(2-hydroxyethylcarbamoyl)-methyl]-piperazin-1-yl | 1.03 | 529 | LC1 | 118-120 | −2.015 ° c = 0.670 |
| 35 | CH | methoxy | piperazin-1-yl | 1.09 | 458 | LC1 | 124-125 | |
| 36 | N | methoxy | piperazin-1-yl | 1.04 | 459 | LC1 | 139-141 | |
| 37 | CH | hydrogen | (S)-3-{[(pyridin-2-ylmethyl)-carbamoyl]-methyl}-piperazin-1-yl | 1.00 | 576 | LC1 | 131-133 | −6.266 ° c = 0.316 |
| 38 | N | dimethylcarbamoyl | (S)-3-[(2-methoxyethylcarbamoyl)-methyl]-piperazin-1-yl | 0.98 | 615 | LC1 | 147-149 | −1.325 ° c = 0.702 |
| 39 | N | piperidin-1-ylcarbonyl | (S)-3-[(2-hydroxyethylcarbamoyl)-methyl]-piperazin-1-yl | 1.04 | 641 | LC1 | 164-166 | −2.834 ° c = 0.674 |
| 40 | CH | dimethylcarbamoyl | (S)-3-(ethylcarbamoylmethyl)-piperazin-1-yl | 1.00 | 584 | LC1 | 169-170 | +3.279 ° c = 1.046 |
| 41 | CH | dimethylcarbamoyl | (S)-3-[(2-methoxyethylcarbamoyl)-methyl]-piperazin-1-yl | 0.99 | 614 | LC1 | 148-149 | +.058 ° c = 0.702 |
| 42 | N | ethylcarbamoyl | (S)-3-[(2-methoxyethylcarbamoyl)-methyl]-piperazin-1-yl | 1.08 | 615 | LC1 | 151-153 | +11.15 ° c = 0.234 |
| 43 | N | piperidin-1-ylcarbonyl | (S)-3-[(2-methoxyethylcarbamoyl)-methyl]-piperazin-1-yl | 1.08 | 655 | LC1 | 169-171 | −2.011 ° c = 0.378 |
| 44 | N | diethylcarbamoyl | (S)-3-(ethylcarbamoylmethyl)-piperazin-1-yl | 1.08 | 613 | LC1 | 145-147 | +3.13 ° c = 1 |
| 45 | N | dimethylcarbamoyl | (S)-3-(ethylcarbamoylmethyl)-piperazin-1-yl | 0.99 | 585 | LC1 | 180-182 | +4.221 ° c = 0.77 |
| 46 | N | dimethylcarbamoyl | (S)-3-{[(2-methoxyethyl)-methylcarbamoyl]-methyl}-piperazin-1-yl | 1.01 | 629 | LC1 | 130-132 | +5.81 ° c = 0.494 |

(1) optical rotation (in °) at the concentration c (in g/100 ml) in MOH

Further compounds of the formula Iw, which can be prepared analogously to the example compounds described above, are listed in Table 3. They can be named as indicated above for the compounds listed in Table 2.

TABLE 3

Compounds of the formula Iw

| Example no. | Y | R⁴⁰ | R⁹⁰ |
|---|---|---|---|
| 47 | CH | methoxy | (S)-3-[(2-hydroxy-ethylcarbamoyl)-methyl]-piperazin-1-yl |
| 48 | CH | hydroxy | (S)-3-(butylcarbamoylmethyl)-piperazin-1-yl |
| 49 | CH | hydrogen | (S)-2-benzyl-piperazin-1-yl |
| 50 | CH | hydrogen | 2,2-dimethyl-piperazin-1-yl |
| 51 | CH | pyrrolidin-1-yl | (S)-3-[(2-cyano-ethylcarbamoyl)-methyl]-piperazin-1-yl |
| 52 | N | morpholin-4-yl | (S)-3-[(2-cyano-ethylcarbamoyl)-methyl]-piperazin-1-yl |
| 53 | CH | dimethyl-carbamoyl | (S)-3-[(2-cyano-ethylcarbamoyl)-methyl]-piperazin-1-yl |
| 54 | N | methylcarbamoyl | (S)-3-{[(2-methoxy-ethyl)-methyl-carbamoyl]-methyl}-piperazin-1-yl |

Pharmacological Tests
A) Inhibition of Renin

The renin-inhibiting activity of compounds of the invention was demonstrated in an in vitro test in which a non-endogenous fluorogenic peptide substrate is cleaved by renin specifically at the Leu-Val bond which corresponds to the cleavage site of angiotensinogen.

Recombinant human renin (Cayman, no. 10006217) at a concentration of 5 nM was incubated with the test compounds at various concentrations and the synthetic substrate Dabcyl-γ-Abu-Ile-His-Pro-Phe-His-Leu-Val-Ile-His-Thr-EDANS (Bachem, no. M-2050; Dabcyl means the 4-(4-dimethylamino-phenylazo)-benzoyl group and EDANS means the amide with 5-[(2-aminoethyl)amino]-naphthalene-1-sulfonic acid) at a concentration of 10 μM for 2 h at room temperature in 0.05 M Tris buffer (pH 8) containing 0.1 M NaCl, 2.5 mM EDTA and 1.25 mg/ml bovine serum albumin. The increase in fluorescence, which is due to fluorescence resonance energy transfer, was recorded at an excitation wavelength of 330 nm and an emission wavelength of 485 nm in a microplate spectrofluorometer. Inhibitory concentrations $IC_{50}$ were calculated from the percentage of inhibition of renin activity as a function of the concentration of the test compound. In this test, the example compounds generally inhibited renin with an $IC_{50}$ value of less than about 10 micromol/l (10 μM). Representative $IC_{50}$ values, which were determined with the compounds in the form of the obtained salt indicated in the examples above, are listed in Table 4.

TABLE 4

$IC_{50}$ values for inhibition of renin (fluorogenic peptide substrate)

| Compound of example no. | $IC_{50}$ (μM) |
|---|---|
| 1 | 0.0071 |
| 2 | 0.038 |
| 6 | 0.0026 |
| 7 | 0.0026 |
| 9 | 0.0043 |
| 10 | 0.0082 |
| 11 | 0.023 |
| 12 | 0.36 |
| 13 | 0.064 |
| 15 | 0.076 |
| 17 | 0.87 |
| 20 | 0.0034 |
| 22 | 0.10 |
| 26 | 0.23 |
| 30 | 0.031 |
| 31 | 0.021 |
| 32 | 0.038 |
| 35 | 0.028 |
| 39 | 0.0074 |
| 46 | 0.010 |

B) Inhibition of Renin in Human Plasma

The renin-inhibiting activity of compounds of the invention was also demonstrated in an in vitro test in the presence of human plasma. The procedure followed the procedure described in pharmacological test A except that human recombinant renin at a concentration of 30 nM was incubated with the test compounds at various concentrations and the fluorogenic substrate Dabcyl-γ-Abu-Ile-His-Pro-Phe-His-Leu-Val-Ile-His-Thr-EDANS at a concentration of 25 μM for 30 min at 37° C. and 30 min at room temperature in human plasma (Innovative Research, pooled normal human plasma collected on EDTA K3 as an anticoagulant, no. IPLA-5).

C) Antihypertensive Activity

The in vivo antihypertensive activity of compounds of the invention can be demonstrated in doubly transgenic mice overexpressing both human renin and angiotensinogen genes (dTghRenhAgt mice; cf. D. C. Merrill et al., J. Clin. Invest. 97 (1996), 1047; R. L. Davisson et al., J. Clin. Invest. 99 (1997), 1258; J. L. Lavoie et al., Acta Physiol. Scand. 81 (2004), 571; available by breeding strains carrying the human renin transgene and the human angiotensinogen transgene, respectively). Briefly, in this test the arterial pressure in freely moving male dTghRenhAgT mice is determined by telemetry monitoring. For this purpose, the catheter of a radio transmitter (model TA11PA-10, DSI) is implanted into the left carotid artery of dTghRenhAgT mice under anesthesia. Animals are kept on a 12 h light/dark cycle and have free access to food and water. After one week of recovery period, arterial pressure and heart rate are monitored over 24 h to establish the baseline values. Then animals receive orally by gavage either the daily dose of the test compound in vehicle (water containing 0.6% of methylcellulose and 0.5% of Tween® 80) or, as a control, vehicle only. Hemodynamic parameters are recorded continuously for an additional 24 h and maximal mean arterial pressure lowering effect and duration of antihypertensive activity are determined (mean arterial pressure=diastolic pressure+⅓·(systolic pressure−diastolic pressure)). Compounds are screened at various doses such as 3 mg/kg body weight and 10 mg/kg body weight per day.

What is claimed is:

1. A compound of formula Ia or Ib, in any of its stereoisomeric forms or a mixture of stereoisomeric forms in any ratio, or a physiologically acceptable salt thereof,

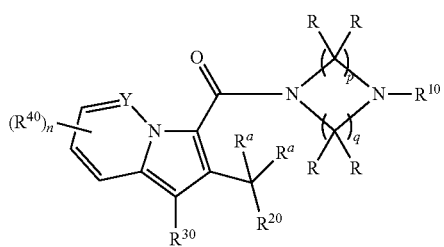

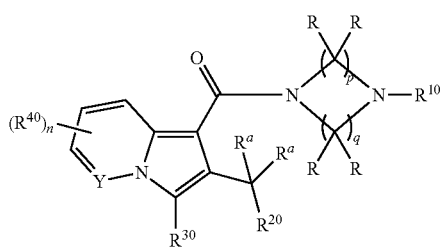

wherein $R^a$ is chosen from hydrogen, fluorine and $(C_1\text{-}C_4)$-alkyl, wherein the two groups $R^a$ are independent of each other and can be identical or different, or the two groups $R^a$ together are a divalent $(C_2\text{-}C_5)$-alkyl group;

R is chosen from hydrogen, $(C_1\text{-}C_6)$-alkyl which is optionally substituted by one or more identical or different substituents $R^1$, and $(C_3\text{-}C_7)$-cycloalkyl, wherein all groups R are independent of each other and can be identical or different, or two groups R bonded to the same carbon atom together are a divalent $(C_2\text{-}C_5)$-alkyl group;

$R^1$ is chosen from $(C_3\text{-}C_7)$-cycloalkyl, phenyl, heteroaryl, $Het^1$, hydroxy, $(C_1\text{-}C_4)$-alkyl-O—, $(C_1\text{-}C_4)$-alkyl-$S(O)_m$—, $R^2$—$N(R^3)$—C(O)—, $R^4$—O—C(O)— and cyano;

$R^2$ is chosen from hydrogen, $(C_1\text{-}C_6)$-alkyl which is optionally substituted by one or more identical or different substituents $R^5$, and $(C_3\text{-}C_7)$-cycloalkyl, wherein all groups $R^2$ are independent of each other and can be identical or different;

$R^3$, $R^4$, $R^6$, $R^7$ and $R^8$ are chosen from hydrogen and $(C_1\text{-}C_4)$-alkyl, wherein all groups $R^3$, $R^4$, $R^6$, $R^7$ and $R^8$ are independent of each other and can be identical or different;

$R^5$ is chosen from hydroxy, $(C_1\text{-}C_4)$-alkyl-O—, $(C_1\text{-}C_4)$-alkyl-$S(O)_m$—, $R^6$—$N(R^7)$—C(O)—, $R^8$—O—C(O)—, cyano, $(C_3\text{-}C_7)$-cycloalkyl, phenyl, heteroaryl and $Het^1$;

$R^{10}$ is chosen from hydrogen, $(C_1\text{-}C_6)$-alkyl-O—C(O)— and $(C_3\text{-}C_7)$-cycloalkyl-$C_vH_{2v}$—O—C(O)—;

$R^{20}$ is chosen from phenyl and heteroaryl which are optionally substituted by one or more identical or different substituents chosen from halogen, $(C_1\text{-}C_4)$-alkyl, $(C_1\text{-}C_4)$-alkyl-O—, $(C_1\text{-}C_4)$-alkyl-$S(O)_m$— and cyano;

$R^{30}$ is chosen from $(C_5\text{-}C_7)$-cycloalkyl, $(C_5\text{-}C_7)$-cycloalkenyl, tetrahydropyranyl, phenyl and heteroaryl, wherein cycloalkyl and cycloalkenyl are optionally substituted by one or more identical or different substituents chosen from fluorine, $(C_1\text{-}C_4)$-alkyl and hydroxy, and phenyl and heteroaryl are optionally substituted by one or more identical or different substituents chosen from halogen, $(C_1\text{-}C_4)$-alkyl, $(C_1\text{-}C_4)$-alkyl-O— and cyano;

$R^{40}$ is chosen from halogen, $(C_1\text{-}C_4)$-alkyl, $(C_3\text{-}C_7)$-cycloalkyl-$C_vH_{2v}$—, hydroxy, $(C_1\text{-}C_4)$-alkyl-O—, $(C_1\text{-}C_4)$-alkyl-$S(O)_m$—, $R^{41}$—$N(R^{42})$—, $Het^2$, $R^{41}$—$N(R^{42})$—C(O)—, $Het^2$-C(O)—, cyano, $R^{41}$—$N(R^{42})$—$S(O)_2$— and $Het^2$-$S(O)_2$—, wherein all substituents $R^{40}$ are independent of each other and can be identical or different;

$R^{41}$ is chosen from hydrogen, $(C_1\text{-}C_4)$-alkyl and $(C_3\text{-}C_7)$-cycloalkyl-$C_vH_{2v}$—, wherein all groups $R^{41}$ are independent of each other and can be identical or different;

$R^{42}$ is chosen from hydrogen and $(C_1\text{-}C_4)$-alkyl, wherein all groups $R^{42}$ are independent of each other and can be identical or different;

Y is chosen from N, CH and $C((C_1\text{-}C_4)\text{-alkyl})$;

heteroaryl is an aromatic monocyclic, 5-membered or 6-membered, heterocyclic group which comprises 1, 2 or 3 identical or different ring heteroatoms chosen from N, O and S, wherein one of the ring nitrogen atoms can carry a hydrogen atom or a $(C_1\text{-}C_4)$-alkyl substituent, and wherein the heteroaryl group is bonded via a ring carbon atom;

$Het^1$ is a saturated, monocyclic, 4-membered to 7-membered heterocyclic group which comprises 1 or 2 identical or different ring heteroatoms chosen from N, O and S, wherein the group $Het^1$ is bonded via a ring carbon atom or a ring nitrogen atom, wherein ring nitrogen atoms can carry a hydrogen atom or a substituent chosen from $(C_1\text{-}C_4)$-alkyl, $(C_1\text{-}C_6)$-alkyl-O—C(O)— and $(C_3\text{-}C_7)$-cycloalkyl-$C_vH_{2v}$—O—C(O)—, wherein ring sulfur atoms can carry one or two oxo groups, and wherein $Het^1$ is optionally substituted on ring carbon atoms by one or more identical or different substituents chosen from fluorine, $(C_1\text{-}C_4)$-alkyl and oxo;

$Het^2$ is a saturated, monocyclic, 4-membered to 7-membered heterocyclic group which comprises a ring nitrogen atom via which the group $Het^2$ is bonded and optionally an additional ring heteroatom chosen from N, O and S, wherein the additional ring nitrogen atom carries a hydrogen atom or a substituent chosen from $(C_1\text{-}C_4)$-alkyl, $(C_1\text{-}C_6)$-alkyl-O—C(O)— and $(C_3\text{-}C_7)$-cycloalkyl-$C_vH_{2v}$—O—C(O)—, wherein the ring sulfur atom can carry one or two oxo groups, and wherein $Het^2$ is optionally substituted on ring carbon atoms by one or more identical or different substituents chosen from fluorine, $(C_1\text{-}C_4)$-alkyl and oxo;

m is chosen from 0, 1 and 2, wherein all numbers m are independent of each other and can be identical or different;

n is chosen from 0, 1, 2 and 3;

p and q, which are independent of each other and can be identical or different, are chosen from 2 and 3;

v is chosen from 0, 1 and 2, wherein all numbers v are independent of each other and can be identical or different;

wherein all alkyl groups, independently of each other, are optionally substituted by one or more fluorine atoms;

wherein all cycloalkyl groups, independently of each other, are optionally substituted by one or more identical or different substituents chosen from fluorine and $(C_1\text{-}C_4)$-alkyl, unless specified otherwise;

wherein all phenyl and heteroaryl groups present in $R^1$ and $R^5$, independently of each other, are optionally substituted by one or more identical or different substituents chosen from halogen, $(C_1\text{-}C_4)$-alkyl, $(C_1\text{-}C_4)$-alkyl-O—, $(C_1\text{-}C_4)$-alkyl-$S(O)_2$— and cyano.

2. A compound of the formula Ia or Ib as claimed in claim 1, in any of its stereoisomeric forms or a mixture of stereoisomeric forms in any ratio, or a physiologically acceptable salt thereof, wherein p and q are 2.

3. A compound of the formula Ia or Ib as claimed in claim 1, in any of its stereoisomeric forms or a mixture of stereoisomeric forms in any ratio, or a physiologically acceptable salt thereof, wherein $R^{20}$ is phenyl which is optionally substituted by one or more identical or different substituents chosen from halogen, $(C_1-C_4)$-alkyl, $(C_1-C_4)$-alkyl-O—, $(C_1-C_4)$-alkyl-S(O)$_m$— and cyano.

4. A compound of the formula Ia or Ib as claimed in claim 1, in any of its stereoisomeric forms or a mixture of stereoisomeric forms in any ratio, or a physiologically acceptable salt thereof, wherein $R^{30}$ is phenyl which is optionally substituted by one or more identical or different substituents chosen from halogen, $(C_1-C_4)$-alkyl, $(C_1-C_4)$-alkyl-O— and cyano.

5. A compound of the formula Ia or Ib as claimed in claim 1, in any of its stereoisomeric forms or a mixture of stereoisomeric forms in any ratio, or a physiologically acceptable salt thereof, wherein $R^a$ is chosen from hydrogen and fluorine;

R is chosen from hydrogen and $(C_1-C_6)$-alkyl which is optionally substituted by one or more identical or different substituents $R^1$, wherein all groups R are independent of each other and can be identical or different, or two groups R bonded to the same carbon atom together are a divalent $(C_2-C_5)$-alkyl group;

$R^1$ is chosen from phenyl, hydroxy, $(C_1-C_4)$-alkyl-O—, $R^2$—N($R^3$)—C(O)—, $R^4$—O—C(O)— and cyano;

$R^2$ is chosen from hydrogen and $(C_1-C_6)$-alkyl which is optionally substituted by one or more identical or different substituents $R^5$, wherein all groups $R^2$ are independent of each other and can be identical or different;

$R^3$, $R^4$, $R^6$, $R^7$ and $R^8$ are chosen from hydrogen and $(C_1-C_4)$-alkyl, wherein all groups $R^3$, $R^4$, $R^6$, $R^7$ and $R^8$ are independent of each other and can be identical or different;

$R^5$ is chosen from hydroxy, $(C_1-C_4)$-alkyl-O—, $(C_1-C_4)$-alkyl-S(O)$_m$—, $R^6$—N($R^7$)—C(O)—, $R^8$—O—C(O)—, cyano, $(C_3-C_7)$-cycloalkyl, phenyl, heteroaryl and Het$^1$;

$R^{10}$ is chosen from hydrogen and $(C_1-C_6)$-alkyl-O—C(O)—;

$R^{20}$ is chosen from phenyl and heteroaryl which are optionally substituted by one or more identical or different substituents chosen from halogen, $(C_1-C_4)$-alkyl, $(C_1-C_4)$-alkyl-O—, $(C_1-C_4)$-alkyl-S(O)$_m$— and cyano;

$R^{30}$ is chosen from $(C_5-C_7)$-cycloalkyl, tetrahydropyranyl, phenyl and heteroaryl, wherein cycloalkyl is optionally substituted by one or more identical or different substituents chosen from fluorine, $(C_1-C_4)$-alkyl and hydroxy, and phenyl and heteroaryl are optionally substituted by one or more identical or different substituents chosen from halogen, $(C_1-C_4)$-alkyl, $(C_1-C_4)$-alkyl-O— and cyano;

$R^{40}$ is chosen from halogen, $(C_1-C_4)$-alkyl, $(C_3-C_7)$-cycloalkyl-C$_v$H$_{2v}$—, hydroxy, $(C_1-C_4)$-alkyl-O—, $(C_1-C_4)$-alkyl-S(O)$_m$—, $R^{41}$—N($R^{42}$)—, Het$^2$, $R^{41}$—N($R^{42}$)—C(O)—, Het$^2$-C(O)—, cyano, $R^{41}$—N($R^{42}$)—S(O)$_2$— and Het$^2$-S(O)$_2$—, wherein all substituents $R^{40}$ are independent of each other and can be identical or different;

$R^{41}$ is chosen from hydrogen and $(C_1-C_4)$-alkyl, wherein all groups $R^{41}$ are independent of each other and can be identical or different;

$R^{42}$ is chosen from hydrogen and $(C_1-C_4)$-alkyl, wherein all groups $R^{42}$ are independent of each other and can be identical or different;

Y is chosen from N, CH and C(($C_1-C_4$)-alkyl);

heteroaryl is an aromatic monocyclic, 5-membered or 6-membered, heterocyclic group which comprises 1 or 2 identical or different ring heteroatoms chosen from N, O and S, wherein one of the ring nitrogen atoms can carry a hydrogen atom or a $(C_1-C_4)$-alkyl substituent, and wherein the heteroaryl group is bonded via a ring carbon atom;

Het$^1$ is a saturated, monocyclic, 4-membered to 7-membered heterocyclic group which comprises 1 or 2 identical or different ring heteroatoms chosen from N, O and S, wherein the group Het$^1$ is bonded via a ring carbon atom or a ring nitrogen atom, wherein ring nitrogen atoms can carry a hydrogen atom or a substituent chosen from $(C_1-C_4)$-alkyl and $(C_1-C_6)$-alkyl-O—C(O)—, wherein ring sulfur atoms can carry one or two oxo groups, and wherein Het$^1$ is optionally substituted on ring carbon atoms by one or more identical or different substituents chosen from fluorine, $(C_1-C_4)$-alkyl and oxo;

Het$^2$ is a saturated, monocyclic, 4-membered to 7-membered heterocyclic group which comprises a ring nitrogen atom via which the group Het$^2$ is bonded and optionally an additional ring heteroatom chosen from N, O and S, wherein the additional ring nitrogen atom carries a hydrogen atom or a substituent chosen from $(C_1-C_4)$-alkyl and $(C_1-C_6)$-alkyl-O—C(O)—, wherein the ring sulfur atom can carry one or two oxo groups, and wherein Het$^2$ is optionally substituted on ring carbon atoms by one or more identical or different substituents chosen from fluorine, $(C_1-C_4)$-alkyl and oxo;

m is chosen from 0, 1 and 2, wherein all numbers m are independent of each other and can be identical or different;

n is chosen from 0, 1 and 2;

p and q are 2;

v is chosen from 0, 1 and 2, wherein all numbers v are independent of each other and can be identical or different;

wherein all alkyl groups, independently of each other, are optionally substituted by one or more fluorine atoms;

wherein all cycloalkyl groups, independently of each other, are optionally substituted by one or more identical or different substituents chosen from fluorine and $(C_1-C_4)$-alkyl, unless specified otherwise;

wherein all phenyl and heteroaryl groups present in $R^1$ and $R^5$, independently of each other, are optionally substituted by one or more identical or different substituents chosen from halogen, $(C_1-C_4)$-alkyl, $(C_1-C_4)$-alkyl-S(O)$_2$— and cyano.

6. A compound of the formula Ia or Ib as claimed in claim 1, in any of its stereoisomeric forms or a mixture of stereoisomeric forms in any ratio, or a physiologically acceptable salt thereof, wherein one, two or three of the groups R are independently of each other chosen from hydrogen, $(C_1-C_6)$-alkyl which is optionally substituted by one, two or three identical or different substituents $R^1$, and $(C_3-C_7)$-cycloalkyl, or two of these groups R bonded to the same carbon atom together are a divalent $(C_2-C_5)$-alkyl group, and all other groups R are hydrogen.

7. A compound of the formula Ia or Ib as claimed in claim 1, in any of its stereoisomeric forms or a mixture of stereoisomeric forms in any ratio, or a physiologically acceptable salt thereof, which is a compound of the formula Ia.

8. A compound of the formula Ia or Ib as claimed in claim 1, in any of its stereoisomeric forms or a mixture of stereoisomeric forms in any ratio, or a physiologically acceptable salt thereof, which is a compound of the formula Ib.

9. A process for the preparation of a compound of the formula Ia or Ib, or a physiologically acceptable salt thereof, as claimed in claim 1, comprising reacting a compound of formula IIa or IIb with a compound of formula III to give a compound of formula IVa or IVb,

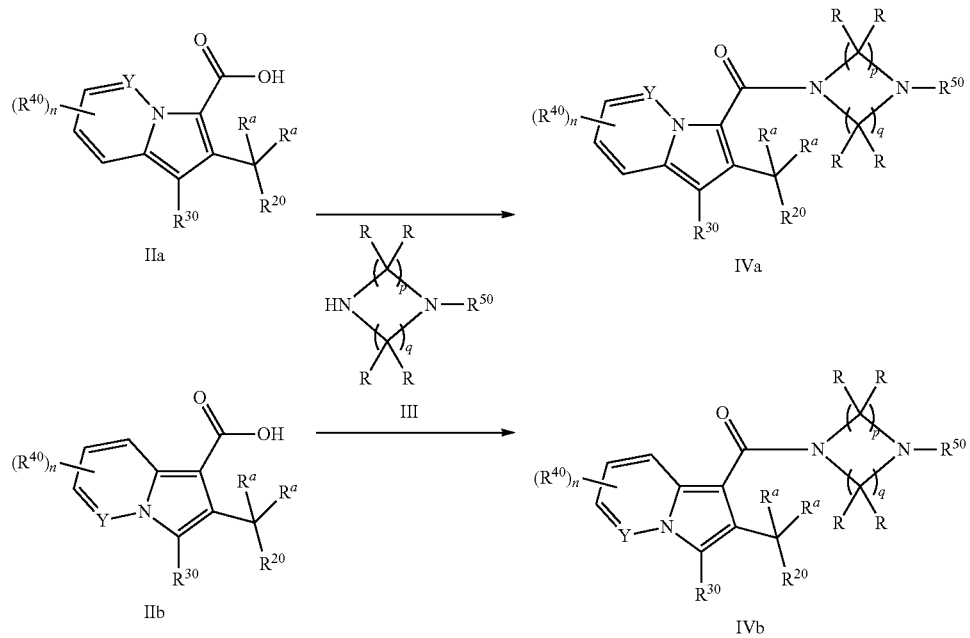

wherein R, $R^a$, $R^{20}$, $R^{30}$, $R^{40}$, Y, n, p and q are defined as in claim 1 and additionally functional groups can be present in protected form or in the form of a precursor group, and $R^{50}$ is defined as $R^{10}$ in claim 1 with the exception of hydrogen, or $R^{50}$ is a protective group, and removing the protective group $R^{50}$ in case of the preparation of a compound of the formula Ia or Ib in which $R^{10}$ is hydrogen.

10. A pharmaceutical composition, which comprises at least one compound of the formula Ia or Ib as claimed in claim 1 or a physiologically acceptable salt thereof and a pharmaceutically acceptable carrier.

11. A method for the treatment of hypertension, the method comprising administering to a patient in need thereof an effective dose of a compound as claimed in claim 1.

* * * * *

UNITED STATES PATENT AND TRADEMARK OFFICE
CERTIFICATE OF CORRECTION

PATENT NO.        : 8,415,336 B2
APPLICATION NO.   : 13/353889
DATED             : April 9, 2013
INVENTOR(S)       : Henning Steinhagen et al.

It is certified that error appears in the above-identified patent and that said Letters Patent is hereby corrected as shown below:

In the Specification

In column 40, line 1, delete " 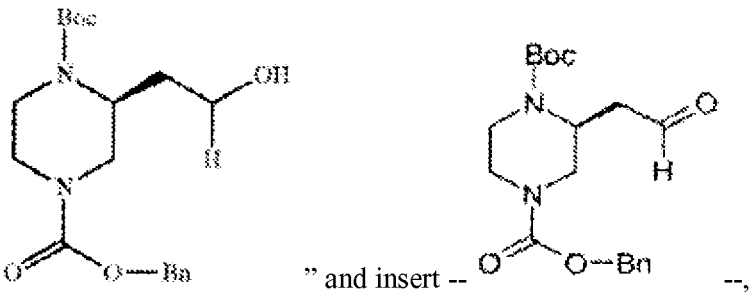 " and insert -- -- therefor.

In the Claims

In column 80, line 43, in claim 5, after " $(C_1-C_4)$-alkyl, " insert -- $(C_1-C_4)$-alkyl-O-, --.

Signed and Sealed this
Third Day of September, 2013

Teresa Stanek Rea
*Acting Director of the United States Patent and Trademark Office*